United States Patent
Kaur et al.

(10) Patent No.: US 12,129,227 B2
(45) Date of Patent: Oct. 29, 2024

(54) METHODS, PROCESSES, AND COMPOSITIONS FOR IMPROVED PREPARATION OF HU308 AND HU433

(71) Applicant: Tetra Bio-Pharma Inc., Orleans (CA)

(72) Inventors: Harpreet Kaur, Brampton (CA); Xuejun Liu, Toronto (CA); Prabin Nepal, Toronto (CA); Subakar Paramanantham, Scarborough (CA); Monika Garg, Etobicoke (CA); Zemin Li, Woodbridge (CA); Andy Tjeng, Toronto (CA); Moises Rodriguez, Moncton (CA); Laura Jong, Montreal (CA); Azam Mirzahossein, Blainville (CA); Ofer Yifrach-Stav, Cote Saint Luc (CA); Erin Bassett, Nepean (CA); Randy Ringuette, Nepean (CA); Charles Campbell, Kanata (CA); Melanie Kelly, Fergusons Cove (CA)

( * ) Notice: Subject to any disclaimer, the term of this patent is extended or adjusted under 35 U.S.C. 154(b) by 0 days.

(21) Appl. No.: 18/027,897

(22) PCT Filed: Sep. 23, 2021

(86) PCT No.: PCT/CA2021/051327
§ 371 (c)(1),
(2) Date: Mar. 22, 2023

(87) PCT Pub. No.: WO2022/061461
PCT Pub. Date: Mar. 31, 2022

(65) Prior Publication Data
US 2023/0271908 A1 Aug. 31, 2023

Related U.S. Application Data

(60) Provisional application No. 63/082,986, filed on Sep. 24, 2020.

(51) Int. Cl.
| | |
|---|---|
| C07C 41/26 | (2006.01) |
| C07C 29/48 | (2006.01) |
| C07C 67/08 | (2006.01) |
| C07C 67/29 | (2006.01) |
| C07C 67/293 | (2006.01) |
| C07C 269/06 | (2006.01) |

(52) U.S. Cl.
CPC .............. *C07C 41/26* (2013.01); *C07C 29/48* (2013.01); *C07C 67/08* (2013.01); *C07C 67/29* (2013.01); *C07C 67/293* (2013.01); *C07C 269/06* (2013.01); *C07B 2200/07* (2013.01); *C07C 2602/42* (2017.05)

(58) Field of Classification Search
CPC ..... C07C 41/26; C07C 67/297; C07C 231/18; C07C 2602/42; C07B 2200/07
See application file for complete search history.

(56) References Cited

U.S. PATENT DOCUMENTS 9,428,431 B2 * 8/2016 Bab .......................... A61P 19/10

OTHER PUBLICATIONS

International Search Report and Written Opinion, dated Jan. 13, 2022 for International Application No. PCT/CA2021/051327.
De Richter et al., (+)- and (−)-[2-(1,3-dithianyl)]myrtanylborane. Solid and stable monoalkylboranes for asymmetric hydroboration. J Org Chem. Apr. 1, 1990;55(9):2855-60. doi: 10.1021/JO00296A054.
Hanus et al., HU-308: a specific agonist for $CB_2$, a peripheral cannabinoid receptor. Proc Natl Acad Sci U S A. Dec. 7, 1999;96(25):14228-33. doi: 10.1073/pnas.96.25.14228.

(Continued)

*Primary Examiner* — Rosalynd A Keys
(74) *Attorney, Agent, or Firm* — Wolf, Greenfield & Sacks, P.C.

(57) ABSTRACT

Disclosed herein are methods, processes and compositions for preparing a compound of formula 8: (8), and formula 18: (18). The methods and processes comprise performing a first allylic oxidation, a protection reaction, a second allylic oxidation, a reduction reaction, performing an acid-catalyzed coupling reaction, a methylation reaction and a deprotection reaction. Disclosed herein are methods, processes and compositions for enantioselectively preparing compounds of formulae 8 and 18. Also disclosed herein are compositions comprising compounds of formulae 8, 18 and/or intermediates and/or starting material thereof.

formula 8

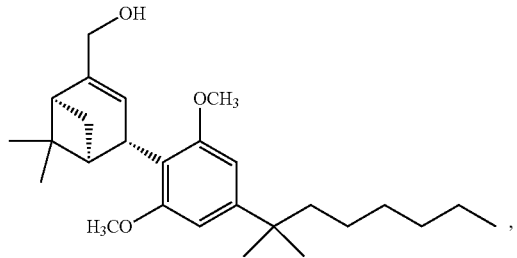

formula 18

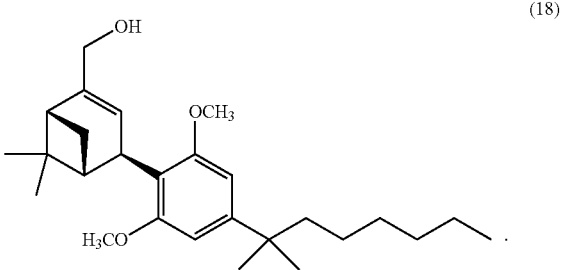

20 Claims, 52 Drawing Sheets

(56) References Cited

OTHER PUBLICATIONS

Mechoulam et al., Synthesis of the individual, pharmacologically distinct, enantiomers of a tetrahydrocannabinol derivative. Tetrahedron: Assymmetry. 1990;1(5):315-8. doi: 10.1016/S0957-4166(00)86322-3.

Smoum et al., CB2 cannabinoid receptor agonist enantiomers HU-433 and HU-308: An inverse relationship between binding affinity and biological potency. Proc Natl Acad Sci U S A. Jul. 14, 2015;112(28):8774-9. doi: 10.1073/pnas.1503395112. Epub Jun. 29, 2015.

* cited by examiner

FIGURE 10

Certificate of Analysis

| Name of Product: | Lot Number: |
|---|---|
| HU308 <br> *(4-[4-(1,1-Dimethylheptyl)-2,6-dimethoxyphenyl]-6,6-dimethyl bicyclo[3.1.1]hept-2-ene-2-methanol)* | HU-03-173A-070919 |

| Manufacture Date: | Retested On: | Next Retest Date: |
|---|---|---|
| 07/09/19 | n/a | 07/08/20 |

Recommended Storage Conditions:
☐ Ambient atmosphere ☒ Inert atmosphere
☐ Ambient temperature ☐ 2-8°C (refrigeration) ☒ -20°C or below (freezer)

| Structure: | Molecular Formula: |
|---|---|
| [chemical structure] | $C_{27}H_{42}O_3$ |
| | Molecular Weight: 414.63 |
| | CAS Number: 256934-39-1 |

| | |
|---|---|
| Appearance: | White semi solid |
| Purity: | 98.7% by HPLC at 215 nm |
| Identity: | $^1$H-NMR - conforms to structure |
| | $^{13}$C-NMR - conforms to structure |
| MS(ESI+ve): | $[M+H]^+$ = 415.2; $[M-H_2O+H]^+$ = 397.2; $[M+NH_4]^+$ = 431.9 - conforms to structure |
| Karl Fisher: | 0.26% water content (Volumetric) |
| Optical rotation: | $[\alpha]_D$ = +102.3° (conc.=2, chloroform) |
| Residual Solvents: | DCM 875 ppm |
| | Hexanes 7 ppm |
| | EtOAc 7 ppm |
| | Pentane 31,839 ppm |
| | MeOH Not Detected |

FIGURE 16

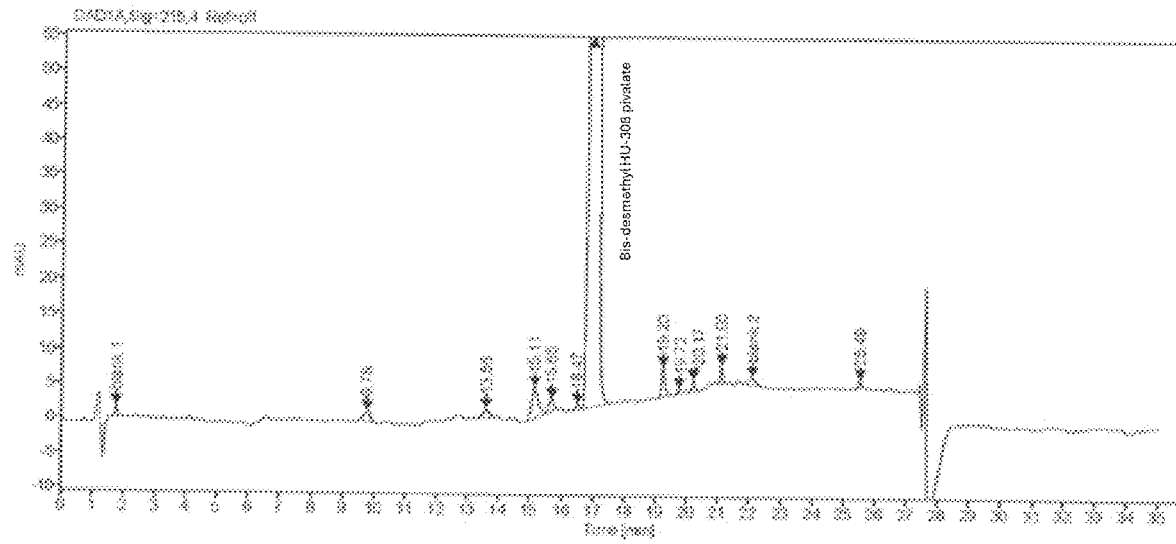

| # | RT (min) | RRT | Signal | Type | Area | Peak Area Percent | Peak Height | Name |
|---|---|---|---|---|---|---|---|---|
| 1 | | | DAD1A | | | | | HU/308 Pivalate |
| 2 | | | DAD1A | | | | | HU/308 |
| 3 | 1.73879 | | DAD1A | BB | 9.02750 | 0.06 | 1.55387 | Blank 1 |
| 4 | 9.75022 | | DAD1A | BB | 21.41037 | 0.14 | 1.53382 | Unknown |
| 5 | 13.56328 | | DAD1A | BB | 19.58790 | 0.12 | 1.27180 | Unknown |
| 6 | 15.11477 | | DAD1A | BV | 64.86808 | 0.41 | 4.48382 | Unknown |
| 7 | 15.68677 | | DAD1A | VB | 20.48463 | 0.13 | 1.62380 | Unknown |
| 8 | 16.48879 | | DAD1A | BB | 6.63900 | 0.04 | 0.77104 | Unknown |
| 9 | 16.88429 | | DAD1A | BV | 15613.73663 | 98.60 | 1484.68859 | Bis-des HU/308 Pivalate |
| 10 | 19.19862 | | DAD1A | BB | 30.10344 | 0.19 | 4.27988 | Unknown |
| 11 | 19.71782 | | DAD1A | BB | 4.09910 | 0.03 | 0.68197 | Unknown |
| 12 | 20.17143 | | DAD1A | BB | 11.04692 | 0.07 | 1.69545 | Unknown |
| 13 | 21.05508 | | DAD1A | BB | 12.42590 | 0.08 | 2.64185 | Unknown |
| 14 | 22.08821 | | DAD1A | BB | 15.71808 | 0.10 | 1.08698 | Blank 2 |
| 15 | 25.48358 | | DAD1A | BB | 7.34179 | 0.05 | 1.14383 | Unknown |
| | | | | Sum | 15836.15223 | 100.00 | | |

Purity of Intermediate 6a $$= \frac{\text{area of intermediate}}{\text{Total Are} - \text{Blank Area}} = \frac{15613.73663}{15836.15223 - 9.02750 - 15.71808}$$

$$= 98.7\% \ (11/21/19)$$

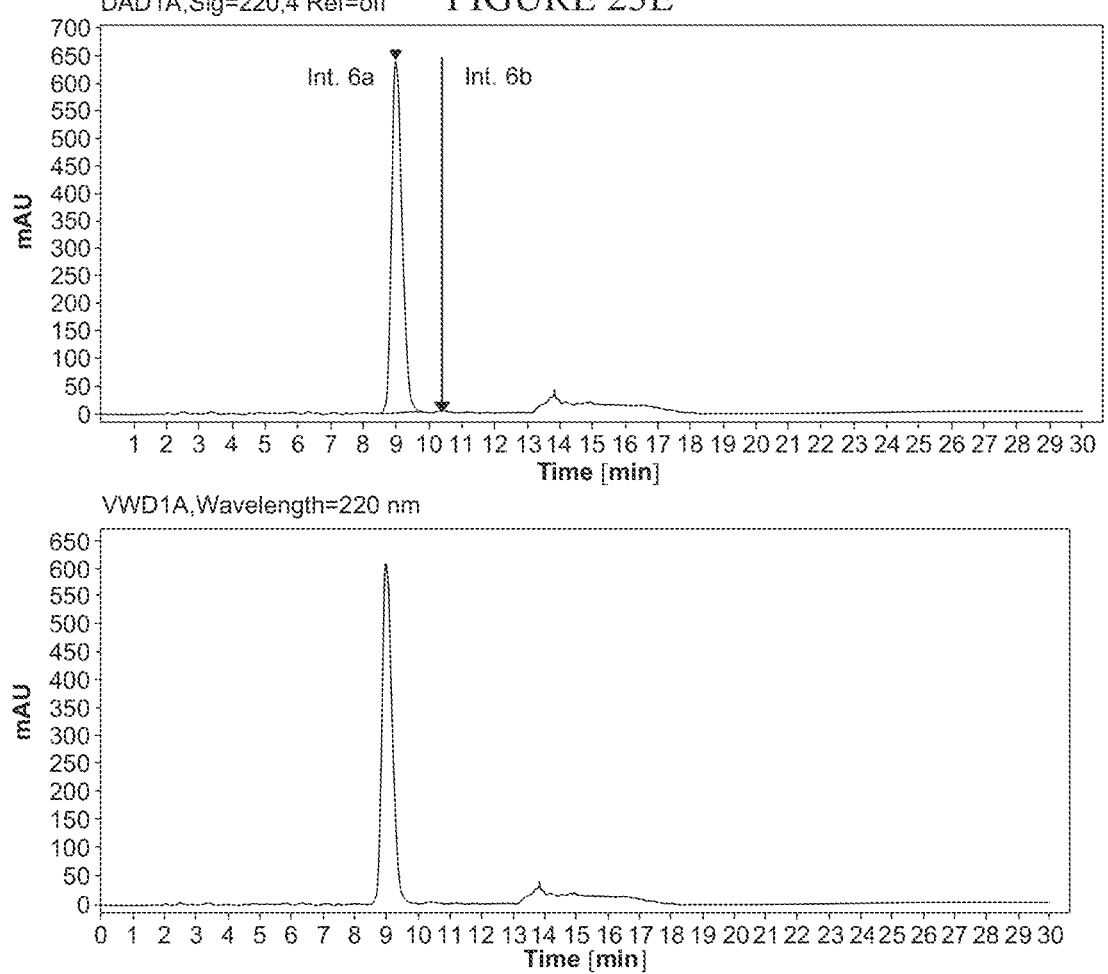

| # | RT [min] | RRT | Signal | Type | Area | Peak Area Percent | Peak Height | Name |
|---|----------|-----|--------|------|------|-------------------|-------------|------|
| 1 | 8.97243 |  | DAD1A | BV | 14354.66655 | 99.31 | 642.64083 | Int.6a |
| 2 | 10.37790 |  | DAD1A | VB | 99.07329 | 0.69 | 4.09009 | Int.6b |
|  |  |  |  | Sum | 14453.73983 | 100.0 |  |  |

FIGURE 23F
(Cont'd)

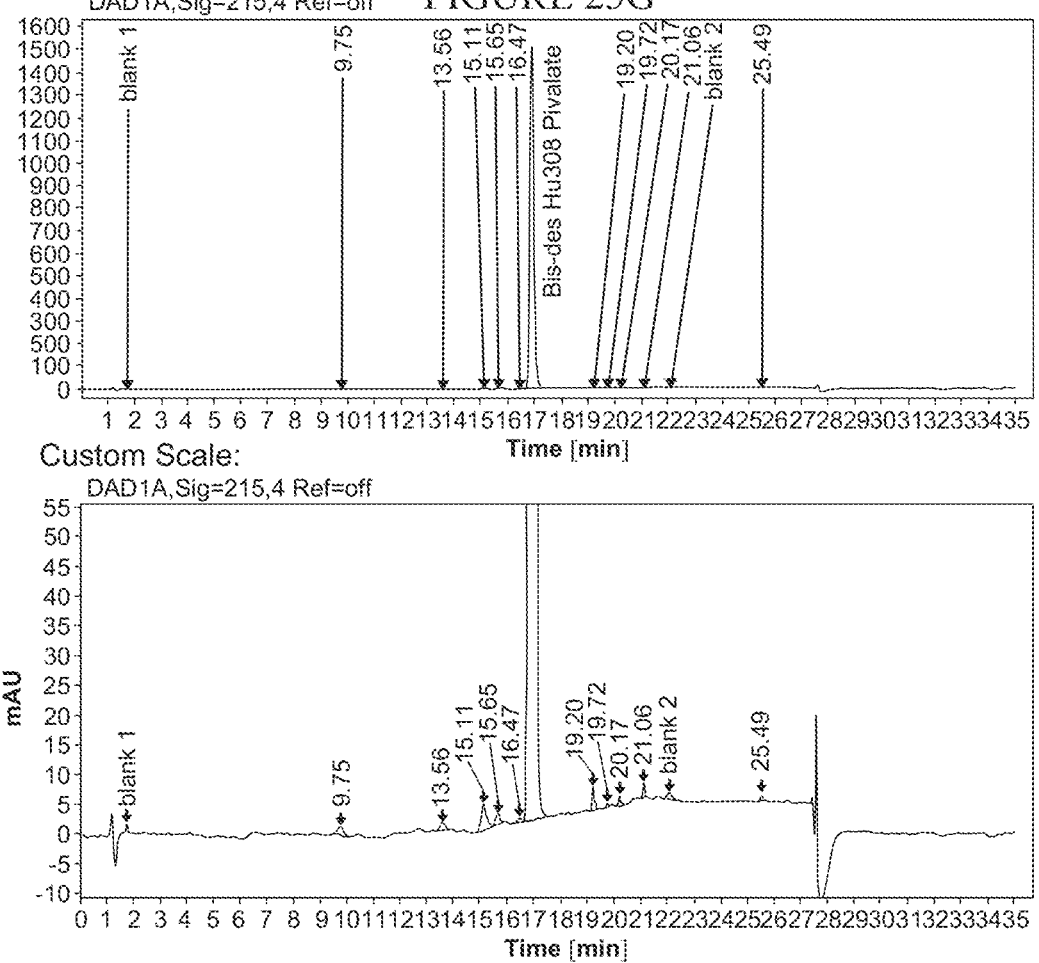

| # | RT [min] | RRT | Signal | Type | Area | Peak Area Percent | Peak Height | Name |
|---|----------|-----|--------|------|------|-------------------|-------------|------|
| 1 | | | DAD1A | | | | | Hu308 Pivalate |
| 2 | | | DAD1A | | | | | Hu308 |
| 3 | 1.73676 | | DAD1A | BB | 9.02750 | 0.06 | 1.65397 | blank 1 |
| 4 | 9.75022 | | DAD1A | BB | 21.41037 | 0.14 | 1.53382 | Unknown |
| 5 | 13.56329 | | DAD1A | BB | 19.58790 | 0.12 | 1.27100 | Unknown |
| 6 | 15.11477 | | DAD1A | BV | 64.66808 | 0.41 | 4.45382 | Unknown |
| 7 | 15.65077 | | DAD1A | VB | 20.45453 | 0.13 | 1.82060 | Unknown |
| 8 | 16.65077 | | DAD1A | BB | 6.63900 | 0.04 | 0.77104 | Unknown |
| 9 | 16.88429 | | DAD1A | BV | 1561.73663 | 98.60 | 1484.09859 | Bis-des Hu308 Pivalate |
| 10 | 19.19862 | | DAD1A | BB | 30.10344 | 0.19 | 4.27956 | Unknown |
| 11 | 19.71762 | | DAD1A | BB | 4.09510 | 0.03 | 0.68197 | Unknown |
| 12 | 20.17143 | | DAD1A | BB | 11.04692 | 0.07 | 1.69545 | Unknown |
| 13 | 21.05908 | | DAD1A | BB | 12.42590 | 0.08 | 2.64185 | Unknown |
| 14 | 22.06621 | | DAD1A | BB | 15.71808 | 0.10 | 1.08698 | blank 2 |
| 15 | 25.48956 | | DAD1A | BB | 7.24179 | 0.05 | 1.14383 | Unknown |
| | | | | Sum | 15836.15523 | 100.0 | | |

Certificate of Analysis

| Name of Product: | Lot Number: |
|---|---|
| HU308 | HU-05-179-121119 |
| *(4-[4-(1,1-Dimethylheptyl)-2,6-dimethoxyphenyl]-6,6-dimethyl bicyclo[3.1.1]hept-2-ene-2-methanol)* | |

| Manufacture Date: | Retested On: | Next Retest Date: |
|---|---|---|
| 12/11/19 | n/a | 12/10/20 |

Recommended Storage Conditions:
☐ Ambient atmosphere ☒ Inert atmosphere
☐ Ambient temperature ☐ 2-8°C (refrigeration) ☒ -20°C or below (freezer)

| Structure: | Molecular Formula: |
|---|---|
| | $C_{27}H_{42}O_3$ |
| | Molecular Weight: 414.63 |
| | CAS Number: 256934-39-1 |

| | |
|---:|:---|
| Appearance: | White powder |
| Purity: | 99.64% by HPLC at 215 nm (TM-0698, R0) |
| Enantiomeric Excess: | 98.37% (TM-0713, R0) |
| Identity: | $^1$H-NMR - conforms to structure |
| | $^{13}$C-NMR - conforms to structure |
| MS(ESI+Ve): | $[M-H_2O+H]^+$ = 397.2; $[M+Na]^+$ = 437.2 - conforms to structure |
| FT-IR: | Refer to the attached spectrum |
| Karl Fisher: | 1.1271% water content (Volumetric) |
| Residual Solvent: | DCM     not detected |
| | Hexanes    < LOQ (58 ppm) |
| | EtOAc     < LOQ (1000 ppm) |
| | Acetone    < LOQ (1000 ppm) |
| | MeOH      < LOQ (600 ppm) |
| | MTBE      < LOQ (1000 ppm) |
| Elemental Impurities: | Arsenic: <0.10 ppm |
| | Cadmium: ≤0.10 ppm |
| | Mercury: < 0.10 ppm |
| | Lead: <0.10 ppm |

FIGURE 24F
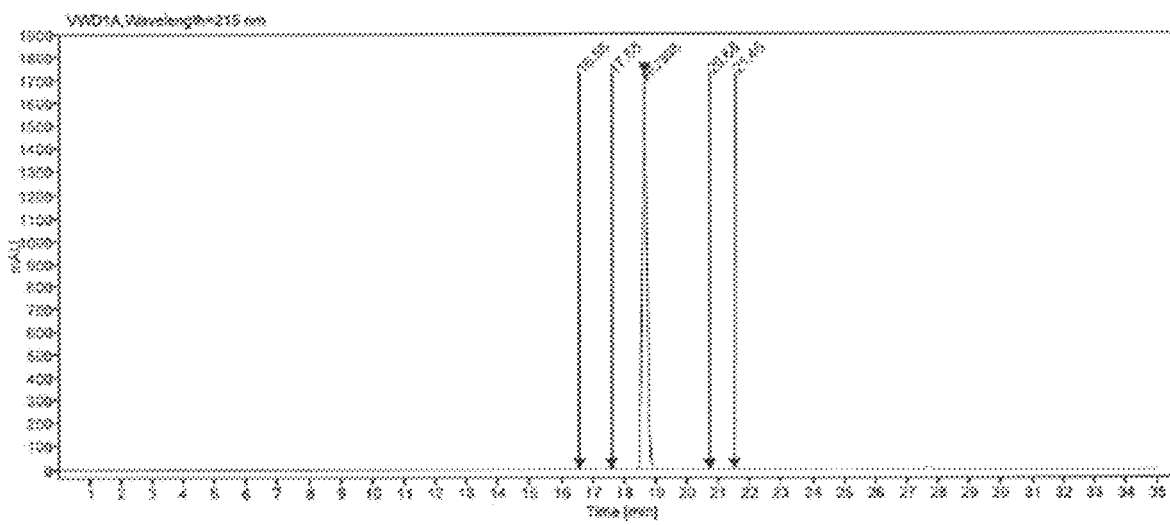
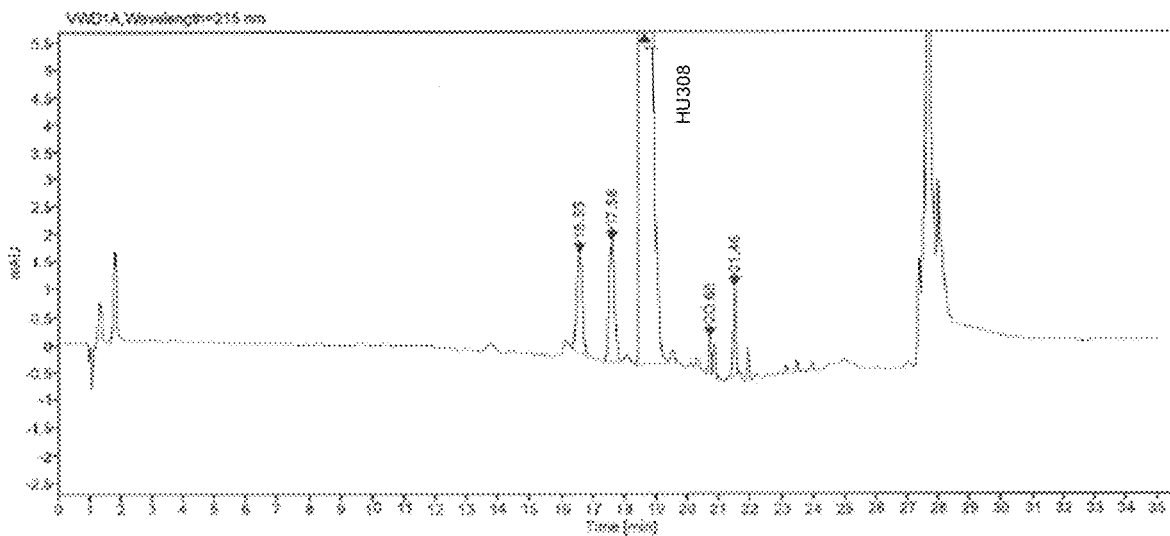

FIGURE 24G

| # | RT [min] | RRT | Signal | Type | Area | Peak Area Percent | Peak Height | Name |
|---|----------|-----|--------|------|------|-------------------|-------------|------|
| 1 | | | VWD1A | | | | | Bis-desmethoxy HU308 pivalate |
| 2 | | | VWD1A | | | | | HU308 Pivalate |
| 3 | 16.54629 | | VWD1A | BB | 23.31971 | 0.13 | 1.76787 | Unknown |
| 4 | 17.57947 | | VWD1A | BB | 27.78589 | 0.16 | 2.17274 | Unknown |
| 5 | 18.81436 | | VWD1A | BV | 17810.67419 | 99.64 | 1730.74933 | HU308 |
| 6 | 20.68921 | | VWD1A | BV | 4.16798 | 0.02 | 0.68921 | Unknown |
| 7 | 21.45731 | | VWD1A | BB | 9.56635 | 0.05 | 1.58388 | Unknown |
| | | | | Sum | 17875.51412 | 100.00 | | |

FIGURE 25

Chiral Purity of HU308 Drug Substance and HU433

[Illegible project information header]

| Parameter | Acceptance Criteria | Result | Pass/Fail |
|---|---|---|---|
| Resolution Solution: Resolution between HU433 and Intermediate to USP tailing factor for HU308 and HU433 peaks USP plate count for HU308 and HU433 peaks | NLT 1.5 NMT 2.0 NLT 2000 | 1.75 1.01, 1.08 XXX, 4403 | Pass |
| Signal/Noise for HU308 in the Sensitivity Solution | NLT 10 | 73 | Pass |
| %Difference of Enantiomeric Excess between duplicate injections of same sample | NMT 2% | 0.02-0.17 | Pass |
| Signal/Noise for HU308 in the Bracketing Solution | NLT 10 | 62 | Pass |

| Name / Sample Lot | Injection # | HU308 Retention Time (min) | Peak Area HU308 | HU433 Retention Time (min) | Peak Area HU433 | % HU308 | % HU433 | % Enantiomeric Excess (EE) | Average % Enantiomeric Excess (EE) | % Difference of Enantiomeric Excess (EE) |
|---|---|---|---|---|---|---|---|---|---|---|
| HU308 / HU-06-87 | 1 | 5.135 | 8013.04712 | 8.657 | 60.98633 | 99.24605 | 0.75394 | 98.48692 | 98.46 | 0.05 |
| | 2 | 5.133 | 8012.89701 | 8.659 | 63.26860 | 99.23623 | 0.76377 | 98.43246 | | |
| HU308 / HU-06-179 | 1 | 5.147 | 8873.21546 | 8.703 | 73.35708 | 99.18988 | 0.81012 | 98.37977 | 98.37 | 0.02 |
| | 2 | 5.134 | 8982.06573 | 8.658 | 74.09835 | 99.18179 | 0.81821 | 98.36358 | | |
| HU433 / HU-06-71-4 | 1 | 5.159 | 330.47798 | 8.430 | 8078.15117 | 3.93118 | 96.06882 | 92.13764 | 92.22 | 0.17 |
| | 2 | 5.232 | 323.89480 | 8.651 | 8077.27840 | 3.85306 | 96.14694 | 92.29388 | | |

FIGURE 26A

Certificate of Analysis

| Name of Product: | | Lot Number: |
|---|---|---|
| HU433 | | HU-06-139-T1-022820 |
| ((1R,4R,5R)-4-(2,6-dimethoxy-4-(2-methyloctan-2-yl)phenyl)-6,6-dimethylbicyclo[3.1.1]hept-2-en-2-yl)methanol | | |
| Manufacture Date: | Retested On: | Next Retest Date: |
| 02/28/20 | n/a | 02/27/22 |
| Recommended Storage Conditions: | | |
| ☐ Ambient atmosphere  ☒ Inert atmosphere | | |
| ☐ Ambient temperature  ☐ 2-8°C (refrigeration)  ☒ -20°C or below (freezer) | | |

| Structure: | Molecular Formula: |
|---|---|
| 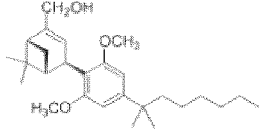 | $C_{27}H_{42}O_3$ |
| | Molecular Weight: |
| | 414.63 |
| | CAS Number: |
| | 1220887-84-2 |

| | |
|---|---|
| Appearance: | White powder |
| Identity: | $^1$H-NMR - conforms to structure |
| | $^{13}$C-NMR - conforms to structure |
| MS(ESI+ve): | $[M-H_2O+H]^+$ = 397.1 conforms to structure |
| Purity: | 99.4% by HPLC at 215 nm (TM-0698 R1) |
| Enantiomeric Excess: | 94.41% (TM-0713, R1) |
| FT-IR: | Refer to the attached spectrum |
| Karl Fisher: | 0.35% |
| Residual Solvent: | MeOH     25 ppm |
| | Hexanes  9 ppm |
| | EtOAc    Not detected |

| | |
|---|---|
| Elemental Impurities: | Arsenic: < 0.10 ppm |
| | Cadmium: < 0.10 ppm |
| | Mercury: < 0.10 ppm |
| | Lead: < 0.140 ppm |

FIGURE 26B

Enantiomeric Excess

Project Code: CS-2975
Test date: 03/12/20
Sequence: mz031220

Method: TM-0713 R#1
Ref.: MZ-09-95

SST Acceptance Criteria

| Solution | System Suitability Parameters | Acceptance Criteria | Result | Pass / Fail |
|---|---|---|---|---|
| Resolution | Resolution between HU308 intermediate 6a and HU433 | NLT 1.5 | 2.0 | Pass |
| | USP tailing factor for HU308 | NMT 2.0 | 1.0 | Pass |
| | USP tailing factor for HU433 | NMT 2.0 | 1.0 | Pass |
| | USP plate count for HU308 | NLT 2000 | 3340 | Pass |
| | USP plate count for HU433 | NLT 2000 | 3464 | Pass |
| Sensitivity | S/N of HU308 | NLT 10 | 377 | Pass |
| RDS#01505 | %Difference of Enantiomeric Excess between duplicate injections of sample | NMT 2% | 0 | Pass |
| Bracketing | S/N of HU308 | NLT 10 | 504 | Pass |

% Enantiomeric Excess of HU433

| RDS#01505 | Peak | %Peak Area | %EE | % Diff. of EE |
|---|---|---|---|---|
| 1 | HU433 | 96.81 | 94.42 | 0.02 |
| | HU308 | 2.78 | | |
| 2 | HU433 | 96.84 | 94.40 | |
| | HU308 | 2.79 | | |

| # | RT [min] | RRT | Signal | Type | Area | Peak Area Percent | Peak Height | Name |
|---|---|---|---|---|---|---|---|---|
| 1 | 15.86646 | | VWD1A | BB | 24.65660 | 0.12931 | 1.18462 | Unknown |
| 2 | 16.96272 | | VWD1A | BB | 26.21489 | 0.13748 | 1.69815 | Unknown |
| 3 | 18.13458 | | VWD1A | BB | 18949.77179 | 99.38258 | 1469.58769 | HU-433 |
| 4 | 20.58026 | | VWD1A | VB | 57.06724 | 0.14 | 7.21997 | Unknown |
| 5 | 21.23810 | | VWD1A | VB | 9.78746 | 0.12 | 1.29036 | Unknown |
| | | | | Sum | 19.067.49798 | 100.00 | | |
| | | | | | | | | |

FIGURE 26G
(Cont'd)

FIGURE 26H
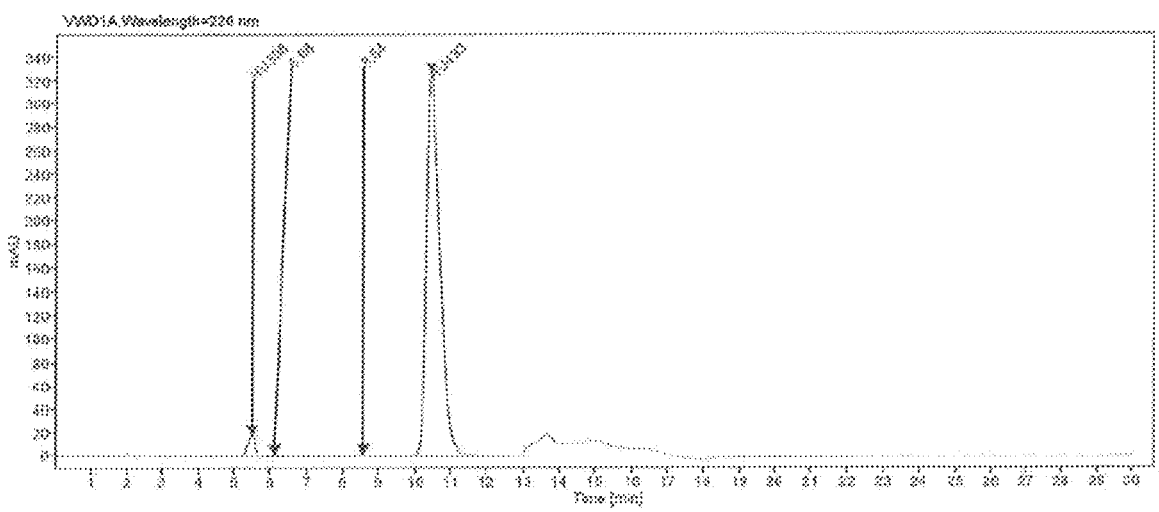
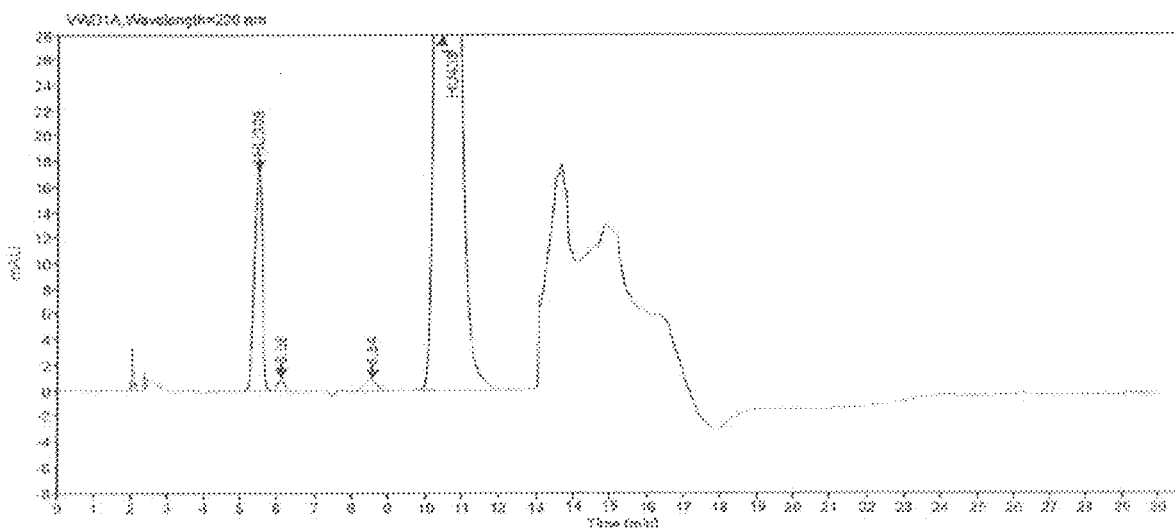

FIGURE 26H (Cont'd)

| # | RT [min] | RRT | Signal | Type | Area | Peak Area Percent | Peak Height | Name |
|---|----------|-----|--------|------|------|-------------------|-------------|------|
| 1 | 5.48808 |  | VWD1A | BB | 246.32453 | 2.78546 | 17.22839 | HU308 |
| 2 | 6.08393 |  | VWD1A | BB | 12.48939 | 0.13987 | 1.00530 | Unknown |
| 3 | 8.53795 |  | VWD1A | BB | 20.52026 | 0.23018 | 2.85881 | Unknown |
| 4 | 10.41838 |  | VWD1A | BB | 8833.85842 | 98.84447 | 326.23443 | HU433 |
|  |  |  |  | Sum | 8914.97062 | 100.00 |  |  |

METHODS, PROCESSES, AND COMPOSITIONS FOR IMPROVED PREPARATION OF HU308 AND HU433

RELATED APPLICATIONS

This application is a national stage filing under 35 U.S.C. § 371 of International PCT Application PCT/CA2021/051327, filed Sep. 23, 2021, which claims priority under 35 U.S.C. § 119(e) to U.S. Provisional Application, U.S. Ser. No. 63/082,986, filed on Sep. 24, 2020, each of which is incorporated herein by reference in its entirety.

FIELD OF INVENTION

The present invention relates to improvements of synthetic methodology of synthetic cannabinoid derivatives; more specifically, improvements of synthetic methodology of HU308 and HU433.

BACKGROUND OF THE INVENTION

Chemical synthesis of cannabinoids and their derivatives have been hampered by several issues, such as low natural yields, structural complexity and multiple stereocenters. Drug-like molecules with multiple stereocenters present unique challenges to chemical synthesis, such as chiral impurities that arise from impure starting materials or chemical steps with poor enantioselectivity. Enantiomeric impurities are particularly challenging, as they may be difficult to separate or purify from the desired molecule. In general, enantiomers are difficult to separate via conventional techniques, such as recrystallization or general chromatographic procedures.

((1S,4S,5S)-4-(2,6-dimethoxy-4-(2-methyloctan-2-yl) phenyl)-6,6-dimethylbicyclo[3.1.1]hept-2-en-2-yl)methanol (HU308) is a synthetic cannabidiol derivative that was previously identified as a potent peripheral CB2-selective agonist. HU308 has also been shown to display properties such as anti-inflammatory, analgesic, neuroprotective or antitumor effects, and has been used as a pharmacological tool in numerous cannabinoid studies. More recently, the efficacy of HU308 and its enantiomer ((1R,4R,5R)-4-(2,6-dimethoxy-4-(2-methyloctan-2-yl)phenyl)-6,6-dimethylbicyclo[3.1.1]hept-2-en-2-yl)methanol (HU433), have been tested in ovariectomy-induced bone loss and ear inflammation.

There exists a need to efficiently synthesize HU308 and its enantiomer, HU433, and to overcome current challenges in the art.

SUMMARY OF THE INVENTION

Provided herein are improved methods and processes for synthesizing HU308 and HU433. As described in detail herein below, synthetic processes have been developed to provide an improved synthesis of HU308 and HU433. In certain embodiments, the procedures described herein display an improved yield and/or improved stereoisomeric purity over synthetic procedures known in the art. Described herein is methodology, processes and compositions pertaining to HU308 and HU433 and corresponding starting materials, and intermediates.

According to the present invention there is provided methods, processes and compositions for preparing a compound of formula 8:

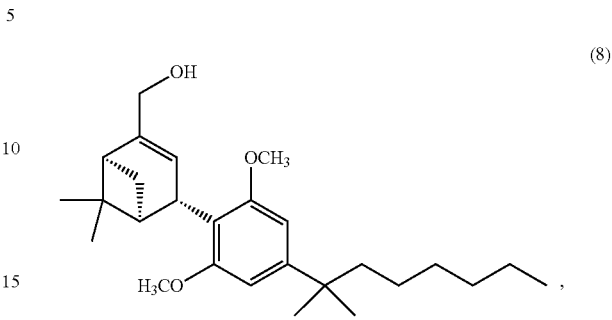
(8)

the method or process comprising: providing a first reactant of formula 9:

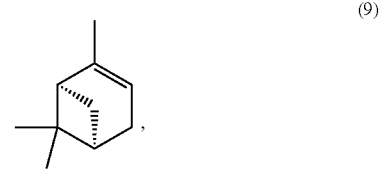
(9)

performing a first allylic oxidation comprising compound 9, an oxidant such as $SeO_2$, and peroxide to yield a compound of formula 3:

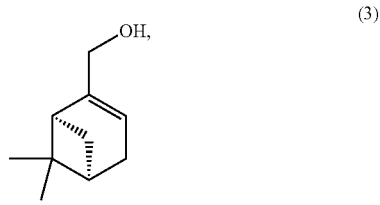
(3)

performing a protection reaction comprising compound 3, an acid halide such as an acid chloride, a solvent such as dichloromethane (DCM), and a first base to yield a compound of formula 4:

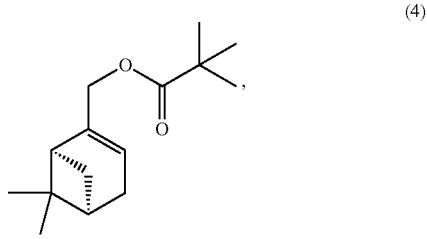 [SMILES: CC(C)(C)C(=O)OCC1=CC[C@@H]2C[C@H]1C2(C)C]
(4)

performing a second allylic oxidation comprising compound 4, an oxidant such as $CrO_3$, a peroxide such as tert-butyl hydroperoxide (TBHP), and a first solvent to yield a compound of formula 5:

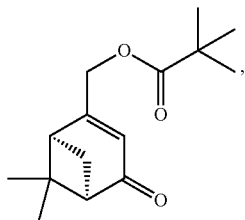
(5)

performing a reduction reaction comprising compound 5, a reducing agent such as sodium borohydride (NaBH$_4$), and a solvent, such as ethanol, to yield a compound of formula 1:

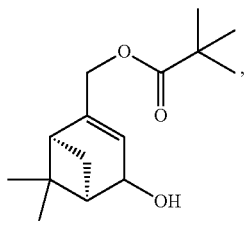
(1)

performing an acid-catalyzed coupling reaction comprising compound 1, an acid, DCM, and a compound of formula 2:

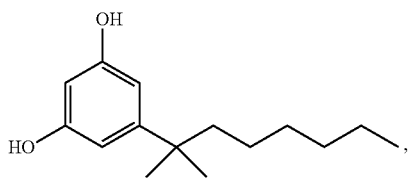
(2)

to yield a compound of formula 6:

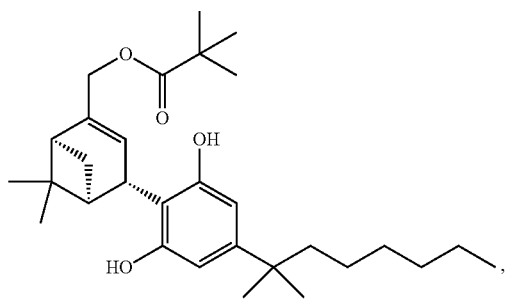
(6)

performing a methylation reaction comprising compound 6, dimethyl sulfate (Me$_2$SO$_4$), and potassium carbonate (K$_2$CO$_3$) to yield a compound of formula 7:

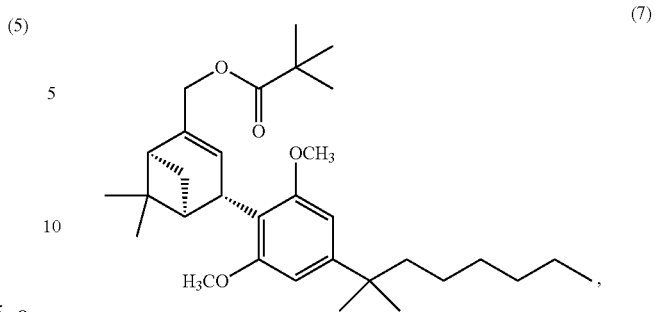
(7)

performing a deprotection reaction comprising a second base and a second solvent to yield the compound of formula 8, and isolating the compound of formula 8.

According to the present invention there is provided methods, processes and compositions for preparing a compound of formula 8:

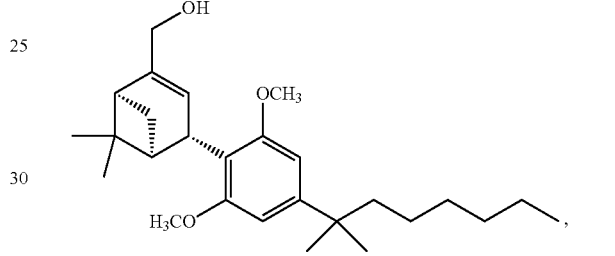
(8)

the method or process comprising: providing a compound of formula 3:

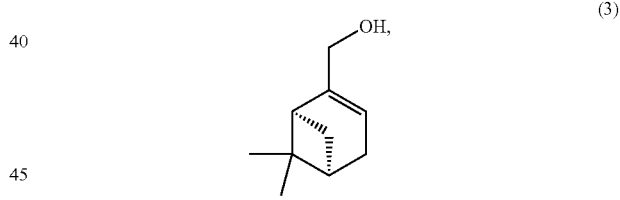
(3)

performing a protection reaction comprising compound 3, an acid halide such as an acid chloride, a solvent such as dichloromethane (DCM), and a first base to yield a compound of formula 4:

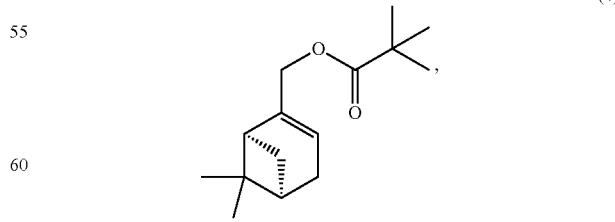
(4)

performing a second allylic oxidation comprising compound 4, an oxidant such as CrO$_3$, a peroxide such as tert-butyl hydroperoxide (TBHP), and a first solvent to yield a compound of formula 5:

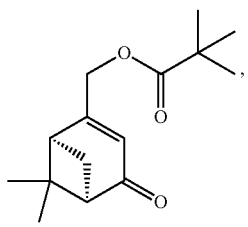

(5)

performing a reduction reaction comprising compound 5, a reducing agent such as sodium borohydride (NaBH$_4$), and a solvent, such as ethanol, to yield a compound of formula 1:

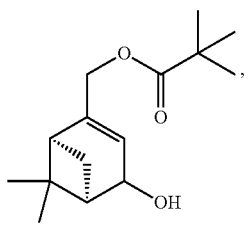

(1)

performing an acid-catalyzed coupling reaction comprising compound 1, an acid, DCM, and a compound of formula 2:

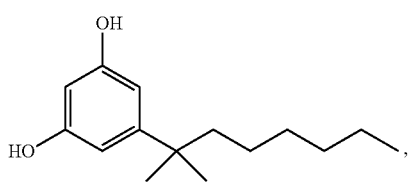

(2)

to yield a compound of formula 6:

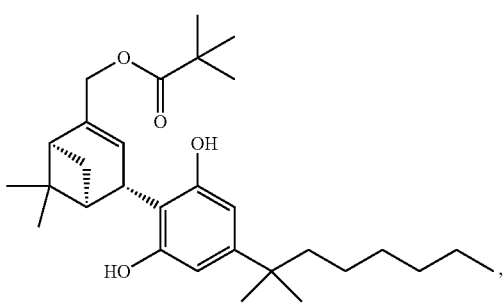

(6)

performing a methylation reaction comprising compound 6, dimethyl sulfate (Me$_2$SO$_4$), and potassium carbonate (K$_2$CO$_3$) to yield a compound of formula 7:

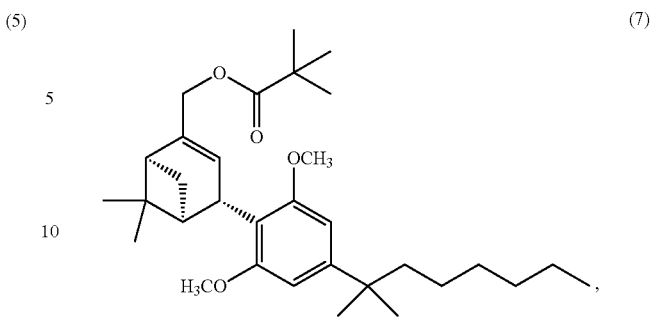

(7)

performing a deprotection reaction comprising a second base and a second solvent to yield the compound of formula 8, and isolating the compound of formula 8.

In some embodiments of the above methods, processes and/or compositions, the method, process and/or composition further comprises:
providing a first reactant of formula 9:

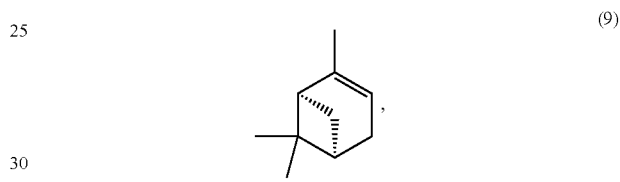

(9)

and performing a first allylic oxidation comprising compound 9, an oxidant such as SeO$_2$, and peroxide to yield compound 3.

In some embodiments of the above methods, processes and/or compositions, the peroxide may be tert-butyl hydroperoxide (TBHP). In a further embodiment, the first allylic oxidation may comprise 1 eq. compound 9, 0.036-1.19 eq. SeO$_2$, and 0-3.5 eq. peroxide. In further embodiments, the first allylic oxidation may comprise 0.036 eq. SeO$_2$, 2.0 eq. TBHP, 0.45 eq. NaBH$_4$, and may be conducted at room temperature.

In some embodiments of the above methods, processes and/or compositions, the acid chloride may be pivaloyl chloride. In a further embodiment, the first base may be trimethylamine (TEA), 4-dimethylaminopyridine (DMAP) or pyridine. In a further embodiment, the protection reaction may comprise 1 eq. compound 3, 1.2-2.0 eq. acid chloride, 6 vol. of dichloromethane (DCM), and 1.5-6 eq. of the first base. In yet further embodiments, the acid chloride may be pivaloyl chloride, the first base may be pyridine, and the protection reaction may comprise 1.2 eq. pivaloyl chloride, 1.5 eq. first base and 6 vol. of DCM.

In some embodiments of the above methods, processes and/or compositions, the second allylic oxidation may comprise 1 eq. compound 4, 0.05-0.5 eq. CrO$_3$, 3.15-7 eq. tert-butyl hydroperoxide (TBHP), and 14.6-16 vol. of the first solvent. In further embodiments, the first solvent may be acetonitrile (ACN) or DCM. In yet further embodiments, the second allylic oxidation may comprise 0.5 eq. CrO$_3$, 3.15 eq. TBHP, 14.6 vol. of first solvent and the second allylic oxidation may occur at an initial temperature of 0° C. and a final temperature of room temperature, and the first solvent may be ACN. In some embodiments, the second allylic oxidation may comprise 0.05 eq. CrO$_3$, 7 eq. TBHP, and 16 vol. of solvent, the second allylic oxidation may occur at room temperature, and the solvent may be DCM.

In some embodiments of the above methods, processes and/or compositions, the reduction reaction may comprise 1 eq. of compound 5, 1.05-1.32 eq. of sodium borohydride (NaBH$_4$) and 10-18 vol. of ethanol (EtOH) and may be conducted at room temperature. In further embodiments, the reduction reaction may comprise 1.1 eq. of NaBH$_4$, 10 vol. of EtOH and may be conducted at room temperature over a period of 30 minutes.

In some embodiments of the above methods, processes and/or compositions, the acid may be para-toluenesulfonic acid (pTSA) or MeSO$_3$H. In further embodiments, the acid-catalyzed coupling reaction may comprise 1.02-1.1 eq. of compound 1, 0.05-0.28 eq. of pTSA, 35-112 vol. of DCM, and 1 eq. of the compound of formula 2. In further embodiments, the acid-catalyzed coupling reaction may comprise 1.02 eq. of compound 1, 0.1 eq. of pTSA, 35 vol. of DCM, and 1 eq. of the compound of formula 2. In yet further embodiments, the acid-catalyzed coupling reaction may comprise 0.05-0.2 eq. of MeSO$_3$H, 1.02 eq. of compound 1, 112 vol. of DCM and 1 eq. of the compound of formula 2. In some embodiments, the acid-catalyzed coupling reaction may comprise 0.2 eq. of MeSO$_3$H, 1.02 eq. of compound 1, 112 vol. of DCM and 1 eq. of the compound of formula 2.

In some embodiments of the above methods, processes and/or compositions, the methylation reaction may comprise 1 eq. of compound 6, 2.5-5 eq. dimethyl sulfate (Me$_2$SO$_4$), 5.3-6.7 eq. of potassium carbonate (K$_2$CO$_3$) and 5-20 vol. of acetone. In some embodiments, the methylation reaction may comprise 4 eq. of Me$_2$SO$_4$, 5.3 eq. of K$_2$CO$_3$, 20 vol. of acetone, and is conducted at room temperature over a period of 72 hours.

In some embodiments of the above methods, processes and/or compositions, the deprotection reaction may comprise 1 eq. of compound 7, 2-9 eq. of the second base and 20-155 vol. of the second solvent. In some embodiments, the second base may be 2.4 eq. of lithium aluminum hydride (LiAlH$_4$) and the second solvent may be 75-155 vol. of tetrahydrofuran (THF). In further embodiments, the second base may be 6 eq. of potassium tert-butoxide, the second solvent may be 88 vol. of methyl tert-butyl ester (MTBE) and the deprotection reaction may further comprise 1.6 eq. of water. In some embodiments, the second base may be 2-9 eq. of potassium hydroxide, the second solvent may be 80 vol. of methanol and the deprotection reaction may further comprise 1 mL of water. In still further embodiments, the second base may be 6-9 eq. of sodium methoxide, the second solvent may be 20-88 vol. of methanol and the deprotection reaction may further comprise 1.6-22 eq. of water. In some embodiments, the second base may be 9 eq. of sodium methoxide, the second solvent may be 20 vol. of methanol, the deprotection reaction may further comprises 22 eq. of water and may be conducted at a temperature of 37° C.

Disclosed herein are methods, processes and compositions for preparing a compound for formula 3:

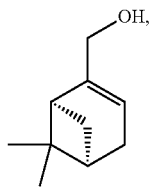

(3)

the method, process or composition comprising, providing a first reactant of formula 9:

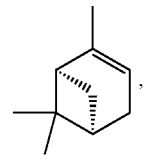

(9)

and performing a first allylic oxidation comprising compound 9, an oxidant such as SeO$_2$, and peroxide to yield a compound of formula 3.

In some embodiments of the above methods, processes and/or compositions, the peroxide may be tert-butyl hydroperoxide (TBHP). In a further embodiment, the first allylic oxidation may comprise 1 eq. compound 9, 0.036-1.19 eq. SeO$_2$, and 0-3.5 eq. peroxide. In further embodiments, the first allylic oxidation may comprise 0.036 eq. SeO$_2$, 2.0 eq. TBHP, 0.45 eq. NaBH$_4$, and may be conducted at room temperature.

Disclosed herein are methods, processes and compositions for preparing a compound for formula 4:

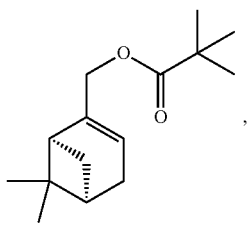

(4)

the method, process or composition comprising, providing a compound of formula 3:

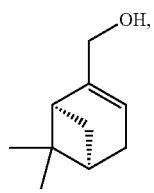

(3)

and performing a protection reaction comprising compound 3, an acid halide, such as an acid chloride, a solvent such as dichloromethane (DCM), and a first base to yield a compound of formula 4.

In some embodiments of the above methods, processes and/or compositions, the acid chloride may be pivaloyl chloride. In a further embodiment, the first base may be trimethylamine (TEA), 4-dimethylaminopyridine (DMAP) or pyridine. In a further embodiment, the protection reaction may comprise 1 eq. compound 3, 1.2-2.0 eq. acid chloride, 6 vol. of dichloromethane (DCM), and 1.5-6 eq. of the first base. In yet further embodiments, the acid chloride may be pivaloyl chloride, the first base may be pyridine, and the protection reaction may comprise 1.2 eq. pivaloyl chloride, 1.5 eq. first base and 6 vol. of DCM.

Disclosed herein are methods, processes and compositions for preparing a compound of formula 5:

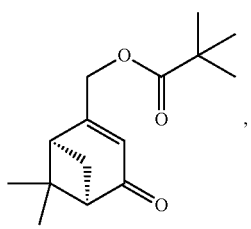
(5)

the method, process or composition comprising, providing a compound of formula 4:

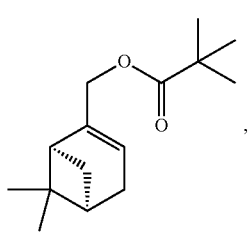
(4)

and performing a second allylic oxidation comprising compound 4, an oxidant such as CrO₃, a peroxide such as tert-butyl hydroperoxide (TBHP), and a first solvent to yield a compound of formula 5.

In some embodiments of the above methods, processes and/or compositions, the second allylic oxidation may comprise 1 eq. compound 4, 0.05-0.5 eq. CrO₃, 3.15-7 eq. tert-butyl hydroperoxide (TBHP), and 14.6-16 vol. of the first solvent. In further embodiments, the first solvent may be acetonitrile (ACN) or DCM. In yet further embodiments, the second allylic oxidation may comprise 0.5 eq. CrO₃, 3.15 eq. TBHP, 14.6 vol. of first solvent and the second allylic oxidation may occur at an initial temperature of 0° C. and a final temperature of room temperature, and the first solvent may be ACN. In some embodiments, the second allylic oxidation may comprise 0.05 eq. CrO₃, 7 eq. TBHP, and 16 vol. of solvent, the second allylic oxidation may occur at room temperature, and the solvent may be DCM.

Disclosed herein are methods, processes and compositions for preparing a compound of formula 1:

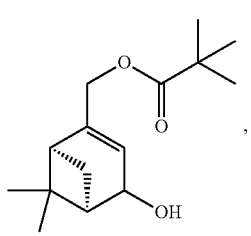
(1)

the method, process or composition comprising, providing a compound of formula 5:

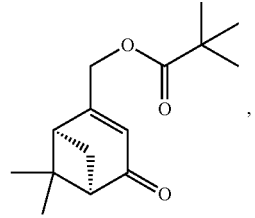
(5)

and performing a reduction reaction comprising compound 5, a reducing agent such as sodium borohydride (NaBH₄), and a solvent such as ethanol, to yield a compound of formula 1.

In some embodiments of the above methods, processes and/or compositions, the reduction reaction may comprise 1 eq. of compound 5, 1.05-1.32 eq. of sodium borohydride (NaBH₄) and 10-18 vol. of ethanol (EtOH) and may be conducted at room temperature. In further embodiments, the reduction reaction may comprise 1.1 eq. of NaBH₄, 10 vol. of EtOH and may be conducted at room temperature over a period of 30 minutes.

Disclosed herein are methods, processes and compositions for preparing a compound of formula 6:

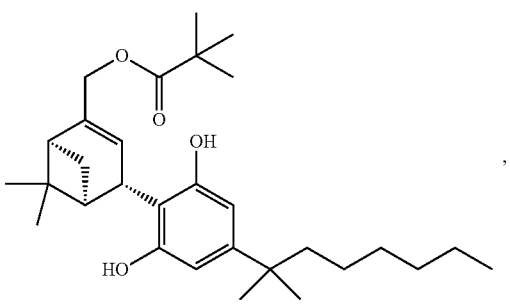
(6)

the method, process or composition comprising, providing a compound of formula 1:

and

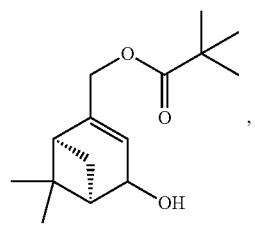
(1)

performing an acid-catalyzed coupling reaction comprising compound 1, an acid, DCM, and a compound of formula 2:

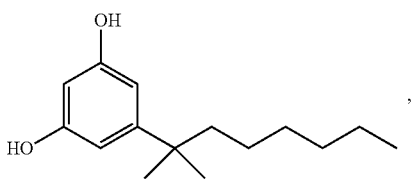
(2)

to yield a compound of formula 6.

In some embodiments of the above methods, processes and/or compositions, the acid may be para-toluenesulfonic acid (pTSA) or MeSO₃H. In further embodiments, the acid-catalyzed coupling reaction may comprise 1.02-1.1 eq. of compound 1, 0.05-0.28 eq. of pTSA, 35-112 vol. of DCM, and 1 eq. of the compound of formula 2. In further embodiments, the acid-catalyzed coupling reaction may comprise 1.02 eq. of compound 1, 0.1 eq. of pTSA, 35 vol. of DCM, and 1 eq. of the compound of formula 2. In yet further embodiments, the acid-catalyzed coupling reaction may comprise 0.05-0.2 eq. of MeSO₃H, 1.02 eq. of compound 1, 112 vol. of DCM and 1 eq. of the compound of formula 2. In some embodiments, the acid-catalyzed coupling reaction may comprise 0.2 eq. of MeSO₃H, 1.02 eq. of compound 1, 112 vol. of DCM and 1 eq. of the compound of formula 2.

Disclosed herein are methods, processes and compositions for preparing a compound of formula 7:

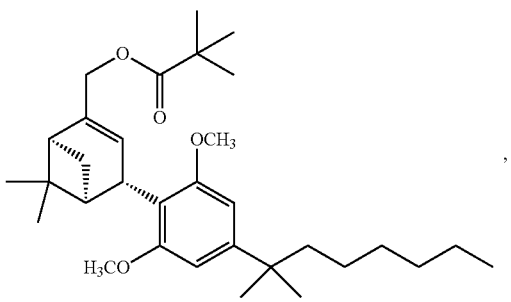
(7)

the method, process or composition comprising, providing a compound of formula 6:

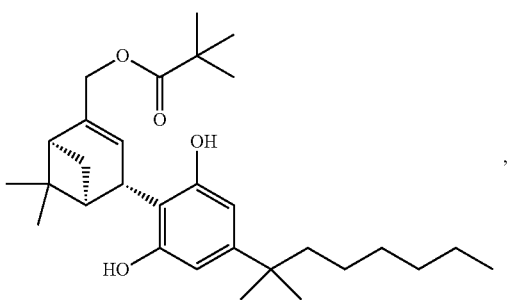
(6)

and
performing a methylation reaction comprising compound 6, dimethyl sulfate (Me₂SO₄), and potassium carbonate (K₂CO₃) to yield a compound of formula 7.

In some embodiments of the above methods, processes and/or compositions, the methylation reaction may comprise 1 eq. of compound 6, 2.5-5 eq. dimethyl sulfate (Me₂SO₄), 5.3-6.7 eq. of potassium carbonate (K₂CO₃) and 5-20 vol. of acetone. In some embodiments, the methylation reaction may comprise 4 eq. of Me₂SO₄, 5.3 eq. of K₂CO₃, 20 vol. of acetone, and is conducted at room temperature over a period of 72 hours.

Disclosed herein are methods, processes and compositions for preparing a compound of formula 8:

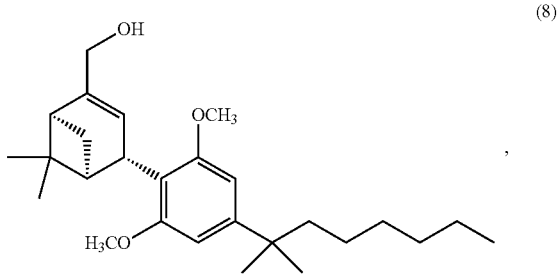 [SMILES: CCCCCCC(C)(C)c1cc(OC)c([C@H]2C=C(CO)[C@H]3C[C@@H]2C3(C)C)c(OC)c1]
(8)

the method, process or composition comprising, providing a compound of formula 7:

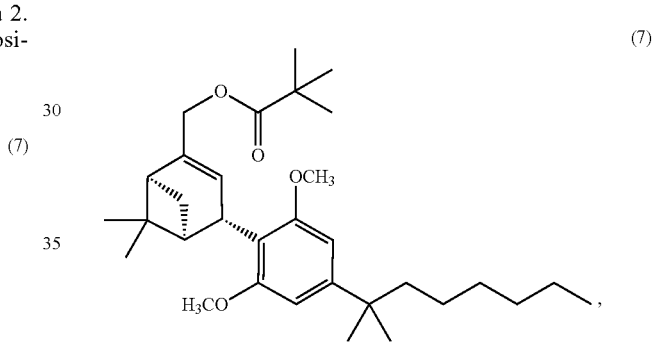
(7)

performing a deprotection reaction comprising a second base and a second solvent to yield the compound of formula 8, and isolating the compound of formula 8.

In some embodiments of the above methods, processes and/or compositions, the deprotection reaction may comprise 1 eq. of compound 7, 2-9 eq. of the second base and 20-155 vol. of the second solvent. In some embodiments, the second base may be 2.4 eq. of lithium aluminum hydride (LiAlH₄) and the second solvent may be 75-155 vol. of tetrahydrofuran (THF). In further embodiments, the second base may be 6 eq. of potassium tert-butoxide, the second solvent may be 88 vol. of methyl tert-butyl ester (MTBE) and the deprotection reaction may further comprise 1.6 eq. of water. In some embodiments, the second base may be 2-9 eq. of potassium hydroxide, the second solvent may be 80 vol. of methanol and the deprotection reaction may further comprise 1 mL of water. In still further embodiments, the second base may be 6-9 eq. of sodium methoxide, the second solvent may be 20-88 vol. of methanol and the deprotection reaction may further comprise 1.6-22 eq. of water. In some embodiments, the second base may be 9 eq. of sodium methoxide, the second solvent may be 20 vol. of methanol, the deprotection reaction may further comprises 22 eq. of water and may be conducted at a temperature of 37° C.

Disclosed herein are methods, processes and compositions for enantioselectively preparing a compound of formula 8:

(8)

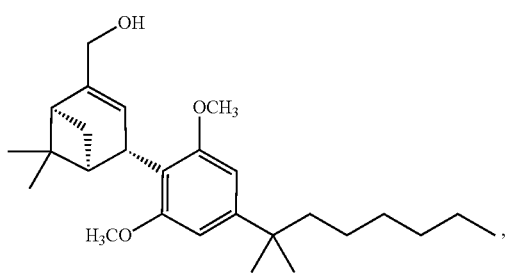

the method, process or composition comprising: providing a first reactant of formula 12, (12)

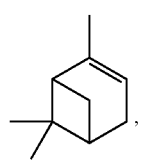

performing a first allylic oxidation comprising compound 12, an oxidant such as SeO₂, and peroxide to yield a compound of formula 13:

(13)

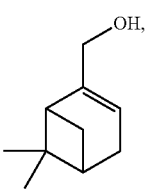

performing a protection reaction comprising compound 13, an acid halide, such as an acid chloride, a solvent such as dichloromethane (DCM), and a first base to yield a compound of formula 14:

(14)

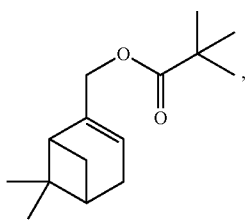

performing a second allylic oxidation comprising compound 14, an oxidant such as CrO₃, a peroxide such as tert-butyl hydroperoxide (TBHP), a first solvent to yield a compound of formula 15:

(15)

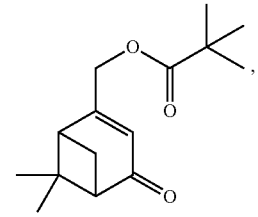

performing a reduction reaction comprising compound 15, a reducing agent such as sodium borohydride (NaBH₄), and a solvent, such as ethanol, to yield a compound of formula 16:

(16)

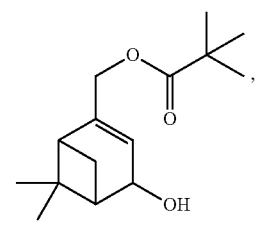

performing an acid-catalyzed coupling reaction comprising compound 16, an acid, DCM, and a compound of formula 2:

(2)

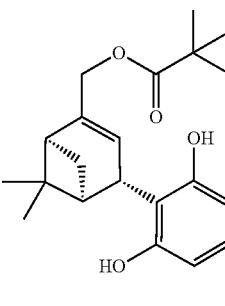

to yield a first mixture comprising a compound of formula 6:

(6)

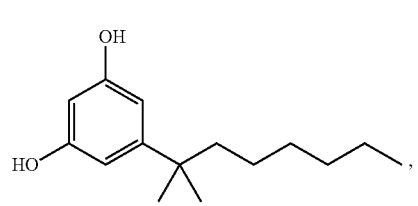

and a compound of formula 17:

(17)

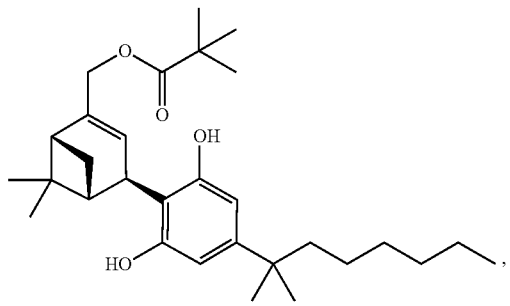

performing a coupling reaction comprising the first mixture, Boc-alanine, N,N'-dicyclohexylcarbodiimide (DCC), and 4-dimethylaminopyridine (DMAP) to yield a second mixture comprising a compound of formula 10:

(10)

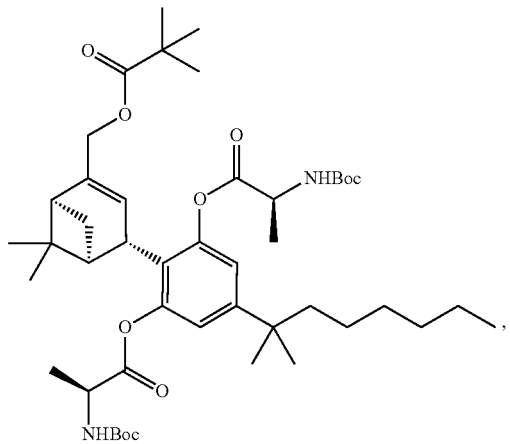

and a compound of formula 11:

(11)

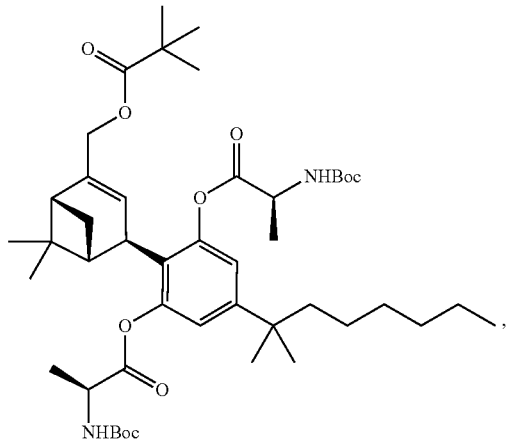

purifying the second mixture to yield enantiomerically purified compound 10, performing a hydrolysis reaction comprising enantiomerically purified compound 10, a third base and a third solvent, to yield enantiomerically purified compound 6, performing a methylation reaction comprising enantiomerically purified compound 6, dimethyl sulfate ($Me_2SO_4$), potassium carbonate ($K_2CO_3$) and acetone to yield an enantiomerically purified compound of formula 7:

(7)

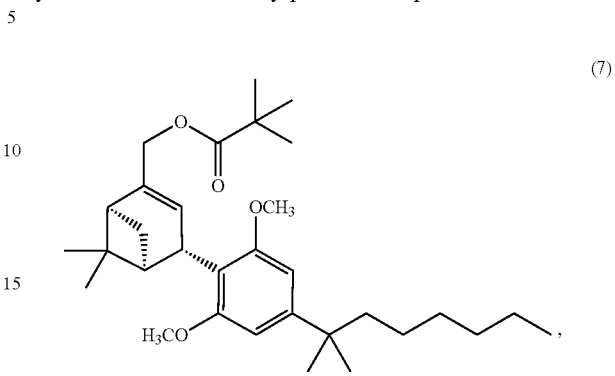

performing a deprotection reaction comprising enantiomerically purified compound 7, a second base and a second solvent to yield the enantiomerically purified compound 8; and isolating the enantiomerically purified compound 8.

Disclosed herein are methods, processes and compositions for preparing a compound of formula 13:

(13)

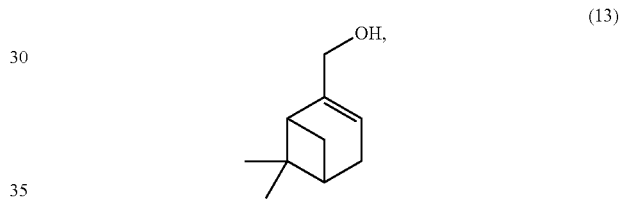

the method, process or composition comprising: providing a first reactant of formula 12, (12)

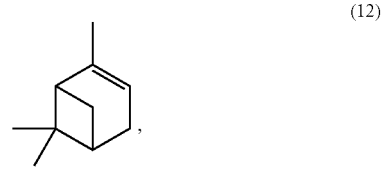

and
performing a first allylic oxidation comprising compound 12, an oxidant such as $SeO_2$, and peroxide to yield a compound of formula 13.

Disclosed herein are methods, processes and compositions for preparing a compound of formula 14:

(14)

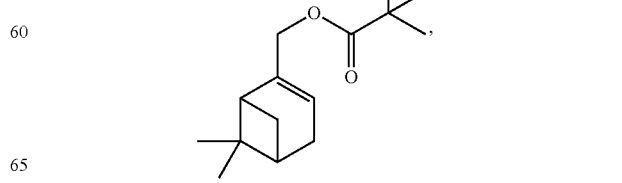

the method or process comprising: providing a first reactant of formula 13:

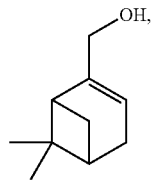

(13)

and performing a protection reaction comprising compound 13, an acid halide, such as an acid chloride, a solvent such as dichloromethane (DCM), and a first base to yield a compound of formula 14.

Disclosed herein are methods, processes and compositions for preparing a compound of formula 15:

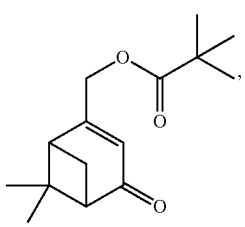

(15)

the method or process comprising: providing a first reactant of formula 14, and performing a second allylic oxidation comprising compound 14, an oxidant such as CrO$_3$, a peroxide such as tert-butyl hydroperoxide (TBHP), a first solvent to yield a compound of formula 15.

Disclosed herein are methods, processes and compositions for preparing a compound of formula 16:

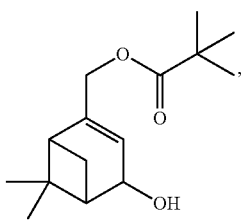

(16)

the method or process comprising: providing a first reactant of formula 15, and performing a reduction reaction comprising compound 15, sodium borohydride (NaBH$_4$) and ethanol to yield a compound of formula 16.

Disclosed herein are methods, processes and compositions for preparing a first mixture comprising a compound of formula 6:

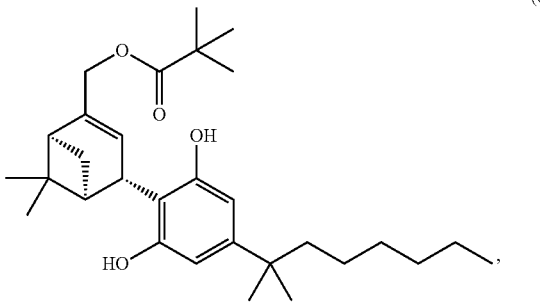

(6)

and a compound of formula 17:

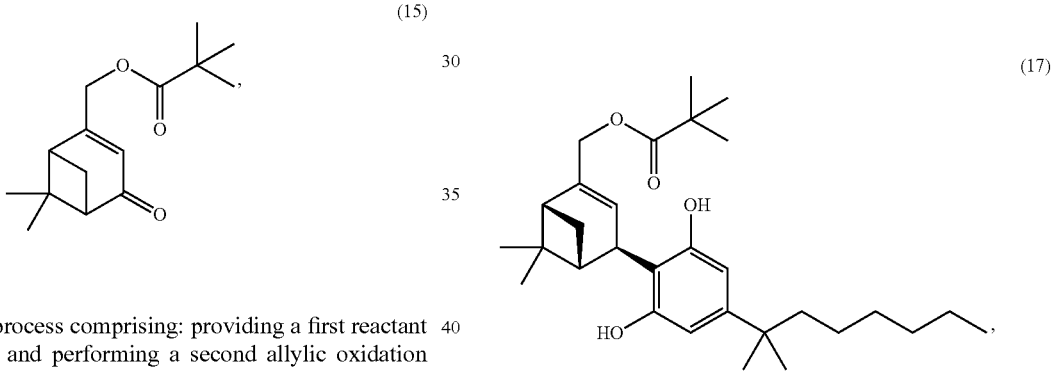

(17)

the method or process comprising providing a compound of formula 16, and performing an acid-catalyzed coupling reaction comprising compound 16, an acid, DCM, and a compound of formula 2:

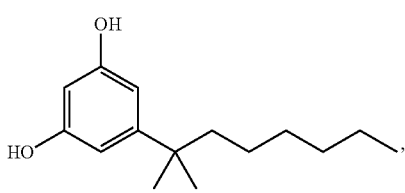

(2)

to yield the first mixture.

Disclosed herein are methods, processes and compositions for preparing a second mixture comprising a compound of formula 10:

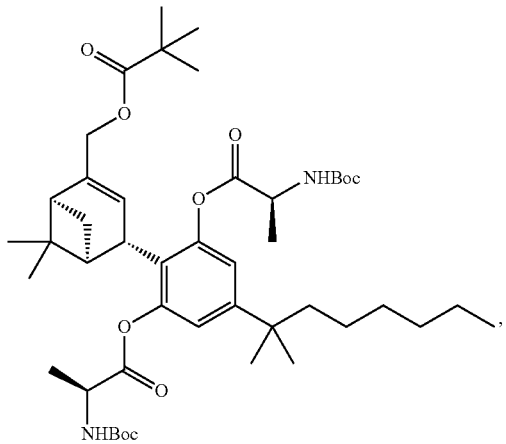

(10)

and a compound of formula 11:

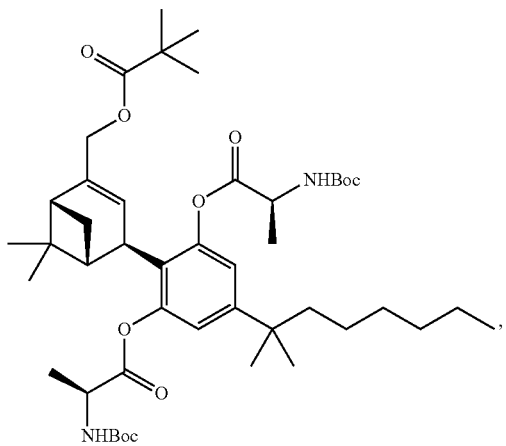

(11)

the method or process comprising, providing a first mixture of compounds 6 and 17, and performing a coupling reaction comprising the first mixture, Boc-alanine, N,N'-dicyclohexylcarbodiimide (DCC), and 4-dimethylaminopyridine (DMAP) to yield the second mixture.

Disclosed herein are methods, processes and compositions for enantioselectively preparing a compound of formula 10:

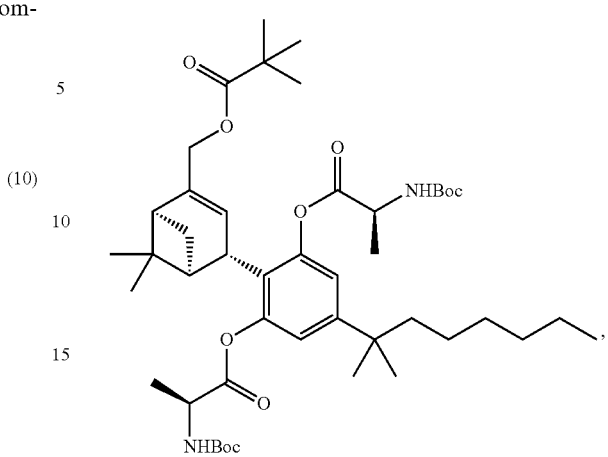

(10)

the method of process comprising, providing a second mixture comprising a compound of formula 10 and a compound of formula 11:

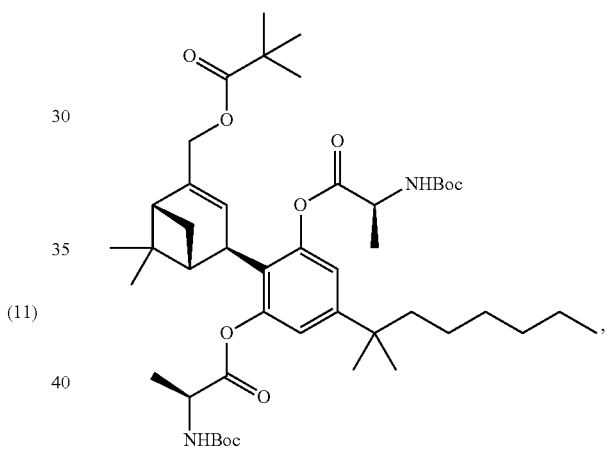

(11)

purifying the second mixture to yield enantiomerically purified compound 10.

Disclosed herein are methods, processes and compositions for enantioselectively preparing a compound of formula 6:

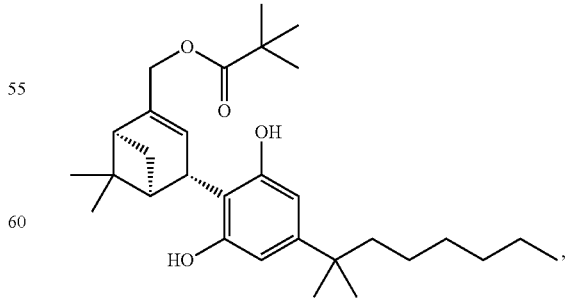

(6)

the method of process comprising, providing an enantiomerically purified compound 10, and performing a hydrolysis reaction comprising enantiomerically purified compound 10, a third base and a third solvent, to yield enantiomerically purified compound 6.

Disclosed herein are methods, processes and compositions for enantioselectively preparing a compound of formula 7:

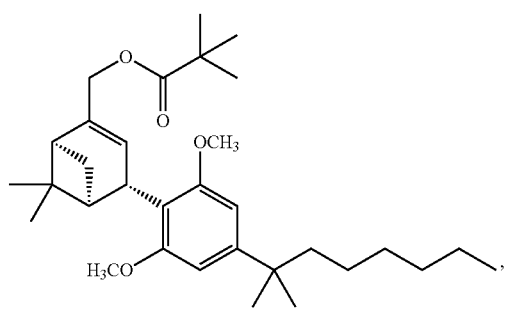

(7)

the method of process comprising providing an enantiomerically purified compound 6, and performing a methylation reaction comprising enantiomerically purified compound 6, dimethyl sulfate ($Me_2SO_4$), potassium carbonate ($K_2CO_3$) and acetone to yield an enantiomerically purified compound of formula 7.

Disclosed herein are methods, processes and compositions for enantioselectively preparing a compound of formula 8:

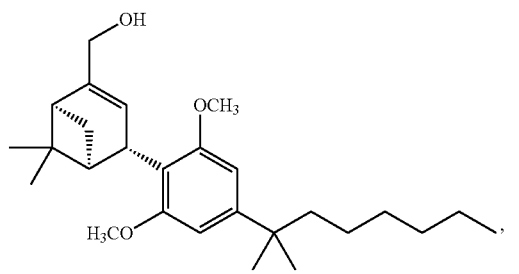

(8)

the method of process comprising providing an enantiomerically purified compound 7, and performing a deprotection reaction comprising enantiomerically purified compound 7, a second base and a second solvent to yield the enantiomerically purified compound 8; and isolating the enantiomerically purified compound 8.

In some embodiments of the above methods, compositions or processes, the peroxide may be tert-butyl hydroperoxide (TBHP). In a further embodiment, the first allylic oxidation may comprise 1 eq. compound 9, 0.036-1.19 eq. $SeO_2$, and 0-3.5 eq. peroxide. In further embodiments, the first allylic oxidation may comprise 0.036 eq. $SeO_2$, 2.0 eq. TBHP, 0.45 eq. $NaBH_4$, and may be conducted at room temperature.

In some embodiments of the above methods, compositions or processes, the acid chloride may be pivaloyl chloride. In a further embodiment, the first base may be trimethylamine (TEA), 4-dimethylaminopyridine (DMAP) or pyridine. In a further embodiment, the protection reaction may comprise 1 eq. compound 3, 1.2-2.0 eq. acid chloride, 6 vol. of dichloromethane (DCM), and 1.5-6 eq. of the first base. In yet further embodiments, the acid chloride may be pivaloyl chloride, the first base may be pyridine, and the protection reaction may comprise 1.2 eq. pivaloyl chloride, 1.5 eq. first base and 6 vol. of DCM.

In some embodiments of the above methods, compositions or processes, the second allylic oxidation may comprise 1 eq. compound 4, 0.05-0.5 eq. $CrO_3$, 3.15-7 eq. tert-butyl hydroperoxide (TBHP), and 14.6-16 vol. of the first solvent. In further embodiments, the first solvent may be acetonitrile (ACN) or DCM. In yet further embodiments, the second allylic oxidation may comprise 0.5 eq. $CrO_3$, 3.15 eq. TBHP, 14.6 vol. of first solvent and the second allylic oxidation may occur at an initial temperature of 0° C. and a final temperature of room temperature, and the first solvent may be ACN. In some embodiments, the second allylic oxidation may comprise 0.05 eq. $CrO_3$, 7 eq. TBHP, and 16 vol. of solvent, the second allylic oxidation may occur at room temperature, and the solvent may be DCM.

In some embodiments of the above methods, compositions or processes, the reduction reaction may comprise 1 eq. of compound 5, 1.05-1.32 eq. of sodium borohydride ($NaBH_4$) and 10-18 vol. of ethanol (EtOH) and may be conducted at room temperature. In further embodiments, the reduction reaction may comprise 1.1 eq. of $NaBH_4$, 10 vol. of EtOH and may be conducted at room temperature over a period of 30 minutes.

In another embodiment of the above methods, compositions or processes, the acid may be para-toluenesulfonic acid (pTSA) or $MeSO_3H$. In further embodiments, the acid-catalyzed coupling reaction may comprise 1.02-1.1 eq. of compound 1, 0.05-0.28 eq. of pTSA, 35-112 vol. of DCM, and 1 eq. of the compound of formula 2. In further embodiments, the acid-catalyzed coupling reaction may comprise 1.02 eq. of compound 1, 0.1 eq. of pTSA, 35 vol. of DCM, and 1 eq. of the compound of formula 2. In yet further embodiments, the acid-catalyzed coupling reaction may comprise 0.05-0.2 eq. of $MeSO_3H$, 1.02 eq. of compound 1, 112 vol. of DCM and 1 eq. of the compound of formula 2. In some embodiments, the acid-catalyzed coupling reaction may comprise 0.2 eq. of $MeSO_3H$, 1.02 eq. of compound 1, 112 vol. of DCM and 1 eq. of the compound of formula 2.

In some embodiments of the above methods, compositions or processes, the methylation reaction may comprise 1 eq. of enantiomerically purified compound 6, 2.5-5 eq. dimethyl sulfate ($Me_2SO_4$), 5.3-6.7 eq. of potassium carbonate ($K_2CO_3$) and 5-20 vol. of acetone and may be conducted at room temperature. In further embodiments, the methylation reaction may comprise 4 eq. of $Me_2SO_4$, 5.3 eq. of $K_2CO_3$, 20 vol. of acetone, and may be conducted at room temperature over a period of 72 hours.

In some embodiments of the above methods, compositions, or processes, the deprotection reaction may comprise 1 eq. of enantiomerically purified compound 7, 2-9 eq. of the second base and 20-155 vol. of the second solvent. In further embodiments, the second base may be 2.4 eq. of lithium aluminum hydride ($LiAlH_4$) and the second solvent may be 75-155 vol. of tetrahydrofuran (THF). In some embodiments, second base may be 6 eq. of potassium tert-butoxide, the second solvent may be 88 vol. of methyl tert-butyl ester (MTBE) and the deprotection reaction may further comprise 1.6 eq. of water. In some embodiments, the second base may be 2-9 eq. of potassium hydroxide, the second solvent may be 80 vol. of methanol and the deprotection reaction may further comprise 1 mL of water. In some embodiments, the second base may be 6-9 eq. of sodium methoxide, the second solvent may be 20-88 vol. of methanol and the deprotection reaction may further comprise 1.6-22 eq. of water. In some embodiments, the second base may be 9 eq. of sodium methoxide, the second solvent may be 20 vol. of methanol, the deprotection reaction may further comprise 22 eq. of water and is conducted at a temperature of 37° C.

In some embodiments of the above methods, compositions, or processes, the coupling reaction may comprise 1 eq. of the first mixture, 2.2 eq. of Boc-alanine, 2.2 eq. of DCC, 0.1 eq. of DMAP and the reaction may occur at room temperature for 1 h.

In some embodiments of the above methods, compositions, or processes, purifying the second mixture may comprise silica gel column chromatography. In further embodiments, silica gel column chromatography may be conducted with a solvent gradient of 5-14% ethyl acetate in hexanes.

In some embodiments of the above methods, compositions, or processes, the hydrolysis reaction may comprise 1 eq. enantiomerically purified compound 10, 3-20 eq. of a third base and 10-20 eq. of the third solvent. In further embodiments, the third base may be 3 eq. of sodium hydroxide (NaOH), the third solvent may be 11 vol. of ethanol:water (1:1) and the hydrolysis reaction may occur over 2 hours.

Disclosed herein are methods, processes and compositions for enantioselectively producing a compound of formula 8, the method or process comprising: performing a coupling reaction with 1 eq. of a first mixture of a compound of formula 6, and a compound of formula 17, with 2.2 eq. of Boc-alanine, 2.2 eq. of N,N'-dicyclohexylcarbodiimide (DCC), and 0.1 eq. of 4-dimethylaminopyridine (DMAP) to yield a second mixture of compound 10 and a compound of formula 11, purifying the second mixture by silica gel column chromatography with a solvent gradient of 5-14% ethyl acetate in hexanes to yield enantiomerically purified compound 10, performing a hydrolysis reaction comprising 1 eq. enantiomerically purified compound 10, 3-20 eq. of a third base and 10-20 eq. of solvent, to yield enantiomerically purified compound 6, performing a methylation reaction comprising 1 eq. of enantiomerically purified compound 6, 2.5-5 eq. dimethyl sulfate (Me$_2$SO$_4$), 5.3-6.7 eq. of potassium carbonate (K$_2$CO$_3$) and 5-20 vol. of acetone to yield an enantiomerically purified compound of formula 7, performing a deprotection reaction comprising 1 eq. of compound 7, 2-9 equivalents of a second base and 20-155 vol. of a second solvent to yield the enantiomerically purified compound 8; and isolating the enantiomerically purified compound 8.

Disclosed herein are methods, processes and compositions for enantioselectively producing a compound of formula 18:

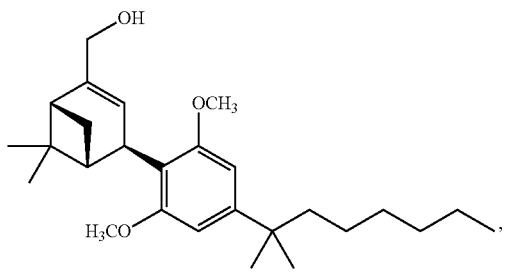

(18)

the method or process comprising: performing a coupling reaction with 1 eq. of a first mixture of a compound formula 6 and a compound of formula 17, with 2.2 eq. of Boc-alanine, 2.2 eq. of N,N'-dicyclohexylcarbodiimide (DCC), and 0.1 eq. of 4-dimethylaminopyridine (DMAP) to yield a second mixture of compound 10 and a compound of formula 11, purifying the mixture by silica gel column chromatography with a solvent gradient of 5-14% ethyl acetate in hexanes to yield enantiomerically purified compound 11, performing a hydrolysis reaction comprising 1 eq. enantiomerically purified compound 11, 3-20 eq. of a third base and 10-20 eq. of solvent, to yield enantiomerically purified compound 17, performing a methylation reaction comprising 1 eq. of enantiomerically purified compound 17, 2.5-5 eq. dimethyl sulfate (Me$_2$SO$_4$), 5.3-6.7 eq. of potassium carbonate (K$_2$CO$_3$) and 5-20 vol. of acetone to yield an enantiomerically purified compound of formula 19:

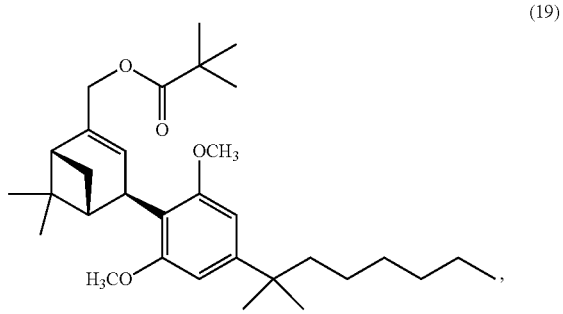 [SMILES: CCCCCCC(C)(C)c1cc(OC)c([C@@H]2C=C(COC(=O)C(C)(C)C)[C@@H]3C[C@H]2C3(C)C)c(OC)c1]

(19)

performing a deprotection reaction comprising 1 eq. of enantiomerically purified compound 19, 2-9 equivalents of a second base and 20-155 vol. of a second solvent to yield the enantiomerically purified compound 18; and isolating the enantiomerically purified compound 18.

According to the present invention there is provided methods, processes and compositions for preparing a compound of formula 18:

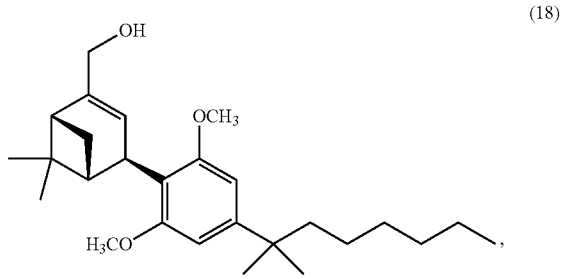 [SMILES: CCCCCCC(C)(C)c1cc(OC)c([C@@H]2C=C(CO)[C@@H]3C[C@H]2C3(C)C)c(OC)c1]

(18)

the method or process comprising: providing a first reactant of formula 20:

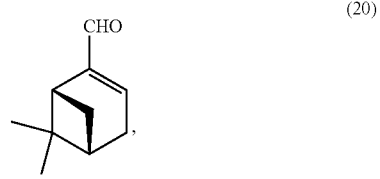

(20)

performing a first reduction reaction comprising compound 20, and a reducing agent such as NaBH$_4$, to yield a compound of formula 21:

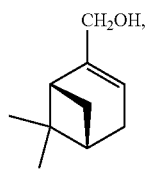   (21)

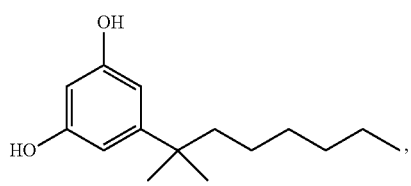

to yield a compound of formula 17:

performing a protection reaction comprising compound 21, an acid halide such as an acid chloride, a solvent such as dichloromethane (DCM), and a first base to yield a compound of formula 22:

(17)

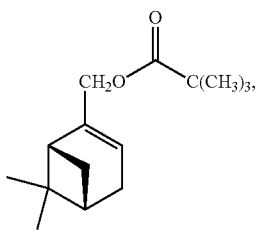   (22)

performing a methylation reaction comprising compound 17, dimethyl sulfate (Me$_2$SO$_4$), and potassium carbonate (K$_2$CO$_3$) to yield a compound of formula 19:

(19)

performing a second allylic oxidation comprising compound 22, an oxidant such as CrO$_3$, a peroxide such as tert-butyl hydroperoxide (TBHP), and a first solvent to yield a compound of formula 23:

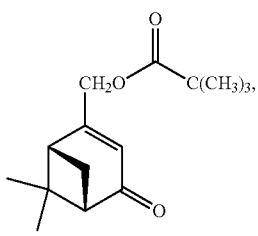   (23)

performing a deprotection reaction comprising a second base and a second solvent to yield the compound of formula 18, and isolating the compound of formula 18.

Disclosed herein are compounds and compositions of formula 10:

performing a second reduction reaction comprising compound 23, a reducing agent such as sodium borohydride (NaBH$_4$), and a solvent, such as ethanol, to yield a compound of formula 24:

(10)

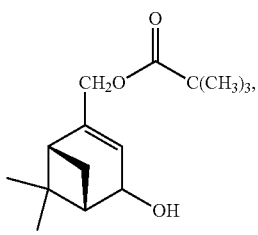   (24)

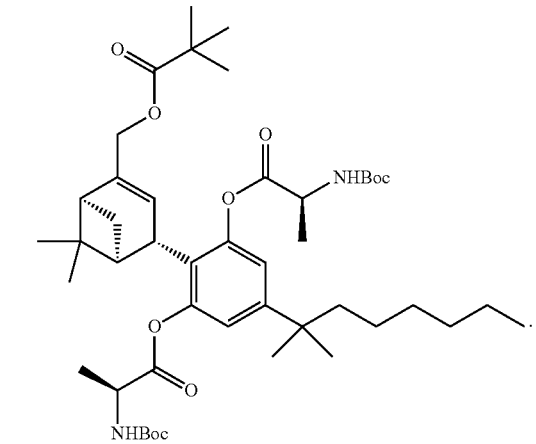

performing an acid-catalyzed coupling reaction comprising compound 24, an acid, DCM, and a compound of formula 2:

Disclosed herein are compounds and compositions of formula 11:

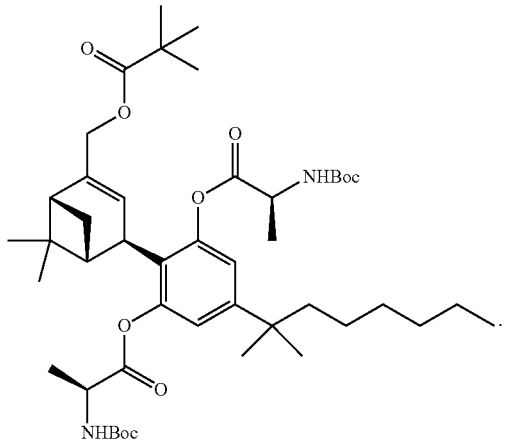

(11)

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 10 is a certificate of analysis of HU308 (compound 8);

FIG. 16 is an HPLC chromatogram of Int. 6 after chiral resolution;

FIGS. 23A-H are spectra of Int. 6 after chiral resolution. FIG. 23A is a certificate of analysis of Int. 6; FIG. 23B is an $^1$H-NMR spectrum of Int. 6; FIG. 23C is a $^{13}$C-NMR spectrum of Int. 6; FIG. 23D is an ESI-MS spectrum of Int. 6, FIGS. 23E-G are HPLC chromatograms of Int. 6, and FIG. 23H is an FT-IR spectrum of Int. 6;

FIG. 24A-G are spectra of compound 8 (HU308) after chiral resolution.

FIG. 24A is a certificate of analysis of compound 8; FIG. 24B is an $^1$H-NMR spectrum of compound 8; FIG. 24C is a $^{13}$C-NMR spectrum of compound 8; FIG. 24D is an ESI-MS spectrum of compound 8, FIG. 24E is an FT-IR spectrum of compound 8; FIGS. 24F-G are HPLC chromatograms of compound 8, FIG. 25 depicts chiral purity data of compound 8 (HU308) and compound 18 (HU433) obtained after chiral resolution and subsequent hydrolysis and methylation steps;

FIGS. 26A-H are spectra of compound 18 that was synthesized using the synthetic procedure shown in FIG. 22. Compound 18 was synthesized using the synthetic route depicted in FIG. 22. FIG. 26A is a certificate of analysis of compound 18; FIG. 26B depicts chiral purity data of compound 18; FIG. 26C is an $^1$H-NMR spectrum of compound 18; FIG. 26D is a $^{13}$C-NMR spectrum of compound 18; FIG. 26E is an ESI-MS spectrum of compound 18; FIG. 26F is an FT-IR spectrum of compound 18; FIGS. 26G and 26H depict HPLC chromatograms of compound 18.

FIG. 29 is a chiral resolution scheme for enantiomeric mixture resolution to HU308 Intermediate 6a.

DETAILED DESCRIPTION

Figure 1:
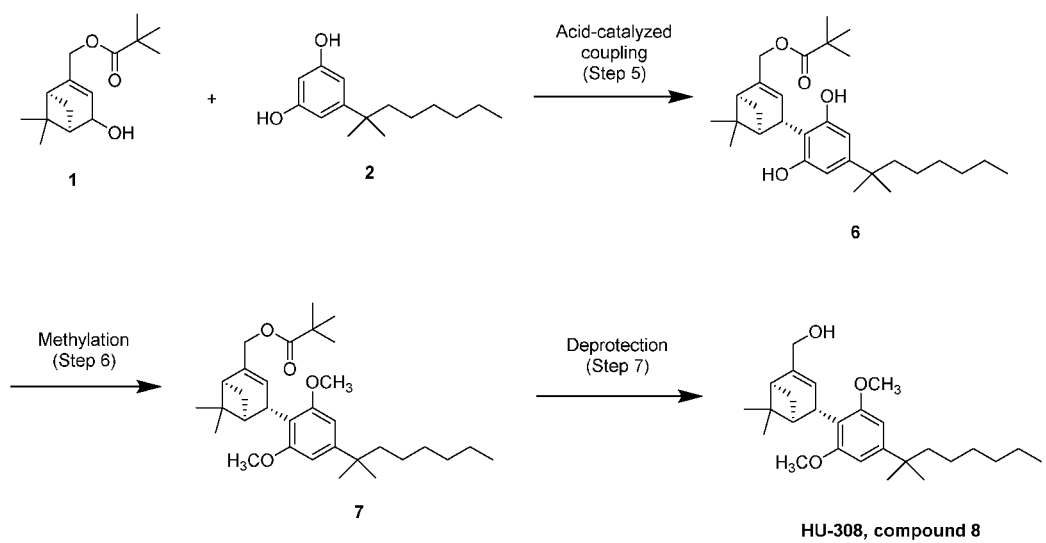
FIG. 1 is a synthetic scheme showing the synthesis of HU308 (compound 8) from Int. 1.

One or more illustrative embodiments have been described by way of example. Described herein are compositions and methods relating to producing HU308 and HU433. It will be appreciated that embodiments and examples are provided for illustrative purposes intended for those skilled in the art, and are not meant to be limiting in any way. All references to embodiments, examples, aspects, formulas, compounds, compositions, solutions, kits and the like are intended to be illustrative and non-limiting.

It must be noted that, as used in this specification and the appended claims, the singular forms "a", "an" and "the" include plural referents unless the content clearly dictates otherwise. Thus, for example, reference to "a compound having a formula 8" may include a plurality of compounds, and the like.

As will be understood by a person of skill in the art, the term "Chiral" or "chiral center" is used to refer to a carbon atom having four different substituents. One criterion of chirality is non-superimposability of mirror images.

As will be understood by a person of skill in the art, the term "Enantiomeric mixture" refers to a chiral compound having a mixture of enantiomers, including a racemic mixture. In some cases, enantiomeric mixture refers to a chiral compound having a substantially equal amount of each enantiomers, such as a racemic mixture. In some cases, enantiomeric mixture refers to a mixture where one of the enantiomers is present in a greater amount.

"Enantiomeric excess" or "% ee" refers to the amount of difference between the first enantiomer and the second enantiomer. Enantiomeric excess is defined by the equation: % ee=(% of the first enantiomer)–(% of the second enantiomer). Thus, if a composition comprises 98% of the first enantiomer and 2% of the second enantiomer, the enantiomeric excess of the first enantiomer is 98%-2% or 96%.

"Optical purity" refers to the amount of a particular enantiomer present in the composition. For example, if a composition comprises 98% of the first enantiomer and 2% of the second enantiomer, the optical purity of the first enantiomer is 98%.

"Protecting group" refers to a moiety that when attached to a reactive group in a molecule masks, reduces or prevents that group's reactivity. Examples of protecting groups can be found in T. W. Greene and P. G. M. Wuts, *Protective Groups in Organic Synthesis,* $3^{rd}$ edition, John Wiley & Sons, New York, 1999, and Harrison and Harrison et al., *Compendium of Synthetic Organic Methods,* Vols. 1-8 (John Wiley and Sons, 1971-1996), which are incorporated herein by reference in their entirety. Representative hydroxyl protecting groups include, but are not limited to, acyl groups, benzyl and trityl ethers, tetrahydropyranyl ethers, trialkylsilyl ethers, allyl ethers or others known in the art. Representative amino protecting groups include: formyl, acetyl, trifluoroacetyl, benzyl, benzyloxycarbonyl (CBZ), tert-butoxycarbonyl (Boc), trimethyl silyl (TMS), 2-trimethylsilyl-ethane-sulfonyl (SES), trityl and substituted trityl groups, allyloxycarbonyl, 9-fluorenylmethyloxycarbonyl (FMOC), nitro-veratryloxycarbonyl (NVOC), or others known in the art.

As used herein, the term "treating", "contacting", "performing" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. Additional routine steps, such as work-up, liquid-liquid extractions, or others, may be employed.

As used herein, the terms "isolating" or "purifying" may be used interchangeably and refer to methods or reagents known in the art to isolating a substance (such as a compound or mixture of one or more compounds) such that the substance comprises the majority percent of the sample in which it resides. Typically in a sample, a substantially purified component comprises 50%, preferably 80%-85%, more preferably 90-95% of the sample. Techniques for purifying compounds of interest are well known in the art and include, for example, normal-phase or reversed-phase chromatography, chiral chromatography, hydrophobic interaction chromatography, recrystallization, extraction, sedimentation according to density, high performance liquid chromatography or others. Isolation or purification could occur prior, after or in-between any step described herein.

Many organic compounds exist in optically active forms, i.e., they have the ability to rotate the plane of plane-polarized light. In describing an optically active compound, the prefixes R and S are used to denote the absolute configuration of the molecule about its chiral center(s). The prefixes "d" and "l" or (+) and (–) are employed to designate the sign of rotation of plane-polarized light by the compound, with (–) or (l) meaning that the compound is "levorotatory" and with (+) or (d) is meaning that the compound is "dextrorotatory". There is no correlation between nomenclature for the absolute stereochemistry and for the rotation of an enantiomer. For a given chemical structure, these compounds, called "enantiomers," are identical except that they are mirror images of one another. A specific stereoisomer can also be referred to as an "enantiomer," and a mixture of such isomers is often called an "enantiomeric" or "racemic" mixture. Diastereomers will be understood as non-superimposable stereoisomers. See, e.g., Streitwiesser, A. & Heathcock, C. H., INTRODUCTION TO ORGANIC CHEMISTRY, $2^{nd}$ Edition, Chapter 7 (MacMillan Publishing Co., U.S.A. 1981), herein incorporated by reference.

The terms "substantially free of its stereoisomer", "substantially free of its enantiomer", and "enantiomerically pure" are used interchangeably herein and mean that the compositions contain a greater proportion of a desired isomer in relation to a one or more undesired isomers. For example, the term "enantiomerically pure" or "enantiomerically purified" means that the composition is 510% or greater of the desired isomer, such as 70%, 80%, 90% or greater. In a preferred embodiment, at least 90% by weight of the desired isomer and 10% by weight or less of the undesired isomer or isomers. In a more preferred embodiment, the term "enantiomerically pure" or "enantiomerically purified" means that the composition contains at least 99% by weight of the desired isomer and 1% by weight or less of the undesired isomer or isomers. In the most preferred embodiment, the term "enantiomerically pure" or "enantiomerically purified" means that the composition contains greater than 99% by weight of the desired isomer. These percentages are based upon the total amount of isomers in the composition.

The term eq. and equiv. are used interchangeably, and a person of skill in the art will understand that the term is meant to describe the relative amounts of reagent used, compared to one reagent set at 1 equiv. The terms are used herein to describe mole equivalents. For example if a reaction described reagent A is 1 equiv. and reagent B is 2 equiv., then twice as many mol. of reagent B as reagent A should be used. When ranges of equivalents are used, any value therebetween (optionally rounded to the nearest 0.1), or any subrange spanning between any two of these values are contemplated.

The term vol. is used herein to describe the amount of solvent used in a reaction. As will be understood by a person of skill in the art, vol. is a term used in process chemistry and means that 1 mL of solvent should be used per g of limiting reagent. For example, if a reaction described 40 vol., then 40 mL of solvent should be used per gram of limiting reagent. When ranges of vol. are used, any value therebetween (optionally rounded to the nearest 0.1), or any subrange spanning between any two of these values are contemplated.

A person of skill in the art will understood that solvents used and described in the methods, processes and compositions herein may be varied without departing from the scope of the invention. For example, in embodiments where DCM is used, chloroform or carbon tetrachloride may be substituted, either wholly or partially.

The term "room temperature" will be understood by a person of skill in the art to refer to ambient temperature, for example preferably 10-35° C. any value therebetween (optionally rounded to the nearest 0.1), or any subrange spanning between any two of these values. In some cases, room temperature is 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., or others. The temperature range may also include temperatures outside the range listed.

Methods, processes and compositions as described herein may be used to produce HU308 and/or HU433 at a suitable scale. Scaling up production can be difficult in the field and a person of skill will understand that what works well for bench-size production scale may not work well when scaled up. Accordingly, the methods and compositions as described herein and throughout may be employed to produce the compounds in scaled up amounts. In one embodiment, the methods and compositions herein may be employed to produce compounds on the kg or greater scale. In further embodiments, the compositions and methods as described herein may be used to produce compounds on the gram scale, for example, but not limited to 1, 2, 5, 10, 15, 20, 25, 30, 35, 40, 45, 50, 55, 60, 65, 70, 75, 80, 85, 90, 95, 100, 200, 250, 300, 400, 450, 500, 550, 600, 700, 750, 800, 900 or more. Further, the methods and compositions described herein may be employed to produce a scaled up range of compounds in an amount, for example, but not limited to, 1-10 g, 10-15 g, 10-20 g, 10-50 g, 60-70 g, or any other range defined by any two values noted above or any values therein between.

Optimization of Methodology for Production of HU308 (8) and HU433 (18)

Figure 2:
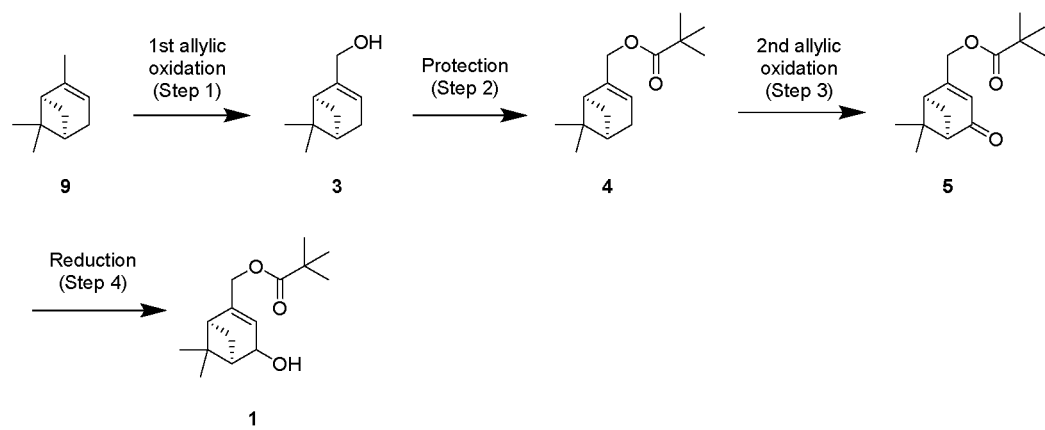
FIG. 2 is a synthetic scheme showing the synthesis of Int. 1 from α-(+)-pinene (compound 9)

Referring to FIGS. 1 and 2, described herein are methods, processes and compositions for producing a compound of formula 8:

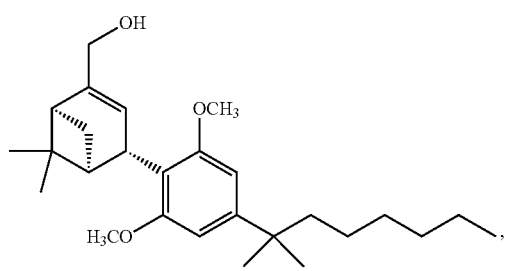
(8)

the method comprising:
providing a first reactant of formula 9:

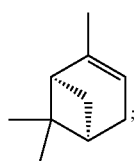
(9)

performing a first allylic oxidation comprising compound 9, an oxidant such as SeO$_2$, and peroxide to yield a compound of formula 3:

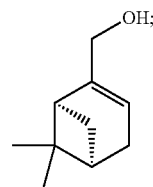
(3)

performing a protection reaction comprising compound 3, acid chloride, a solvent such as dichloromethane (DCM), and a first base to yield a compound of formula 4:

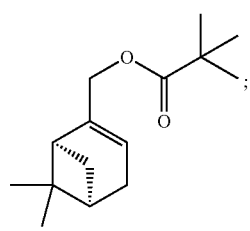
(4)

performing a second allylic oxidation comprising compound 4, an oxidant such as CrO$_3$, a peroxide such as tert-butyl hydroperoxide (TBHP), and a first solvent to yield a compound of formula 5:

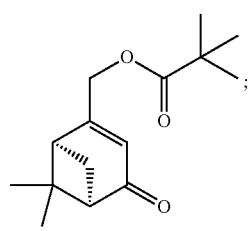
(5)

performing a reduction reaction comprising compound 5, and a reducing agent such as sodium borohydride (NaBH$_4$), to yield a compound of formula 1:

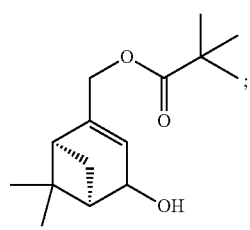
(1)

performing an acid-catalyzed coupling reaction comprising compound 1, an acid, DCM, and a compound of formula 2:

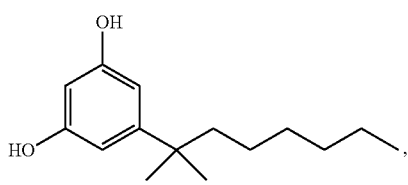
(2)

to yield a compound of formula 6:

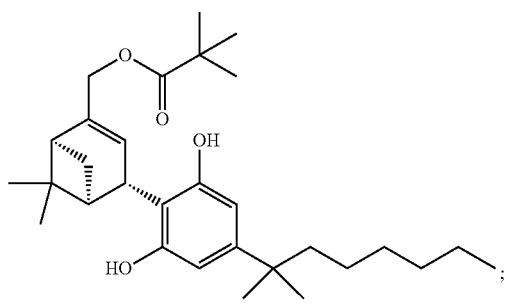
(6)

performing a methylation reaction comprising compound 6, dimethyl sulfate (Me$_2$SO$_4$), potassium carbonate (K$_2$CO$_3$) and acetone to yield a compound of formula 7:

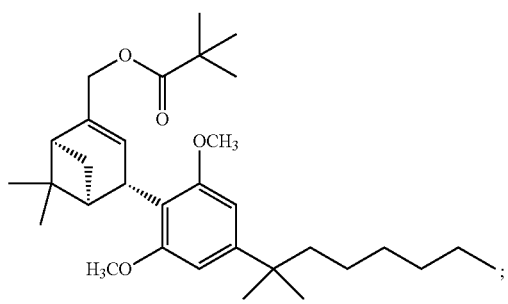
(7)

performing a deprotection reaction comprising a second base and a second solvent to yield the compound of formula 8; and isolating the compound of formula 8.

Also provided, as described above, are compositions comprising components and mixtures that are useful in the methods and processes described herein, for example, but not wishing to be limiting, a compound of formula 9 with one or both of a peroxide and SeO$_2$; a compound of formula 9 with at least one, two or three of an acid chloride, dichloromethane and a base, a compound of formula 4 with one or two of CrO$_3$, TBHT or both, a compound of formula 5 with sodium borohydride, a compound of formula 1 in combination with p-toluenesulfonic acid (pTSA), dichloromethane, a compound of formula 2 or any combination thereof, a compound of formula 6 with one or more of dimethyl sulfate, potassium carbonate, acetone, or a combination thereof. These examples are not meant to be limiting or exhaustive.

In a first step of the method, a first allylic oxidation is performed. In the oxidation step, a compound of formula 9:

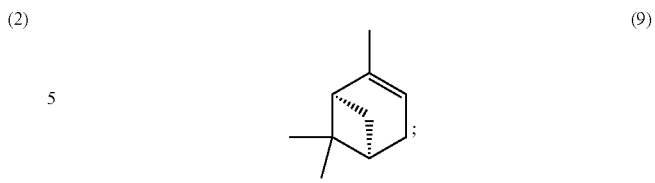
(9)

is mixed with an oxidant, such as SeO$_2$, and a peroxide to yield an oxidized intermediate. The intermediate may be reduced with NaBH$_4$ to yield a compound of formula 3:

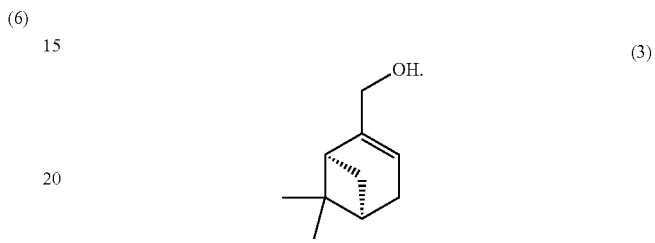
(3)

In some cases, sub-stoichiometric or stoichiometric quantities of SeO$_2$ is used. For example, about 0.02-1.19 eq. SeO$_2$ or any value therebetween (optionally rounded to the nearest 0.1), or any subrange spanning between any two of these values, such as 0.01-200 eq may be used. For example, 0.01, 0.015, 0.02, 0.025, 0.03, 0.036, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55 eq. of SeO$_2$ or others are considered.

The peroxide may be a suitable peroxide known in the art, for example, tert-butyl hydroperoxide (TBHP). TBHP may be used as an aqueous solution with a suitable concentration, such as 70 wt. %. Prior to addition to SeO$_2$, the TBHP may be extracted into a suitable organic solvent, such as DCM, and the aqueous layer may be discarded.

In some cases, about 0-3.5 eq. or any value therebetween (optionally rounded to the nearest 0.1), or any subrange spanning between any two of these values, such as 0.01-200 eq. of peroxide may be used. For example, 0.01, 0.015, 0.02, 0.025, 0.03, 0.036, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95 and 4 eq. of peroxide or others are considered.

In an embodiment, 1.19 eq. of SeO$_2$ and no peroxide is used and the reaction is conducted at 80° C. In another embodiment, 1.02 eq. of SeO$_2$ and 1.51 eq. of formic acid (HCOOH) is used and the reaction is heated to 60° C. In another embodiment, 0.036 eq. of SeO$_2$ and 3.5 eq. of TBHP is used and the reaction is conducted at room temperature.

The reaction may be conducted at a suitable temperature, such as room temperature. After the allylic oxidation, the resulting oxidized intermediate may be directly reduced to the primary alcohol by a suitable reducing agent. For example, in an embodiment, sodium borohydride may be used directly without the need for substantial purification. In other embodiments, a purification step may be desired or required. For example, the crude oxidized intermediate may be subjected to liquid-liquid extraction. In an embodiment, 0.45 eq. of NaBH$_4$ is used. In a preferred embodiment, the first allylic oxidation comprises 0.036 eq. SeO$_2$, 2.0 eq. TBHP, 0.45 eq. NaBH$_4$, and is conducted at room temperature.

In some cases, about 0.1-20 eq. or any value therebetween (optionally rounded to the nearest 0.1), or any subrange spanning between any two of these values, such as 0.01-2 eq. of reducing agent may be used. For example, 0.01, 0.015, 0.02, 0.025, 0.03, 0.036, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 5, 6, 7, 8, 9, 10, 11, 12, 13, 14, 15, 16, 17, 18, 19, and 20 eq. of reducing agent and others are considered.

After the first allylic oxidation reaction is complete, crude intermediate 3 may then be subjected to known work-up methods known in the art. In some embodiments, the reaction mixture is cooled down to a low temperature, such as 9-13° C. and quenched by the addition of 10% HCl to a final pH of about 4. The quenched reaction may then be subjected to liquid-liquid extraction with the addition of organic solvent, such as diethyl ether or tert-butyl methyl ether (MTBE). The organic layers may then be pooled before drying with an anhydrous drying agent. Suitable purification methods known in the art may then be performed, such as silica gel column chromatography. In an embodiment, the organic layers are pooled, dried and the crude product is purified through a silica gel bed. Compound 3 may be eluted from the gel bed with a suitable solvent, which may be a gradient or isocratic. For example, ethyl acetate in hexanes may be used with a gradient of 0, 2.5, 5, 7.5, 10, 12.5 and 15%.

Figure 22:
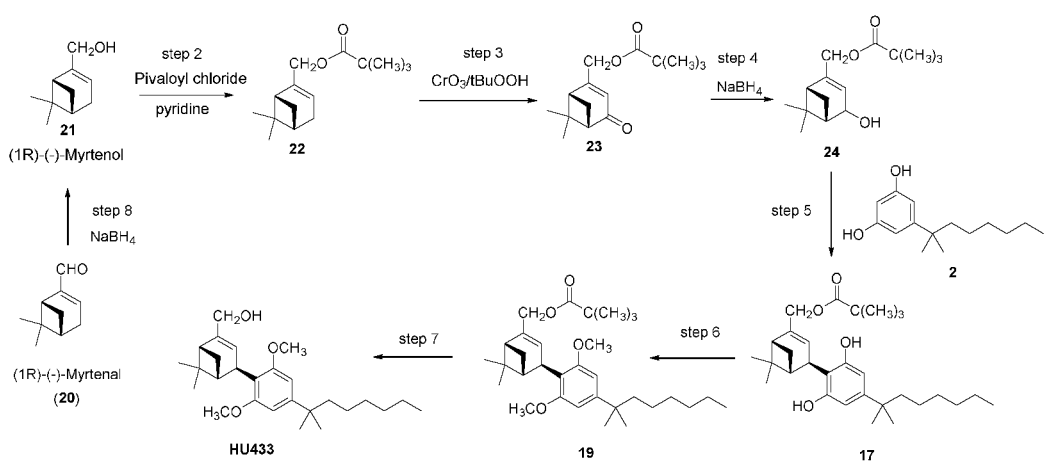
FIG. 22 is a synthetic scheme depicting the synthesis of HU433 from (1R)-(−)-Myrtenal.
Figure 23A:
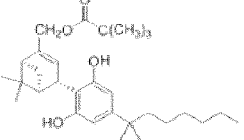
Figure 23B:
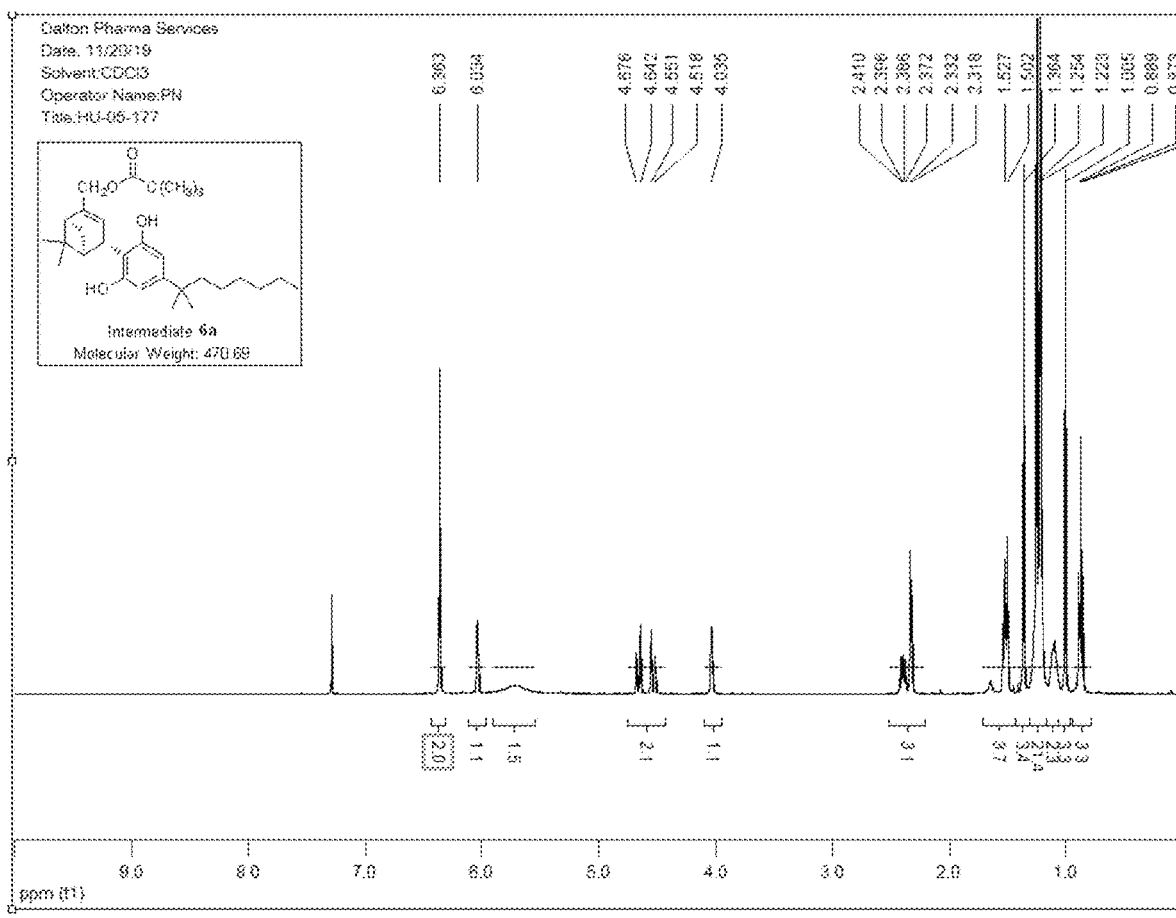
Figure 23C:
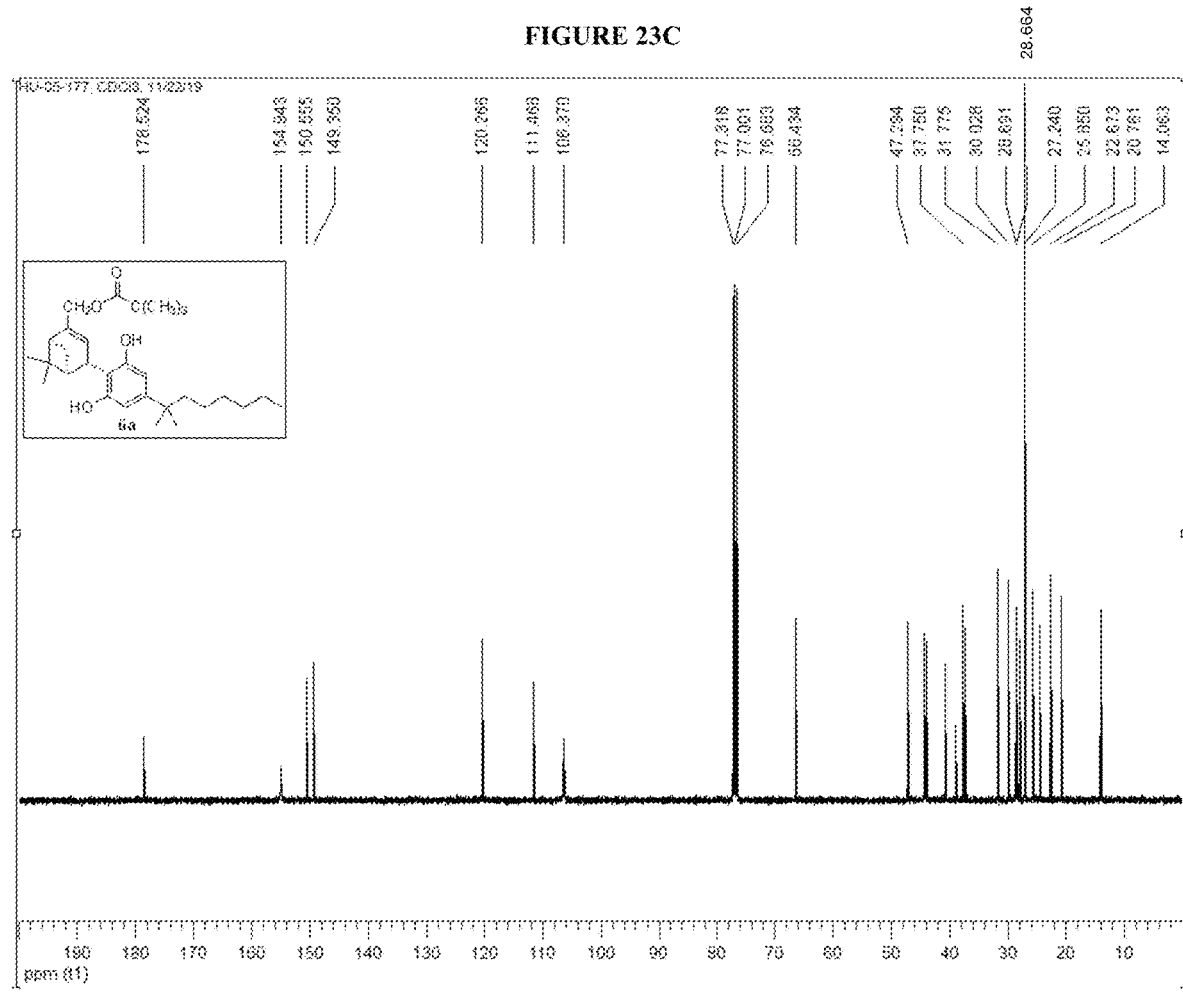
Figure 23D:
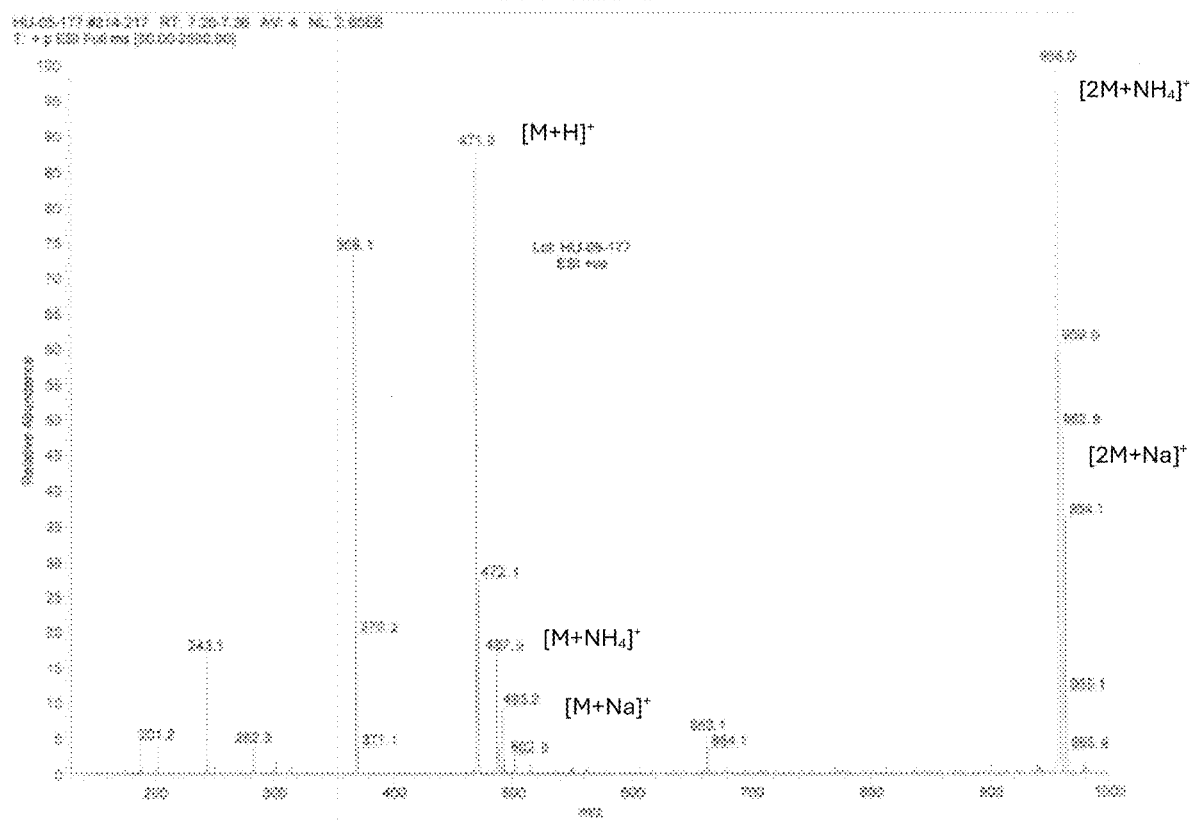
Figure 23F:
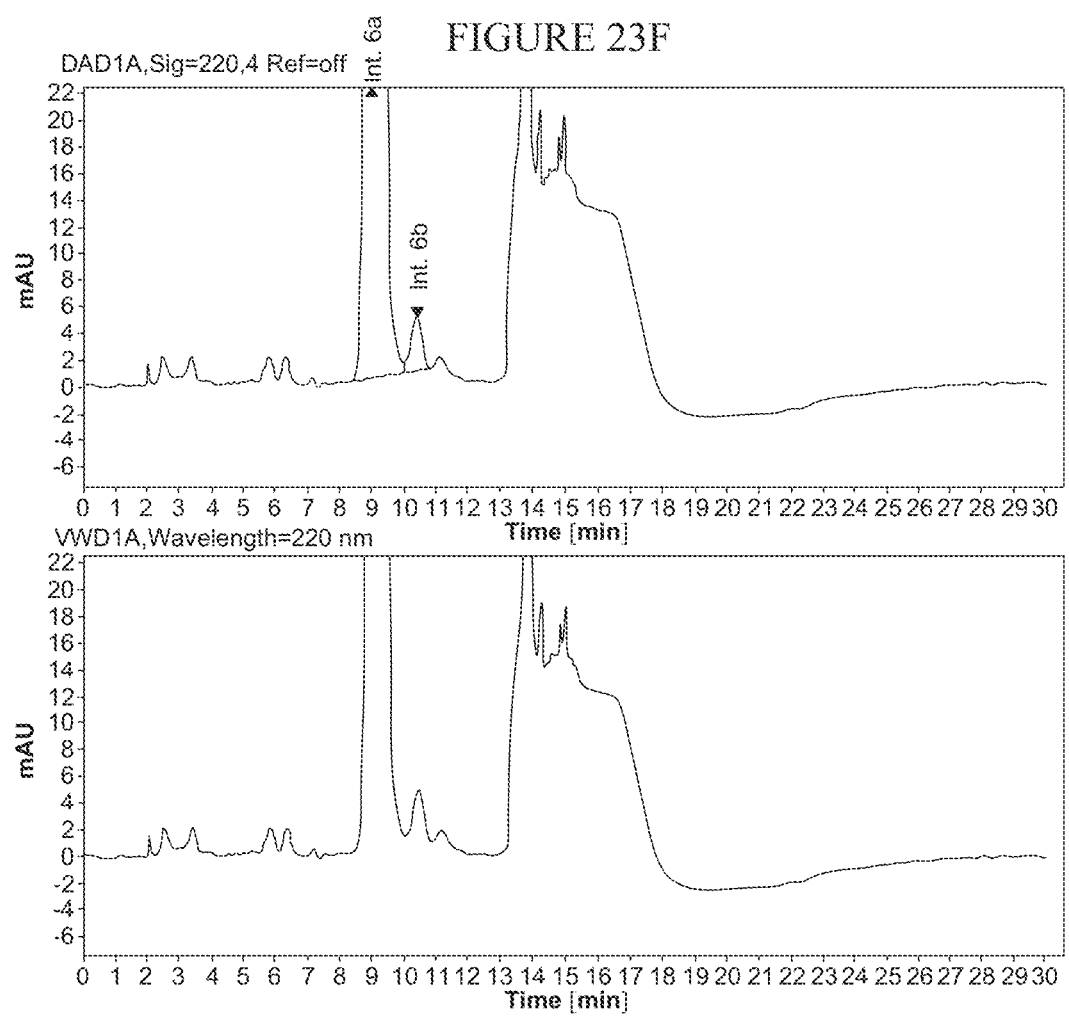
Figure 24B:
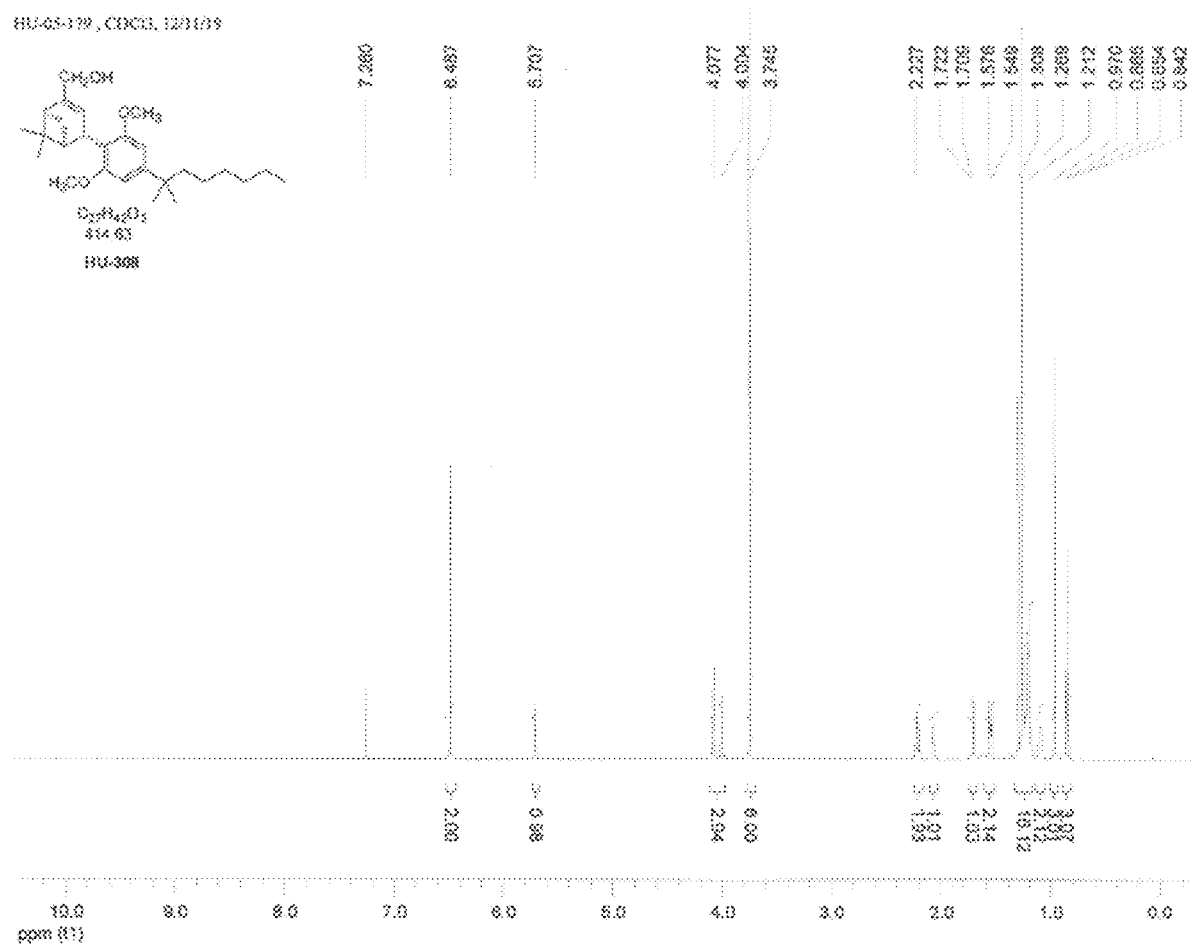
Figure 24C:
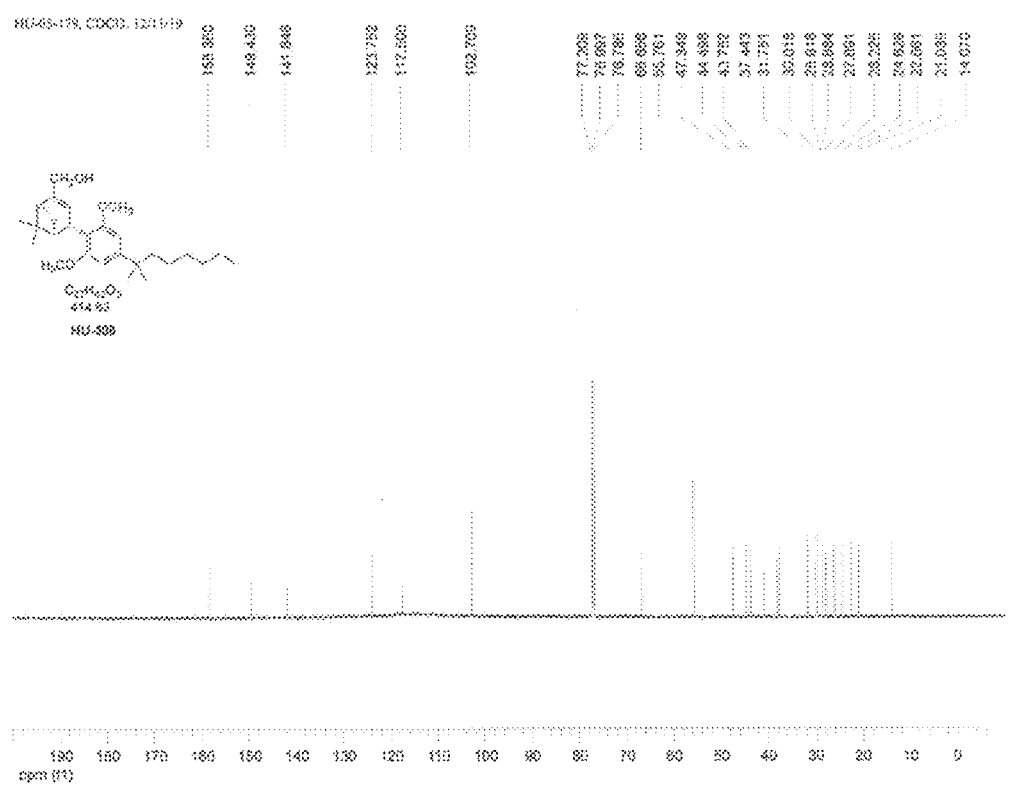
Figure 24D:
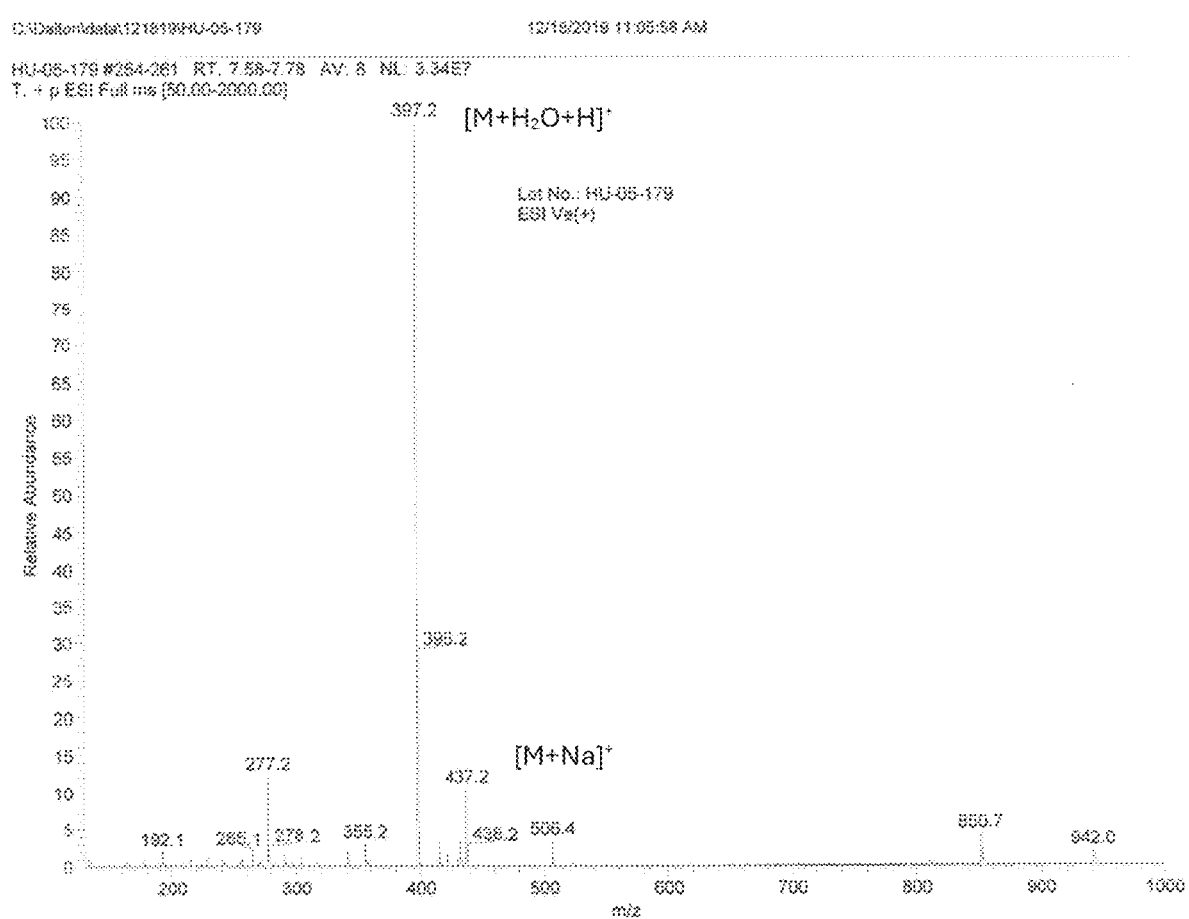
Figure 24E:
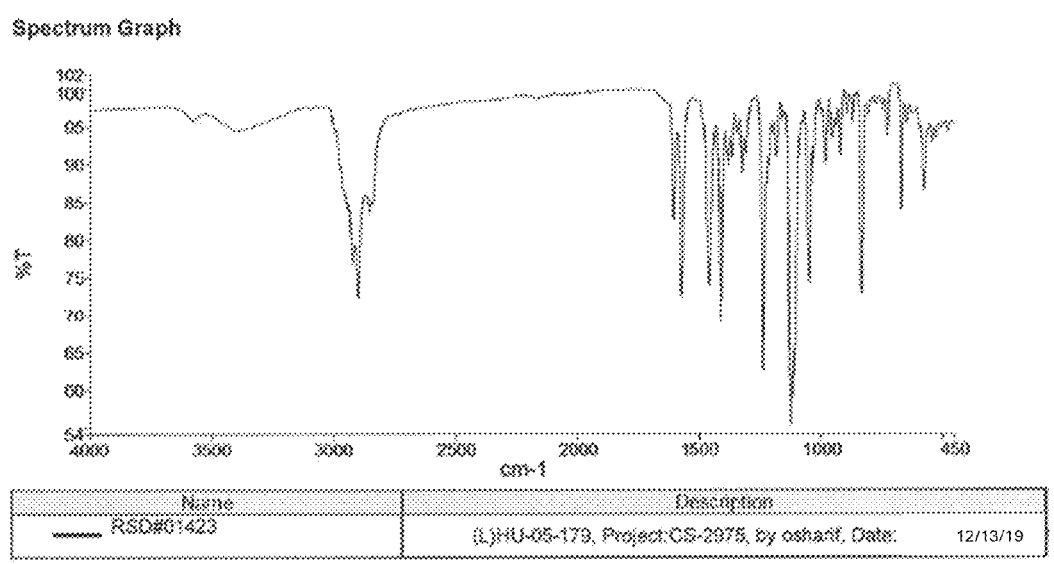

The oxidized intermediate described above may be (1S)-(+)-Myrtenal or (1R)-(−)-Myrtenal. It will be understood by a person of skill in the art that the synthesis of HU308 may start from this intermediate instead of α-pinene. In such an embodiment, the first step may be a reduction of the aldehyde group to a primary alcohol via a reduction agent such as NaBH$_4$. The remaining steps 2-7 would then proceed as described herein. A synthetic scheme for such embodiments is shown in FIG. 22 with (1R)-(−)-Myrtenal as the starting material.

In a second step, protection of the primary alcohol of compound 3 is performed. The primary alcohol of intermediate 3 may be protected by a suitable protecting group. For example, but not to be considered limiting in any manner, compound 3 may be mixed with an acid chloride and a first base in suitable conditions to yield compound 4:

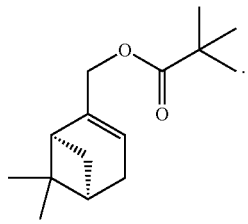

(4)

In some embodiments, the protection reaction comprises 1 eq. compound 3, about 1.2-2.0 eq. acid chloride, about 6 vol. of a suitable solvent, such as dichloromethane (DCM), and about 1.5-11.4 eq. of a first base to yield a compound of formula 4. The protection reaction may comprise an additional base, such as 4-dimethylaminopyridine (DMAP). In some embodiments, catalytic DMAP may be used, for example 0.01 eq.

The acid chloride may be any suitable acid halide, such as benzoyl chloride, pivaloyl chloride, or others. For example, acid bromides, such as pivaloyl bromide, benzoyl bromide, or others, are contemplated.

The first base may be any suitable base known in the art, such as trimethylamine (TEA), DMAP, pyridine, Hunig's base or others. In a preferred embodiment, the acid chloride is pivaloyl chloride, the base is pyridine, and the protection reaction comprises 1.2 eq. pivaloyl chloride, 1.5 eq. base and 6 vol. of DCM. In this embodiment, the primary alcohol is protected by a pivaloyl protecting group (Piv), but other suitable protecting groups known in the art may be used, such as through an ether protecting group (methoxymethyl ether, tetrahydropyranyl ether, t-butyl ether, or others), a silyl protecting group (t-Butyldimethylsilyl ether, t-Butyldiphenylsilyl ether, or others) or other acetyl protecting groups (benzoic acid ester or others).

In an embodiment, the protection reaction comprises about 2.0 eq. trimethylacetyl chloride (acid chloride), about 11.4 eq. pyridine (first base) in anhydrous dichloromethane (DCM) at a starting temperature of 0° C. and a final temperature of room temperature. In some cases, the reaction occurs over a period of about 16 hours. In another embodiment, the protection reaction comprises about 2.0 eq. acid chloride, about 6 vol. DCM, and about 6 vol. of pyridine. In yet another embodiment, the protection reaction comprises about 1.2 eq. acid chloride, about 6 vol. DCM, and about 6 vol. of pyridine. In another embodiment, the protection reaction comprises about 2.0 eq. acid chloride, about 6 vol. DCM, 2.5 vol. of trimethylamine (TEA) and 0.01 eq. DMAP.

In some cases, about 0.1-20 eq. or any value therebetween (optionally rounded to the nearest 0.1), or any subrange spanning between any two of these values, such as 0.01-2 eq. of acid chloride may be used. For example, 0.01, 0.015, 0.02, 0.025, 0.03, 0.036, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 5, 6, 7, 8, 9, 10, 11, 12, 13, 14, 15, 16, 17, 18, 19, and 20 eq. of acid chloride or others are considered.

In some cases, about 0.01-150 vol. or any value therebetween (optionally rounded to the nearest 0.1), or any subrange spanning between any two of these values, such as 0.01-50 vol. of solvent may be used. For example, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 vol. of solvent or others are considered.

After the protection reaction is complete, crude intermediate 4 may then be subjected to known work-up methods known in the art. In some embodiments, the reaction mixture is diluted with MTBE, and quenched by the addition of 10% HCl. The aqueous/organic mixture may then be washed with saturated sodium bicarbonate solution and brine. The organic layers may then be dried with an anhydrous drying agent prior to filtration and concentration under vacuum. Suitable purification methods known in the art may then be performed, such as silica gel column chromatography. In an embodiment, the organic layers are pooled, dried and the crude product is purified through a silica gel bed. Compound 4 may be eluted from the gel bed with a suitable solvent, which may be a gradient or isocratic. For example, ethyl acetate in hexanes may be used with a gradient of 0 and 5%.

In a third step of the method, a second allylic oxidation is performed. Compound 4 may be subjected to oxidizing conditions with $CrO_3$ and a peroxide in a suitable solvent to yield a compound of formula 5:

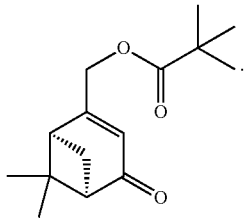

(5)

In some cases, sub-stoichiometric or catalytic amounts of $CrO_3$ is used. For example, about 0.05-0.5 eq. of $CrO_3$ may be used. The peroxide used in this reaction may be tert-butyl hydroperoxide (TBHP). In some cases, about 3.15-7 eq. of TBHP is used. The suitable solvent may be acetonitrile (ACN), dichloromethane (DCM), acetone or others. In some cases, $CrO_3$, DCM and TBHP are mixed prior to addition of compound 4. The reaction may occur over a suitable period, such as about 5 minutes to 16 hours.

In one embodiment, the second allylic oxidation comprises 0.5 eq. $CrO_3$, 3.15 eq. TBHP, 14.6 vol. of solvent and the second allylic oxidation occurs at an initial temperature of 0° C. and a final temperature of room temperature. In such an embodiment, the solvent is ACN. In another preferred embodiment, the second allylic oxidation comprises 0.05 eq. $CrO_3$, 7 eq. TBHP, 16 vol. of solvent and the second allylic oxidation occurs at room temperature. In such embodiments, the solvent is DCM. In an embodiment, about 0.53 eq. of $CrO_3$, 6.3 eq. TBHP and 14.6 vol. ACN may be used. In another embodiment, about 0.5 eq. of $CrO_3$, 5 eq. TBHP and 14.6 vol. ACN may be used and the reaction occurs at a temperature of 0° C. to room temperature (rt). In yet another embodiment, about 0.05 eq. of $CrO_3$, 7 eq. TBHP and 16 vol. ACN may be used and the reaction occurs at rt over a period of about 4 hours. In yet another embodiment, about 0.05 eq. of $CrO_3$, 7 eq. TBHP and 16 vol. DCM may be used and the reaction occurs at rt over a period of about 2.5 hours. In yet another embodiment, about 0.05 eq. of $CrO_3$, 5 eq. TBHP and 16 vol. DCM may be used and the reaction occurs at rt over a period of about 2.5 hours. In yet another embodiment, about 0.05 eq. of $CrO_3$, 7 eq. TBHP and 16 vol. DCM may be used and the reaction occurs at rt over a period of about 1.5 hours. In yet another embodiment, about 0.05 eq. of $CrO_3$, 7 eq. TBHP and 16 vol. DCM may be used and the reaction occurs at rt over a period of about 4 hours.

The second allylic reaction may occur at a suitable temperature. In some cases, the reaction occurs at a cooler temperature, such as 0° C. In some cases, the temperature is allowed to increase to ambient temperature. In other cases, the temperature is maintained at ambient temperature throughout.

In some cases, intermediate 5 is purified after the second allylic oxidation is completed. In such cases, the crude intermediate 5 may be subjected to work-up methods known in the art. In some embodiments, the reaction mixture is quenched by the addition of 10% $Na_2SO_3$. The aqueous/organic mixture may then be separated and extracted with organic solvent, such as DCM. The organic phases may then be pooled, washed with brine, and dried with an anhydrous drying agent prior to filtration and concentration under vacuum. Suitable purification methods known in the art may then be performed, such as silica gel column chromatography. In an embodiment, the organic layers are pooled, dried and the crude product is purified through a silica gel bed. Compound 5 may be eluted from the gel bed with a suitable solvent, which may be a gradient or isocratic. For example, ethyl acetate in hexanes may be used with a gradient of 0-15%.

In some cases, the crude reaction mixture may be used in subsequent reactions without purification.

In some cases, about 0.01-20 vol. or any value therebetween (optionally rounded to the nearest 0.1), or any subrange spanning between any two of these values, such as 0.05-0.5 eq. of $CrO_3$ may be used. For example, 0.01, 0.015, 0.02, 0.025, 0.03, 0.036, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 5, 6, 7, 8, 9, 10, 11, 12, 13, 14, 15, 16, 17, 18, 19, and 20 eq. of $CrO_3$ or others are considered.

In some cases, about 0.01-20 vol. or any value therebetween (optionally rounded to the nearest 0.1), or any subrange spanning between any two of these values, such as 3.15-7 eq. of peroxide, such as TBHP, may be used. For example, 0.01, 0.015, 0.02, 0.025, 0.03, 0.036, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 5, 6, 7, 8, 9, 10, 11, 12, 13, 14, 15, 16, 17, 18, 19, and 20 eq. of peroxide or others are considered.

In some cases, about 0.01-150 vol. or any value therebetween (optionally rounded to the nearest 0.1), or any subrange spanning between any two of these values, such as 0.01-50 vol. of solvent may be used. For example, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 vol. of solvent or others are considered.

In a fourth step, reduction of the allylic ketone to a secondary alcohol (compound 1) is performed. The allylic ketone of compound 5 may be reduced to a secondary allylic alcohol by a suitable reducing agent. In some cases, $NaBH_4$ is used as the reducing agent. In some cases, other reducing agents known in the art may be used.

In some cases, the reduction reaction may be performed by mixing compound 5, about 1.05-1.32 eq. of sodium borohydride ($NaBH_4$) and about 10-18 vol. of solvent, such as ethanol, at room temperature over a period of about 5-60 minutes. In some cases, the $NaBH_4$ is added in portions over a period, for example 5-20 minutes, such as 14 minutes. In some embodiments, the solvent used is dehydrated ethanol.

After the reduction reaction is completed, the crude intermediate 1 may be subjected to work-up methods known in the art. In some embodiments, the solvent of the reaction mixture is removed under vacuum. The crude mixture is then treated with MTBE/$H_2O$. The aqueous/organic mixture may then be separated and extracted with organic solvent, such as MTBE. The organic phases may then be pooled, washed with brine, and dried with an anhydrous drying agent prior to filtration and concentration under vacuum. Suitable purification methods known in the art may then be performed, such as silica gel column chromatography. In an embodiment, the organic layers are pooled, dried and the crude product is purified through a silica gel bed. Compound 1 may be eluted from the gel bed with a suitable solvent, which may be a gradient or isocratic. For example, ethyl acetate in hexanes may be used with a gradient of 0-15%.

In a preferred embodiment, the reduction reaction comprises 1.1 eq. of $NaBH_4$, 10 vol. of EtOH and is conducted at room temperature over a period of about 30 minutes. In an embodiment, 1 eq. of $NaBH_4$ and 15 vol. of ethanol are used. In an embodiment, the reduction reaction comprises 1.32 eq. of $NaBH_4$, 18 vol. of dehydrated EtOH. In an embodiment, the reduction reaction comprises 1.32 eq. of $NaBH_4$, 18 vol. of dehydrated EtOH and is conducted at room temperature over a period of about 15 minutes. In another embodiment, the reduction reaction comprises 1.32 eq. of $NaBH_4$, 18 vol. of dehydrated EtOH and is conducted at room temperature over a period of about 70 minutes. In yet another embodiment, the reduction reaction comprises 1.05 eq. of $NaBH_4$, 15 vol. of dehydrated EtOH and is conducted at room temperature over a period of about 30 minutes. In an embodiment, the reduction reaction comprises 1.1 eq. of $NaBH_4$, 10 vol. of dehydrated EtOH and is conducted at room temperature over a period of about 30 minutes.

In some cases, about 0.01-20 vol. or any value therebetween (optionally rounded to the nearest 0.1), or any subrange spanning between any two of these values, such as 1.05-1.32 eq. of reducing agent, such as $NaBH_4$, may be used. For example, 0.01, 0.015, 0.02, 0.025, 0.03, 0.036, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 5, 6, 7, 8, 9, 10, 11, 12, 13, 14, 15, 16, 17, 18, 19, and 20 eq. of reducing agent or others are considered.

In some cases, about 0.01-150 vol. or any value therebetween (optionally rounded to the nearest 0.1), or any subrange spanning between any two of these values, such as 0.01-50 vol. of solvent may be used. For example, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 vol. of solvent or others are considered.

In a fifth step, an acid catalyzed coupling is performed. Compound 2:

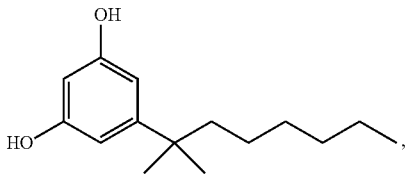

(2)

may be mixed with a suitable acid, such as para-toluenesulfonic acid (pTSA) and compound 1 to yield a compound of formula 6:

(6)

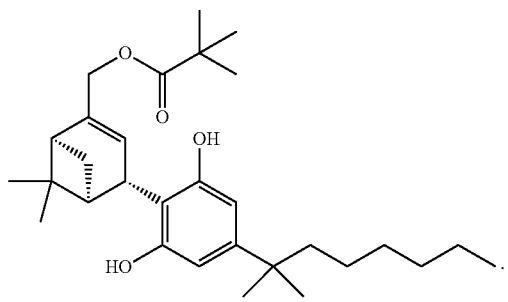

The acid-catalyzed coupling reaction may be understood as a Lewis-acid catalyzed Friedel-Crafts alkylation. Compound 2 and pTSA may be premixed prior to the addition of compound 1. In some cases, the acid-catalyzed coupling reaction comprising about 1.02-1.1 eq. of compound 1, about 0.05-0.28 eq. of para-toluenesulfonic acid (pTSA), about 35-112 vol. of DCM, and 1 eq. of a compound of formula 2 (resorcinol). The reaction may be conducted over a suitable period, such as about 45 minutes.

In an embodiment, the acid-catalyzed coupling reaction comprises 1.02 eq. of compound 1, 0.28 eq. of para-toluenesulfonic acid (pTSA), 112 vol. of DCM, and 1 eq. of the compound of formula 2. In another embodiment, the acid-catalyzed coupling reaction comprises 1.1 eq. of compound 1, 0.28 eq. of para-toluenesulfonic acid (pTSA), 112 vol. of DCM, and 1 eq. of the compound of formula 2. In an embodiment, the acid-catalyzed coupling reaction comprises 1.02 eq. of compound 1, 0.05 eq. of para-toluenesulfonic acid (pTSA), 112 vol. of DCM, and 1 eq. of the compound of formula 2. In an embodiment, the acid-catalyzed coupling reaction comprises 1.02 eq. of compound 1, 0.1 eq. of para-toluenesulfonic acid (pTSA), 112 vol. of DCM, and 1 eq. of the compound of formula 2. In another embodiment, the acid-catalyzed coupling reaction comprises 1.02 eq. of compound 1, 0.1 eq. of para-toluenesulfonic acid (pTSA), 65 vol. of DCM, and 1 eq. of the compound of formula 2.

In a preferred embodiment, the acid-catalyzed coupling reaction comprises 1.02 eq. of compound 1, 0.1 eq. of para-toluenesulfonic acid (pTSA), 35 vol. of DCM, and 1 eq. of the compound of formula 2.

In some cases, other suitable acids may be used, such as $MeSO_3H$. A person of skill in the art will understand that suitable acids may include Lewis acids. In some cases, about 0.05-0.2 eq. of $MeSO_3H$ may be used as the acid. In an embodiment, the acid-catalyzed coupling reaction comprises 1.02 eq. of compound 1, 0.2 eq. of $MeSO_3H$, 112 vol. of DCM, and 1 eq. of the compound of formula 2. In another embodiment, the acid-catalyzed coupling reaction comprises 1.02 eq. of compound 1, 0.05 eq. of $MeSO_3H$, 112 vol. of DCM, and 1 eq. of the compound of formula 2.

In some cases, the acid, such as pTSA, may be dried and/or sonicated prior to use. The reaction may be conducted in oxygen-free conditions, such as under argon or nitrogen gas. After the acid-catalyzed coupling is completed, the crude intermediate 6 may be subjected to work-up methods known in the art. In some embodiments, reaction is quenched with addition of 50% $NaHCO_3$ solution. The aqueous/organic mixture may then be separated and extracted with organic solvent, such as DCM. The organic phases may then be pooled, washed with brine, and dried with an anhydrous drying agent prior to filtration and concentration under vacuum. Suitable purification methods known in the art may then be performed, such as silica gel column chromatography. In an embodiment, the organic layers are pooled, dried and the crude product is purified through a silica gel bed. Compound 6 may be eluted from the gel bed with a suitable solvent, which may be a gradient or isocratic. For example, ethyl acetate in hexanes may be used with a gradient of 0-3%.

In some cases, about 0.01-20 vol. or any value therebetween (optionally rounded to the nearest 0.1), or any subrange spanning between any two of these values, of compound 1 may be used. For example, 0.01, 0.015, 0.02, 0.025, 0.03, 0.036, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 5, 6, 7, 8, 9, 10, 11, 12, 13, 14, 15, 16, 17, 18, 19, and 20 eq. of compound 1 or others are considered.

In some cases, about 0.01-20 vol. or any value therebetween (optionally rounded to the nearest 0.1), or any subrange spanning between any two of these values, such as 0.05-0.28 of acid, may be used. For example, 0.01, 0.015, 0.02, 0.025, 0.03, 0.036, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 5, 6, 7, 8, 9, 10, 11, 12, 13, 14, 15, 16, 17, 18, 19, and 20 eq. of acid or others are considered.

In some cases, about 0.01-150 vol. or any value therebetween (optionally rounded to the nearest 0.1), or any subrange spanning between any two of these values, such as 35-112 vol. of solvent may be used. For example, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 vol. of solvent or others are considered.

In a sixth step, methylation of the aryl hydroxyl groups is performed. Compound 6 may be mixed with a methylating agent and optionally a weak base to yield a compound of formula 7:

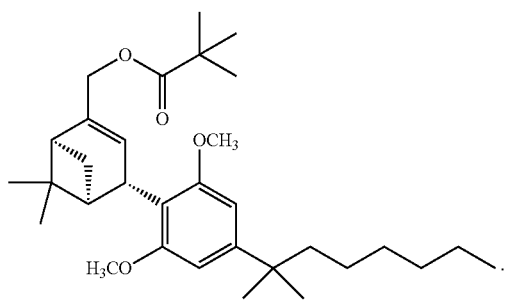

(7)

In some cases, the methylating reagent is dimethyl sulfate. In some embodiments, the methylation reaction comprises 1 eq. of compound 6, about 2.5-5 eq. dimethyl sulfate ($Me_2SO_4$), about 5.3-6.7 eq. of potassium carbonate ($K_2CO_3$) and about 5-20 vol. of acetone. The methylation reaction may occur at a suitable temperature, such as ambient temperature. The reaction may occur over a suitable period, such as 5 minutes to two days. The methylation reaction may be in air-free conditions, such as under argon or nitrogen gas.

In an embodiment, the methylation reaction comprises 5 eq. of $Me_2SO_4$, 6.7 eq. of $K_2CO_3$, 20 vol. of acetone. In a preferred embodiment, the methylation reaction comprises 4 eq. of $Me_2SO_4$, 5.3 eq. of $K_2CO_3$, 20 vol. of acetone, and is conducted at room temperature over a period of about 72 hours.

After the methylation reaction is completed, the crude intermediate 7 may be subjected to work-up methods known in the art. In some embodiments, the solvent is removed from the crude reaction mixture via vacuum. The crude mixture may be reconstituted in solvent, such as MTBE, and washed with water. The organic later may then be washed with brine, and dried with an anhydrous drying agent prior to filtration and concentration under vacuum. Suitable purification methods known in the art may then be performed, such as silica gel column chromatography. In an embodiment, the organic layer is dried and the crude product is purified through a silica gel column. Compound 3 may be eluted from the column with a suitable solvent, which may be a gradient or isocratic. For example, ethyl acetate in hexanes may be used with a gradient of 0.5-3%.

In some cases, about 0.01-20 vol. or any value therebetween (optionally rounded to the nearest 0.1), or any subrange spanning between any two of these values, of methylating agent may be used. For example, 0.01, 0.015, 0.02, 0.025, 0.03, 0.036, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 5, 6, 7, 8, 9, 10, 11, 12, 13, 14, 15, 16, 17, 18, 19, and 20 eq. of methylating agent or others are considered.

In some cases, about 0.01-150 vol. or any value therebetween (optionally rounded to the nearest 0.1), or any subrange spanning between any two of these values, such as 35-112 vol. of solvent may be used. For example, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 vol. of solvent or others are considered.

In a seventh step, a deprotection reaction is performed. In some cases, compound 7 is deprotected to yield compound 8. The deprotection reaction may comprise about 2-9 equivalents of a second base and about 20-155 vol. of a second solvent to yield the compound of formula 8. The second base may be a suitable base, such as lithium aluminum hydride ($LiAlH_4$), potassium tert-butoxide, potassium hydroxide, sodium methoxide, sodium hydroxide, or others. The second solvent may be any suitable solvent known in the art, for example tetrahydrofuran (THF), methyl tert-butyl ester (MTBE), methanol or others.

Water may be optionally used in the reaction. In some cases, the deprotection reaction is about 2.4 eq. $LiAlH_4$ and the second solvent is about 75-155 vol. of tetrahydrofuran (THF). In other cases, the second base is 6 eq. of potassium tert-butoxide, the second solvent is 88 vol. of MTBE and the deprotection reaction further comprises 1.6 eq. of water. In further embodiments, the second base is about 2-9 eq. of potassium hydroxide, the second solvent is about 80 vol. of methanol and the deprotection reaction further comprises about 1 mL of water. In yet further embodiments, the second base is about 6-9 eq. of sodium methoxide, the second solvent is about 20-88 vol. of methanol and the deprotection reaction further comprises about 1.6-22 eq. of water. In some cases, the second base is 9 eq. of sodium methoxide, the second solvent is 20 vol. of methanol, the deprotection reaction further comprises 22 eq. of water and is conducted at a temperature of 37° C. In the above embodiments, the reaction conditions are used to remove a Piv protecting group, but other conditions known in the art may be used when alternate protecting groups are used in Step 2.

In some cases, about 0.01-20 vol. or any value therebetween (optionally rounded to the nearest 0.1), or any subrange spanning between any two of these values, of a second base may be used. For example, 0.01, 0.015, 0.02, 0.025, 0.03, 0.036, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 5, 6, 7, 8, 9, 10, 11, 12, 13, 14, 15, 16, 17, 18, 19, and 20 eq. of second base or others are considered.

In some cases, about 0.01-30 vol. or any value therebetween (optionally rounded to the nearest 0.1), or any subrange spanning between any two of these values, of water may be used. For example, 0.01, 0.015, 0.02, 0.025, 0.03, 0.036, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 5, 6, 7, 8, 9, 10, 11, 12, 13, 14, 15, 16, 17, 18, 19, 20, 21, 22, 23, 24, 25, 26, 27, 28, 29 and 30 eq. of water or others are considered.

In some cases, about 0.01-150 vol. or any value therebetween (optionally rounded to the nearest 0.1), or any subrange spanning between any two of these values, such as 35-112 vol. of solvent may be used. For example, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 vol. of solvent or others are considered.

Chiral Resolution of Intermediate 6 and Methods of Enantiomerically Producing HU308 and HU433

Figure 20:
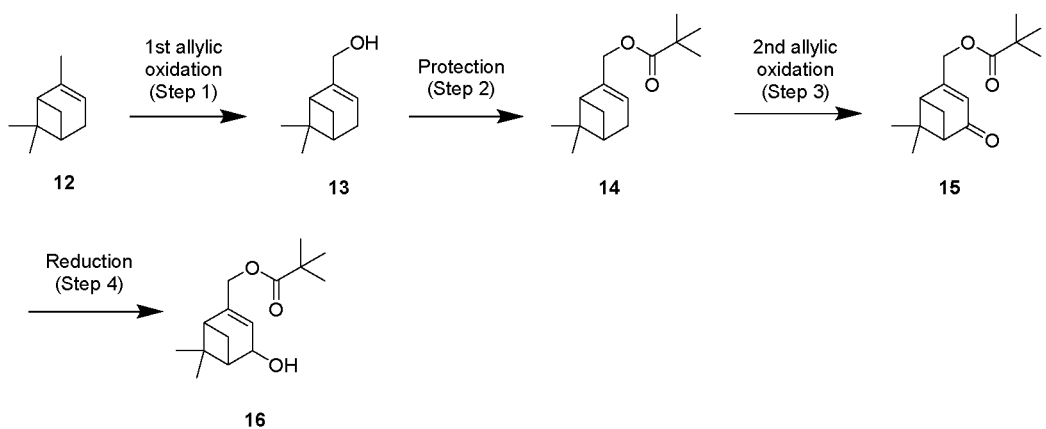
FIG. 20 is a synthetic scheme showing the synthesis of intermediate 16 from an optically impure compound 12.
Figure 21:
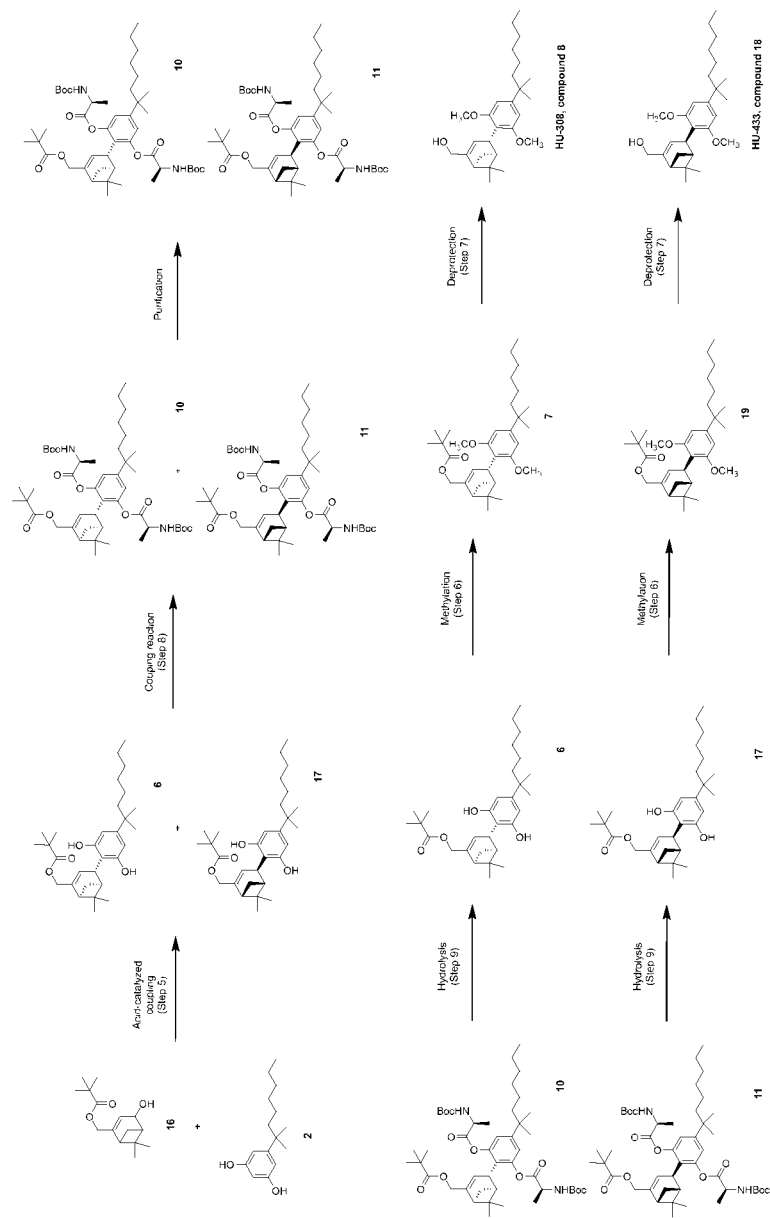
FIG. 21 is a synthetic scheme showing the synthesis of enantiomerically purified compounds 8 and 18 from an optically impure intermediate 16.

Described herein are methods for separation of enantiomers of intermediate 6 (FIGS. 20 and 21). The methods described herein may be used to synthesize enantiomerically purified compounds 8 or 18. The previously described steps 1-7 may be used as described above in the synthesis of HU308 (8) and/or HU433 (18). This procedure may be used to remove unwanted chiral impurities, to obtain an enantiomerically purified sample. This procedure may also be used in a divergent manner, to facilitate the separation and synthesis of both stereoisomers of compound 6 to synthesize both HU308 and HU433 (FIG. 21).

Described below is steps 8 and 9, which would be implemented after step 5 and prior to steps 6 and 7 (FIGS. 20 and 21). In such cases, racemic or otherwise stereomerically impure starting materials may be used. For example in step 5, the acid catalyzed reaction comprises pre-mixing compound 2 and pTSA and subsequently adding compound 16:

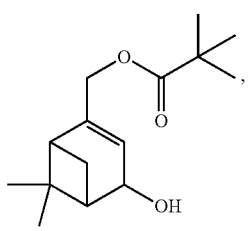
(16)

to yield a first mixture of enantiomer 6:

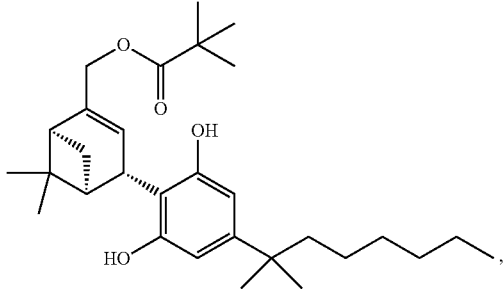
(6)

and enantiomer 17:

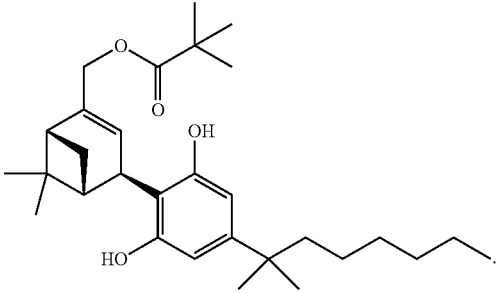
(17)

In an eighth step, a coupling reaction is used. The coupling reaction may comprise coupling conditions, such as DCC/DMAP. The coupling reaction may be used to couple two equivalents of a chiral resolving agent, such as Boc-alanine (for example Boc-L-alanine), to the aryl hydroxyl groups of compounds 6 and 17 to yield a second mixture of diastereomer 10:

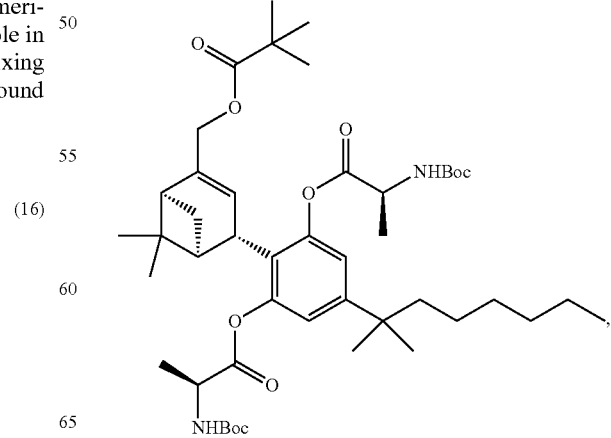
(10)

and diastereomer 11:

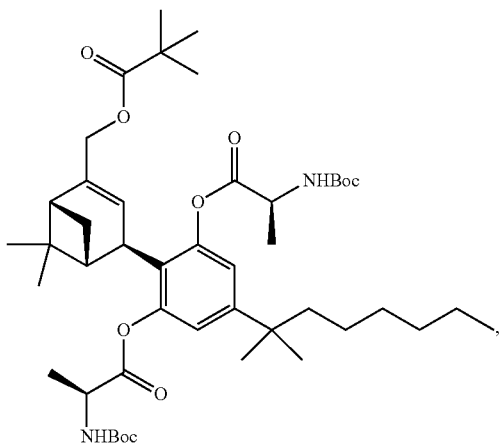

(11)

Although DCC/DMAP coupling conditions are used in the embodiments described herein, a person of skill in the art will understand that other coupling conditions known in the art may be used. For example, coupling conditions that activate a carboxylic group for esterification, such as 1-Ethyl-3-(3-dimethylaminopropyl)carbodiimide (EDC), hydroxybenzotriazole (HOBt) and/or others, may be used.

In a preferred embodiment, the coupling reaction comprises about 2.2 eq. of Boc-alanine, about 2.2 eq. of DCC, about 0.1 eq. of DMAP and the reaction occurs at room temperature for about 1 h. Although the examples shown use Boc-L-Alanine, a person of skill in the art will understand that Boc-D-Alanine may be used. In such embodiments, the coupling would result in a different stereoisomer pair than diasteromers 10 and 11.

After step 8, the second mixture is purified to yield one or both of the diastereomers 10 and 11. Purification may be performed using methods known in the art for separation of diasteromers, such as normal phase or reversed-phase chromatography, column chromatography, HPLC, preparation thin layer chromatography, recrystallization with or without chiral resolving agents or others.

In a preferred embodiment, the second mixture may be purified using silica gel column chromatography to yield enantiomerically purified compound 10; or compound 11. Suitable ratios of crude product:silica gel may be used, for example about 1:37.5, about 1:40, about 1:34.6, or others. Suitable elution solvents may be used, such as ethyl acetate (EtOAc) in hexanes, at various concentrations, such as 5-14%, for example 0-11%, 5-10%, or others. In some cases, the eluting solvent may increase or decrease in polarity (gradient) during elution or remain isocratic, for example 0-50% EtOAc in hexanes, such as 7%.

In a ninth step, a hydrolysis is performed. Either enantiomerically purified compound 10 or 11 may be hydrolyzed in basic conditions to yield enantiomerically purified 6 or 17, respectively. In some cases, the hydrolysis reaction comprises 1 eq. enantiomerically purified compound 10 or 11, about 3-20 eq. of a third base and about 10-20 eq. of solvent, to yield enantiomerically purified compound 6 or 17. The third base may be any suitable base that hydrolyzes the aryl ester groups, while keeping the protecting group on the allylic hydroxyl intact. For example, the third base may be sodium hydroxide. In a preferred embodiment, the third base is 3 eq. of sodium hydroxide (NaOH), the third solvent is 11 vol. of ethanol:water (1:1) and the hydrolysis reaction occurs over 2 hours.

After the ninth step, the resulting enantiomerically purified compound (one or both of compounds 6 and 17), steps 6 and 7 may be performed as described above.

As noted by the methods described above and herein throughout, there are several compositions which are important and useful in the subject matter as described. For example, but without wishing to be limiting, such composition may comprise: a compound 2 and pTSA, Boc-Alanine and DCC, compound 10 and compound 11, compound 6 and compound 17 with one or more of DCC or DMAP, or compound 10 or compound 11 and sodium hydroxide. These examples are not meant to be limiting or exhaustive.

Also provided herein is any compound, intermediate or the like, composition, method or process that results from practicing any of the subject matter contained herein. The present invention will be further illustrated in the following examples.

EXAMPLES

Example 1: Optimization of Chemical Synthesis of HU308 (Compound 8)

Disclosed within this Example are experiments and trials relating to optimization of chemical production of HU308. It will be appreciated by a person of skill in the art that while the experiments and characterization discussed relate to HU308, the methodology would similarly apply to synthesis of the enantiomer, HU433 (compound 18). For example, if (−)-α-pinene was used instead of (+)-α-pinene, steps 1-7 would result in the synthesis of compound 18.

Process Optimization for Step 1 (1$^{st}$ Allylic Oxidation)

The feasibility batch for this step was carried out following the literature procedure (JOC., 55(9), 2855-2860 (1990)), with SeO$_2$ (0.036 eq.)/TBHP (3.5 eq) at 35° C. The intermediate aldehyde was used for next step without further purification—reduction with NaBH$_4$ (0.45 eq.). The intermediate 3 was obtained with 48% yield (FIG. 2).

8 trial reactions were carried out for Step 1 to evaluate reagent stoichiometry, reaction temperature and work up procedure to evaluate more effective reaction & work-up conditions for scale up. The parameters and results are summarized in Table 1.

TABLE 1

| | | | | |
|---|---|---|---|---|
| Optimization Results for Step 1 | | | | |
| Lot No. | Scale | Reaction condition | Parameter changed | Results* |
| HU-01-131 | 500 mg | SM:SeO$_2$ = 1:1.19 At 80° C. | Without t-BuOOH use stoichiometric amount of SeO$_2$ | 0.49 |

TABLE 1-continued

Optimization Results for Step 1

| Lot No. | Scale | Reaction condition | Parameter changed | Results* |
|---|---|---|---|---|
| HU-01-133 | 500 mg | SM:SeO$_2$:HCOOH = 1:1.02:1.51 at 60° C. | Without t-BuOOH use stoichiometric amount of SeO$_2$ | 0.44 |
| HU-01-139-1 | 1 g | SM:SeO$_2$:t-BuOOH = 1:0.036:3.5 at RT | After 2 days, the oxidation reaction was quenched with Sat. Na$_2$S$_2$O$_3$ | 0.77 |
| HU-01-139-2 | 1 g | SM:SeO$_2$:t-BuOOH = 1:0.036:3.5 at RT | In step 1.2, MTBE will be used instead of Et$_2$O | 0.85 |
| HU-01-139-3 | 1 g | SM:SeO$_2$:t-BuOOH = 1:0.036:3.5 at RT | Used as control for comparison | 1 |
| HU-01-139-4 | 1 g | SM:SeO$_2$:t-BuOOH = 1:0.036:3.5 at RT | t-BuOOH will be used as the 70% aqueous solution. | 0.72 |
| HU-01-139-5 | 1 g | SM:SeO$_2$:t-BuOOH = 1:0.02:3.5 at RT | Reduce the catalytic amount of SeO$_2$ | 0.59 |
| HU-03-009 | 1 g | SM:SeO$_2$:t-BuOOH = 1:0.036:2.0 at RT | Reduce the amount of TBHP | 47%** |

*The product was analyzed using the residue of CHCl$_3$ in CDCl$_3$ as an internal standard to compare the yield without purification.
**Isolated yield Results indicated that TBHP with catalytic amount of SeO$_2$ may be better than using stoichiometric amount of SeO$_2$ without TBHP. Compared to the feasibility batch, the oxidation reaction may be carried out at ambient temperature and the similar yield will be obtained. The removal of water from TBHP (70% aqueous solution) may increase the yield. Oxidation using SeO$_2$ (0.036 eq.)/TBHP (2.0 eq.) at ambient temperature may give a similar yield. In the large scale reduction step, solvent MTBE can be used for extraction instead of using Et$_2$O.

Process Optimization for Step 2 (Protection)

The feasibility batch for this step was carried out with trimethylacetyl chloride (2.0 eq.) and pyridine (11.4 eq.) in anhydrous DCM (6 vol.) at 0° C. to ambient temperature overnight and the intermediate 4 was obtained with 83% yield (in a 21.6 g scale reaction). Four trial reactions were carried out for Step 2 to evaluate reagent stoichiometry, and different bases (FIG. 2). The parameters and results are summarized in Table 2.

TABLE 2

Optimization Results for Step 2

| Lot No. | scale | Reaction condition | Parameter changed | Results* |
|---|---|---|---|---|
| HU-01-167-1 | 200 mg | Acid chloride (2.0 eq) DCM (6 vol), py(6 vol) | Used as control for comparison | 1 |
| HU-01-167-2 | 200 mg | Acid chloride (1.2 eq) DCM (6 vol), py(6 vol) | Reduce the amount of Acid chloride | 0.76 |
| HU-01-167-3 | 200 mg | Acid chloride (1.2 eq) DCM (6 vol), py(1.5 eq) | use stoichiometric amount of pyridine | 1.16 |
| HU-01-167-4 | 200 mg | Acid chloride (2 eq) DCM (6 vol), TEA (2.5 eq), DMAP (0.01 eq) | Using TEA as base and catalytic amount of DMAP | 1.35 |
| HU-01-177 | 1.2 g | Acid chloride (1.2 eq) DCM (6 vol), py(1.5 eq) | Scale up HU-01-167-3 | 100% (crude)** |

*The product was analyzed using the residue of CHCl3 in CDCl3 as an internal standard to compare the yield without purification.
**Based on the $^1$H NMR and actual quantity of the crude product Based on the results, the amount of trimethylacetyl chloride can be reduced from 2.0 eq. to 1.2 eq. The base (such as pyridine) can be reduced from 11.4 eq. to 1.5 eq.

Process Optimization for Steps 3 (2$^{nd}$ Allylic Oxidation) and 4 (Allylic Ketone Reduction)

The feasibility batch for this step was carried out with CrO$_3$ (0.53 eq) and TBHP (6.3 eq) in acetonitrile (14.6 vol) and intermediate 5 was obtained with 32% yield. The optimization for this step was done in two ways to evaluate the reagent stoichiometry, different oxidants, and different reaction solvents. The step 3 and step 4 were optimized together (FIG. 2). The parameters and results are summarized in Table 3.

TABLE 3

Optimization results for Step 3 and Step 4

| Lot No. | scale | Reaction condition | Parameter changed | Results* |
|---|---|---|---|---|
| HU-01-063/ HU-01-069 | 10 g | Step3 CrO3 (0.5 eq)/t-BuOOH (6.3 eq)/ACN (14.6 vol)/0-rt after purification then and move to Step 4 NaBH4 (1.0 eq), EtOH (15 vol) | As standard | 12.5% over steps 3 and 4 |
| HU-01-087/ HU-01-103 | 20.75 g | Step3 CrO3 (0.5 eq)/t-BuOOH (6.3 eq)/ACN (14.6 vol)/0-rt after purification then and move to Step 4 NaBH4 (1.0 eq), EtOH (15 vol) | As standard | 11.3% over steps 3 and 4 |
| HU-03-047-1 | 500 mg | Step3 CrO3 (0.5 eq)/t-BuOOH (6.3 eq)/ACN (14.6 vol)/0-rt without purification and move to Step 4 NaBH4 (1.0 eq), EtOH (15 vol) | without purification and move to Step 4 | 19% |
| HU-03-047-2 | 500 mg | Step3 CrO3 (0.5 eq)/t-BuOOH (6.3 eq)/acetone (14.6 vol)/0-rt without purification and move to Step 4 NaBH4 (1.0 eq), EtOH (15 vol) | Oxidation in different solvent without purification and move to Step 4 | 15% |
| HU-03-065 | 500 mg | Step3 NBS(2.6 eq)/THF-H2O(4:1) 60 vol at 0-rt | Using NBS as an oxidant | No product |
| HU-03-067 | 500 mg | Step3 NaOCl(2 eq)/t-BuOOH (7 eq) in ACN (15 vol) at 0-rt | Using NaOCl as an oxidant | No product |
| HU-03-075 | 500 mg | Step3 CrO3 (0.5 eq)/t-BuOOH (6.3 eq)/ACN (14.6 vol)/ at 0° C. without purification and move to Step 4 NaBH4 (1.0 eq), EtOH (15 vol) | Reduce the reaction temperature without purification and move to Step 4 | 16% |
| HU-03-077 | 500 mg | Step3 PCC (2 eq)/t-BuOOH (4 eq)/DCM (25 vol)/at 0° C. | Using PCC as an oxidant | Reaction very slow and not clean |
| HU-03-087 | 500 mg | Step3 CrO3 (0.5 eq)/t-BuOOH (3.15 eq)/ACN (14.6 vol)/0-rt without purification | Reduce the molar ratio of t-BuOOH to 3.15 eq from 6.3 eq without purification | 20.7% |

TABLE 3-continued

Optimization results for Step 3 and Step 4

| Lot No. | scale | Reaction condition | Parameter changed | Results* |
|---------|-------|---------------------|---------------------|----------|
|         |       | and move to Step 4 NaBH4 (1.0 eq), EtOH (15 vol) | and move to Step 4 |         |

*isolated yield

Using NBS, NaOCl and PCC as oxidants, there was no detectable desired product formed. Using acetone as reaction solvent gave similar results. The amount of TBHP may be reduced from 6.3 eq to 3.15 eq. Preferred reaction conditions for these two steps are: $CrO_3$ (0.5 eq)/t-BuOOH (3.15 eq)/ACN (14.6 vol)/0-rt without purification and move to step 4, $NaBH_4$ (1.0 eq), EtOH (15 vol). The two steps will be optimized respectively. Parameters and results of optimization of step 3 are summarized in Table 4.

Using $Na_2CrO_4$ in acetic acid/acetic anhydride as oxidant may be less suitable for this oxidation. The catalytic amount of $CrO_3$ can be further reduced from 0.5 eq to 0.05 eq. The work-up process may be much easier if DCM is used as the reaction solvent.

The feasibility batch for step 4 was carried out with $NaBH_4$ (1.32 eq) in dehydrated EtOH (18 vol). Four trial reactions were carried out for Step 4 to evaluate reagent

TABLE 4

Optimization results for step 3

| Lot No. | scale | Reaction condition | Parameter changed | Results* |
|---------|-------|---------------------|---------------------|----------|
| HU-02-61 | 500 mg | $Na_2CrO_4$ (2.3 eq) in acetic acid (2.8 mL)/acetic anhydride (1.25 mL) | Using $Na_2CrO_4$ as oxidant | Difficult for work-up |
| HU-02-67 | 500 mg | $CrO_3$ (0.5 eq)/t-BuOOH (5 eq)/CAN (14.6 vol)/0-rt | t-BuOOH equivalence change | 26.4% |
| HU-02-75 | 500 mg | $CrO_3$ (0.05 eq)/t-BuOOH (7 eq)/DCM (16 vol)/rt, 4 h | Reduce the amount of $CrO_3$ and using DCM as solvent | 31.2% |
| HU-02-81 | 500 mg | $CrO_3$ (0.05 eq)/t-BuOOH (7 eq)/DCM (16 vol)/rt, 2.5 h | Reduce reaction time | 21.9% |
| HU-02-83 | 500 mg | $CrO_3$ (0.05 eq)/t-BuOOH (5 eq)/DCM (16 vol)/rt, 2.5 h | Reduce the amount of t-BuOOH from 7 eq to 5 eq | 18.9% |
| HU-02-89 | 8 g | $CrO_3$ (0.05 eq)/t-BuOOH (7 eq)/DCM (16 vol)/rt, 1.5 h | Scale up and the reaction was quenched after 1.5 h based on the TLC analysis | 16.4% (with 62.5% starting material recovery) |
| HU-02-91 | 6.76 g | $CrO_3$ (0.05 eq)/t-BuOOH (7 eq)/DCM (16 vol)/rt, 2.5 h | Scale up the reaction | 20.3% (with 63.6% starting material recovery) |
| HU-03-131 | 10 g | $CrO_3$ (0.05 eq)/t-BuOOH (7 eq)/DCM (16 vol)/rt, 2.5 h | Scale up the reaction | 20.7% (with 25.4% starting material recovery) |
| HU-03-135 | 5 g | $CrO_3$ (0.05 eq)/t-BuOOH (7 eq)/DCM (16 vol)/rt, 4 h | Scale up the reaction and using longer reaction time | 22% |

*isolated yield stoichiometry, and reaction volume. The parameters and results are summarized in Table 5.

TABLE 5

The optimization results for step 4

| Lot No. | scale | Reaction condition | Parameter changed | Results* |
|---|---|---|---|---|
| HU-01-69 | 3.3 g | NaBH$_4$ (1.32 eq), EtOH (18 vol), at RT for 15 minutes | As standard | 40% |
| HU-01-103 | 5.3 g | NaBH$_4$ (1.32 eq), EtOH (18 vol), at RT for 70 minutes | As standard | 46.8% |
| HU-02-97 | 200 mg | NaBH$_4$ (1.05 eq), EtOH (15 vol), at RT for 30 minutes | Reduce the amount of NaBH$_4$ | 55.6% |
| HU-02-105 | 200 mg | NaBH$_4$ (1.1 eq), EtOH (10 vol), at RT for 30 minutes | Reduce the amount of NaBH$_4$ and volume of reaction solvent | 56.5% |
| HU-02-115 | 1.02 g | NaBH$_4$ (1.1 eq), EtOH (10 vol), at RT for 30 minutes | Scale up the process | 47.2% |
| HU-02-117 | 4.99 g | NaBH$_4$ (1.1 eq), EtOH (10 vol), at RT for 30 minutes | Scale up the process | 38.6% |

*isolated yield

Preferred reaction conditions are: NaBH$_4$ (1.1 eq) in EtOH (10 vol) at ambient temperature for 30 minutes.

Process Optimization for Step 5 (Acid-Catalyzed Coupling Reaction)

The feasibility batch for this step was carried out by coupling reaction of 1 intermediate 1 (t. 1) with 5-(1,1-Dimethylheptyl)resorcinol (0.98 eq) and anhydrous p-TSA (0.28 eq) as catalyst in anhydrous DCM (112 vol). Intermediate 6 was isolated in 63.4% yield (FIG. 1). Seven trial reactions were carried out for Step 5 to evaluate reagent stoichiometry, reaction volume, and different catalysts. The reaction parameters and results are summarized in Table 6.

TABLE 6

The optimization results for step 5

| Lot No. | scale | Reaction condition | Parameter changed | Results (isolated yield) |
|---|---|---|---|---|
| HU-01-105-1 | 1 g | pTSA (0.28 eq), Int. 1, (1.02 eq) resorcinol(1.0 eq), DCM (112 vol) | Used as control for comparison | 64.7% |
| HU-01-183-1 | 100 mg | pTSA (0.28 eq), Int. 1 (1.1 eq) resorcinol(1.0 eq), DCM (112 vol) | Increase the amount of OH | 71% |
| HU-01-185-1 | 100 mg | pTSA (0.1 eq), Int. 1 (1.02 eq) resorcinol(1.0 eq), DCM (112 vol) | reduce the amount of pTSA | 78% |
| HU-01-193-1 | 100 mg | MeSO$_3$H(0.2 eq), Int. 1 (1.02 eq) resorcinol(1.0 eq), DCM (112 vol) | Using MeSO$_3$H as catalyst | 65.7% |
| HU-01-201-1 | 200 mg | pTSA (0.05 eq), Int. 1 (1.02 eq) resorcinol(1.0 eq), DCM (112 vol) | reduce the amount of pTSA | 72% |
| HU-01-203-1 | 200 mg | MeSO$_3$H(0.05 eq), Int. 1 (1.02 eq) resorcinol(1.0 eq), DCM (112 vol) | Using less amount of MeSO$_3$H as catalyst | 37.5% |
| HU-03-013 | 100 mg | pTSA (0.1 eq), Int. 1 (1.02 eq) resorcinol(1.0 eq), DCM (65 vol) | Reduce reaction volume | 78% |
| HU-03-019 | 100 mg | pTSA (0.1 eq), Int. 1 (1.02 eq) resorcinol(1.0 eq), DCM (35 vol) | Further reduce reaction volume | 78% |

The amount of catalyst (p-TSA) may be reduced from 0.28 eq to 0.1 eq. The reaction volume may be further reduced from 112 vol to 35 vol. MeSO$_3$H may be less desirable than p-TAS as a catalyst. Preferred reaction conditions are: pTSA (0.1 eq), intermediate 1 (Int. 1, 1.02 eq), resorcinol (1.0 eq) and reaction in anhydrous DCM (35 vol).

Process Optimization for Step 6 (Methylation)

The feasibility batch for this step was carried out with Me$_2$SO$_4$ (5 eq) and K$_2$CO$_3$ (6.7 eq) in acetone (20 vol) with 85.3% yield (FIG. 1). 5 trial reactions were carried out for Step 6 to evaluate reagent stoichiometry, reaction volume, different reagents and different reaction solvents. The parameters and results are summarized in Table 7.

TABLE 7

Optimization results for step 6

| Lot No. | scale | Reaction condition | Parameter changed | Results (isolated yield) |
|---|---|---|---|---|
| HU-03-031 | 100 mg | Me$_2$SO$_4$ (4.0 eq)/K$_2$CO$_3$ (5.3 eq) acetone (20 vol), at RT for 72 h | As standard | 81% |
| HU-03-033 | 100 mg | MeI (4.0 eq)/K$_2$CO$_3$ (5.3 eq) acetone (20 vol), at RT for 72 h | Different reagent | Trace desired product |
| HU-03-041 | 100 mg | MeI (4.0 eq)/K$_2$CO$_3$ (5.3 eq) DMF (20 vol), at RT for 66 h | Different solvent | Only Mono methylated product |
| HU-03-083 | 200 mg | Me$_2$SO$_4$ (4.0 eq)/K$_2$CO$_3$ (5.3 eq) acetone (10 vol), at RT for 66 h | Reduce reaction vol | SM + Mono-Methylated and desired product |
| HU-03-085 | 200 mg | Me$_2$SO$_4$ (2.5 eq)/K$_2$CO$_3$ (5.3 eq) acetone (5 vol), at RT for 66 h | Reduce reaction vol & Me$_2$SO$_4$ ratio | SM + Mono-Methylated and desired product |

The amount of Me$_2$SO$_4$ may be reduced from 5 eq to 4 eq and the base (K$_2$CO$_3$) may be reduced from 6.7 eq to 5.3 eq. MeI may be less effective than Me$_2$SO$_4$ as a methylation reagent. 20 volume of acetone is the preferred reaction volume. The preferred reaction conditions are: Me$_2$SO$_4$ (4.0 eq)/K2CO3 (5.3 eq) acetone (20 vol), at ambient temperature for 72 h.

Process Optimization for Step 7 (Deprotection)

The feasibility batch for this step was carried out with LiAlH$_4$ (2.4 eq) in anhydrous THF (75 vol) with 84F yield (FIG. 1). 9 trial reactions (the model compound—intermediate 4 was used for 4 trial reactions) were carried out for Step 7 to evaluate reagent stoichiometry, reaction volume, different reagents and different reaction solvents. The parameters and results are summarized in Table 8.

TABLE 8

Optimization results for step 7

| Lot No. | scale | Reaction condition | Parameter changed | Results (isolated yield) |
|---|---|---|---|---|
| HU-01-119 | 1.23 g | LiAlH$_4$(2.4 eq) THF(75 vol) | Used as control | 84% |
| HU-02-17 | 500 mg of Model compound | LiAlH$_4$(2.4 eq) THF(155 vol) | Used as control for model compound | 73% |
| HU-02-19 | 500 mg of Model compound | p-TSA · H$_2$O(0.27 eq) DCM(15 vol) | Acid hydrolysis | No Reaction |
| HU-02-23 | 500 mg of Model compound | t-BuOK(6 eq) H$_2$O(1.6 eq) MTBE (88 vol) | Base Hydrolysis | 95% (Crude) Contains solvent peaks in NMR |
| HU-02-25 | 500 mg of Model compound | NaOMe(6 eq) H$_2$O(1.6 eq) MeOH(88 vol) | Using NaOMe as base | 88% (crude) |
| HU-03-101 | 100 mg of Model compound | KOH(2 eq) MeOH:H2O (1:1) 4 days, At 35° C. | Using KOH as base | Product + trace amount of starting material |
| HU-03-099 | 25 mg | NaOMe(6 eq) H$_2$O(1.6 eq) MeOH(88 vol) 4 days, At 35° C. | Same as in HU-02-25 | Only product by TLC |
| HU-03-123-1 | 100 mg | NaOMe (9 eq)/ H$_2$O 22 eq) in MeOH (80 vol) at 37° C. | Deprotection with NaOMe and H$_2$O | 91.4% |
| HU-03-123-2 | 100 mg | KOH (9 eq)/H$_2$O (1 mL)/ MeOH (80 vol), at 37° C. | Deprotection with KOH and H$_2$O | Reaction very slow (4 days) |

TABLE 8-continued

Optimization results for step 7

| Lot No. | scale | Reaction condition | Parameter changed | Results (isolated yield) |
|---|---|---|---|---|
| HU-03-129 | 200 mg | NaOMe (9 eq)/ H₂O 22 eq) in MeOH (20 vol), at 37° C. | Reduce the reaction volume | 95.6% (crude) |
| HU-03-137 | 1.66 g | NaOMe (9 eq)/ H₂O 22 eq) in MeOH (20 vol), at 37° C. | Scale up the reaction HU-03-129 | 95% (crude) |

Use of the highly reactive LiAlH$_4$ can be avoided. The deprotection under catalytic amount of p-TSA in DCM may be less effective. The deprotection may be achieved through basic hydrolysis using either KOH or MeONa, and MeONa is the preferred choice for the deprotection. The preferred reaction conditions are: NaOMe (9 eq.)/H$_2$O (22 eq.) in MeOH (20 vol.), at 37° C.

Materials and Methods

Step 1: Synthesis of Intermediate 3

70% t-butyl hydroperoxide (286 mL, 2.055 mol, 3.5 eq) was extracted with 355 mL of DCM. The organic layer (74 mL of aqueous layer was discarded) was transferred into a 2 L three neck round bottom flask equipped with a condenser, thermometer and addition funnel. To this flask was charged SeO$_2$ (2.35 g, 0.021 mol, 0.036 eq). The reaction mixture was stirred at ambient temperature for 30 minutes.

α-pinene (80 g, 0.59 mol, 1.0 eq) was added dropwise via the addition funnel at 22-31° C. for 60 minutes. The reaction mixture was stirred at ambient temperature for 48 hours. TLC (hexanes, visualized by UV and KMnO$_4$) indicated the absence of starting material. To the reaction mixture, 10% KOH (300 mL) was added while maintaining the temperature <27° C. The organic layer was separated and washed with brine (1×300 mL). Peroxide test showed a positive result. The organic layer was stirred with 10% Na$_2$SO$_3$ solution (250 mL) for 1 hour and peroxide test was found to be less than 3 mg/mL. The organic layer was separated and washed with brine (1×300 mL). After drying over Na$_2$SO$_4$ and filtration, the filtrate was concentrated under vacuum to dryness to obtain a yellowish oily residue (163 g).

In a 2 L three neck round bottom flask, the yellowish oily residue was dissolved in dehydrated EtOH (400 mL) under argon. The solution was cooled with water bath. To this solution was added NaBH$_4$ (9.96 g, 0.263 mol, 0.45 eq) in portions at 18-20° C. The reaction mixture was stirred overnight while allowing the temperature gradually increased to ambient temperature. The completion of reaction was confirmed by TLC (10% EtOAc/hexanes, visualized by UV and KMnO$_4$). The reaction mixture was cooled with ice-water bath to 9-13° C., and the reaction was quenched with 10% HCl (180 mL), and the final pH=4. EtOH was removed under vacuum. The residue was treated with H$_2$O/MTBE (100 mL/250 mL). The aqueous layer was extracted with MTBE (2×220 mL). The combined organic layer was washed with brine and then dried over Na$_2$SO$_4$ prior to filtration. The filtrate was concentrated under vacuum to dryness to give 90 g of a yellowish oily residue.

Figure 3:
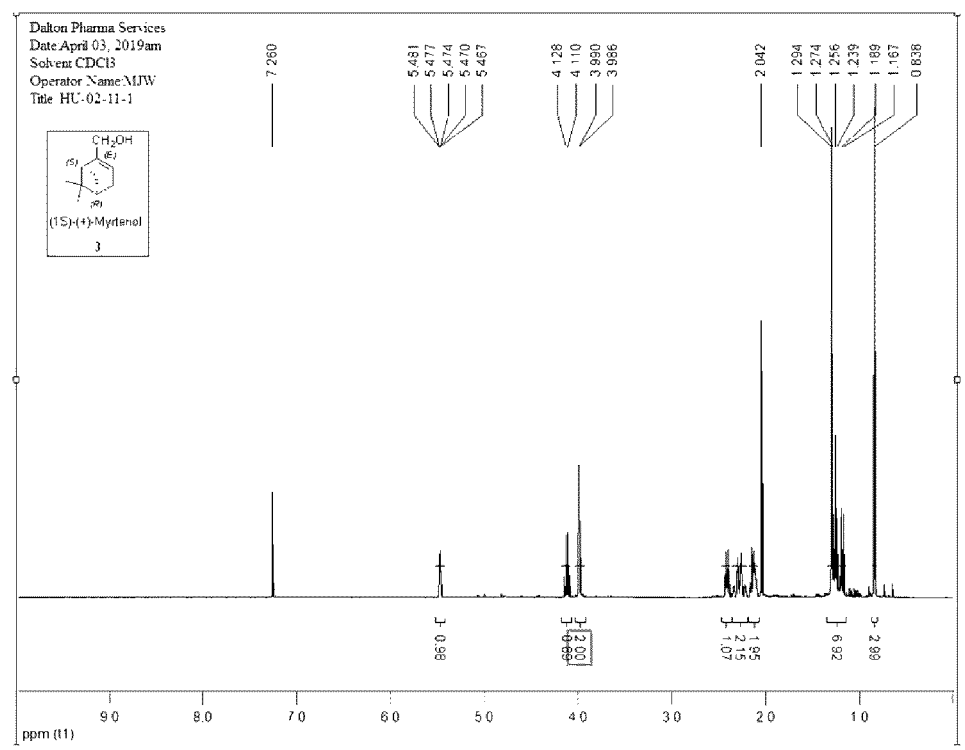
FIG. 3 is a $^1$H-NMR spectrum of Int. 3.

The crude product was purified through a silica gel bed (1.35 kg), eluted with EtOAc/hexanes (0, 2.5%, 5%, 7.5% 10%, 12.5% and 15%). The column fractions were analyzed by TLC and fractions containing pure intermediate were combined and concentrated to obtain 50.6 g of intermediate 3 in 56% yield. ¹H-NMR of intermediate 3 is shown in FIG. 3.

Step 2: Synthesis of Intermediate 4

Figure 4:
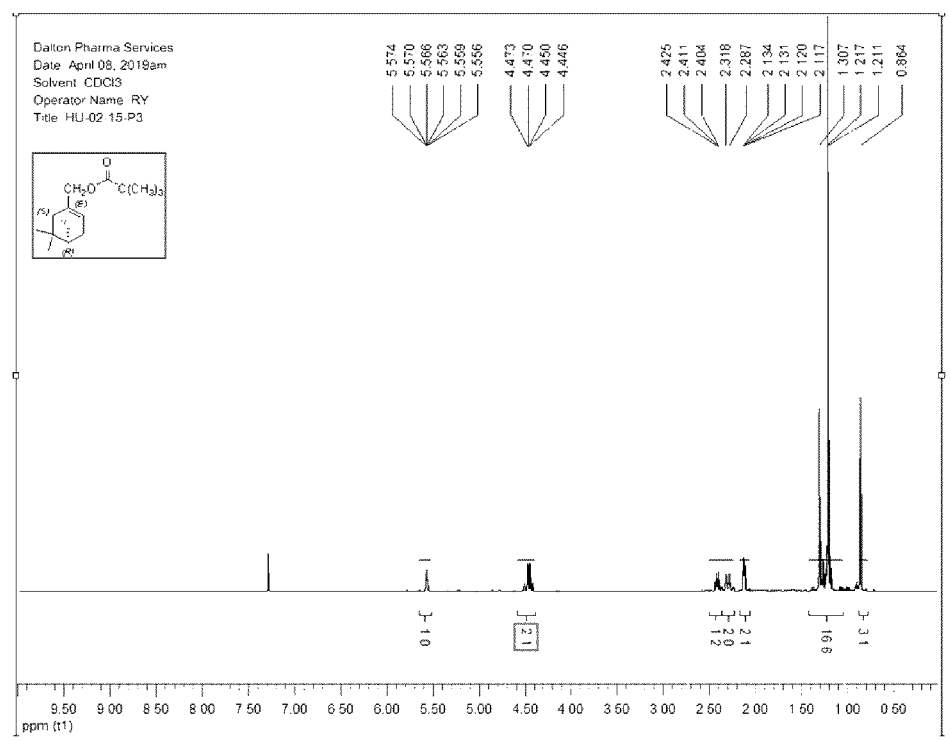
FIG. 4 is a $^1$H-NMR spectrum of Int. 4.

In a 1 L round bottom flask, the intermediate 3 (50.6 g, 0.33 mol, 1 eq) was dissolved in anhydrous DCM (250 mL) under argon. To this solution was added anhydrous pyridine (40.2 mL, 0.499 mol, 1.5 eq). The solution was cooled with ice-H$_2$O bath. Then pivaloyl chloride (49.1 mL, 0.399 mol, 1.2 eq) was added dropwise over 40 minutes while maintaining the temperature 4-6° C. After 1.5 hour, the ice-bath was removed and let the reaction mixture warm up to ambient temperature and stirred at that temperature overnight. After 19 hours, TLC (10% EtOAc/hexanes, visualized by UV and KMnO$_4$) indicated the completion of reaction. The reaction mixture was diluted with MTBE (300 mL). The reaction mixture was washed with 10% HCl (1×300 mL), Sat. NaHCO$_3$ (1×250 mL) and brine (1×250 mL). The organic layer was dried over Na$_2$SO$_4$. The filtrate was concentrated under vacuum to dryness. The residue was purified on silica gel column (800 g cartridge), eluted with EtOAc/hexanes (0-5%) to obtain intermediate 4 72.5 g with 92.3% yield. ¹H-NMR of intermediate 4 is shown in FIG. 4.

Step 3: Synthesis of Intermediate 5

In a 250 mL round bottom flask, CrO$_3$ (169 mg, 0.0017 mol, 0.05 eq) was charged followed by the addition of DCM (64 mL) and t-butyl hydroperoxide (32.4 mL, 0.24 mol, 7 eq). The reaction mixture was stirred at ambient temperature and a red brown solution was obtained.

Figure 5:
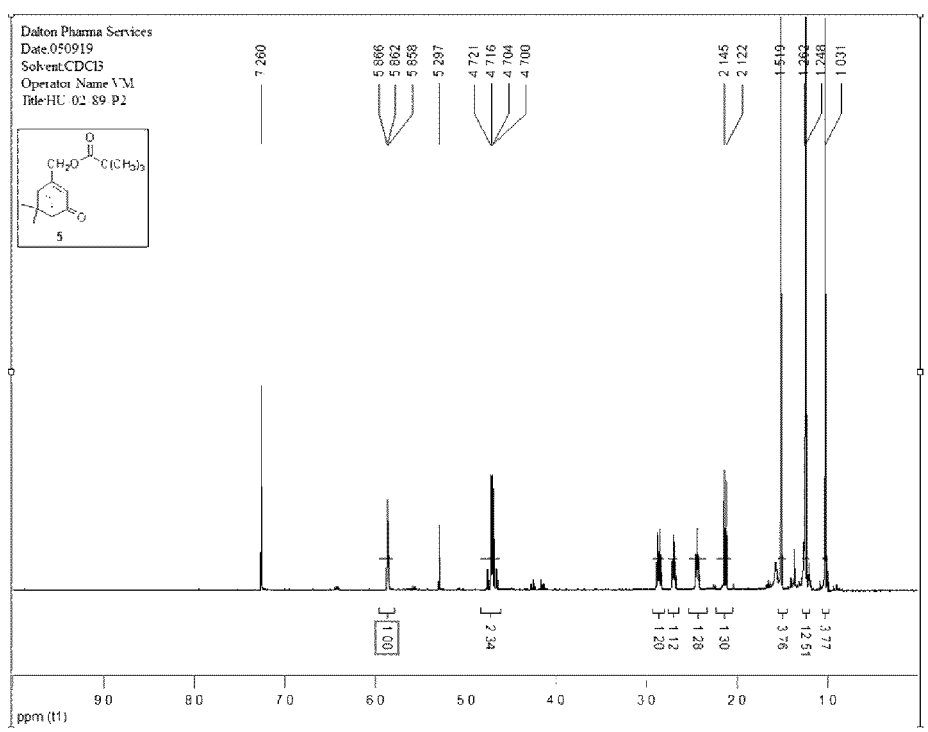
FIG. 5 is a $^1$H-NMR spectrum of Int. 5.

To the above mixture was added a solution of intermediate 4 (8.0 g, 0.0338 mol, 1.0 eq) in DCM (200 mL). The reaction mixture was stirred at ambient temperature for 2.5 hours. TLC (20% EtOAc hexanes visualized by UV and KMnO$_4$) was checked. The reaction was quenched by adding 10% Na$_2$SO$_3$ (190 mL) slowly. The layers were separated, and the aqueous layer was extracted with DCM (2×150 mL). The combined DCM layer was washed with brine (1×150 mL). After drying over Na$_2$SO$_4$, the filtrate was concentrated under vacuum to dryness. The crude product was purified on silica gel column (240 g cartridge), eluted with EtOAc hexanes (0-15%) to obtain intermediate 5 1.39 g with 16.4% yield. ¹H-NMR of intermediate 5 is shown in FIG. 5.

Step 4. Synthesis of Intermediate 1

Figure 6:
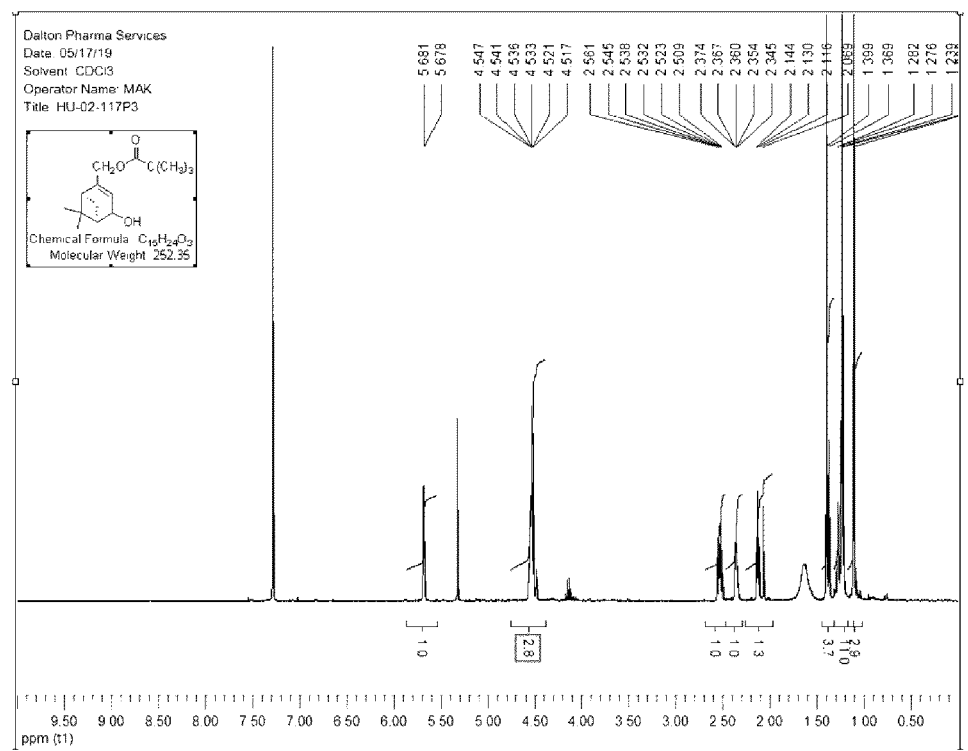
FIG. 6 is a $^1$H-NMR spectrum of Int. 1.

In a 250 mL round bottom flask, intermediate 5 (4.99 g, 0.199 mol, 1.0 eq) was dissolved in dehydrated EtOH (50 mL) under argon. To this solution was added NaBH$_4$ (830 mg, 0.219 mol, 1.1 eq) in portions over 14 minutes. The reaction mixture was stirred at ambient temperature for 40 minutes. TLC (20% EtOAc/hexanes, visualized by UV and KMnO$_4$) indicated the completion of reaction. Solvent was removed under vacuum. The residue was treated with MTBE/H$_2$O (250 mL/175 mL). The aqueous layer was extracted with MTBE (1×150 mL). The combined organic layer was dried over $Na_2SO_4$. After filtration, the filtrate was concentrated under vacuum to dryness. The residue was purified on a silica gel column (220 g silica gel cartridge) using Biotage. The column was eluted with EtOAc/hexanes 0% 1 column volume (CV); 0-8% 7 CV; 8-15% 5 CV; 15% 2 CV to obtain intermediate 1 1.94 g with 38.6% yield. $^1$H-NMR of intermediate 1 is shown in FIG. 6.

Step 5: Synthesis of Intermediate 6

Figure 7:
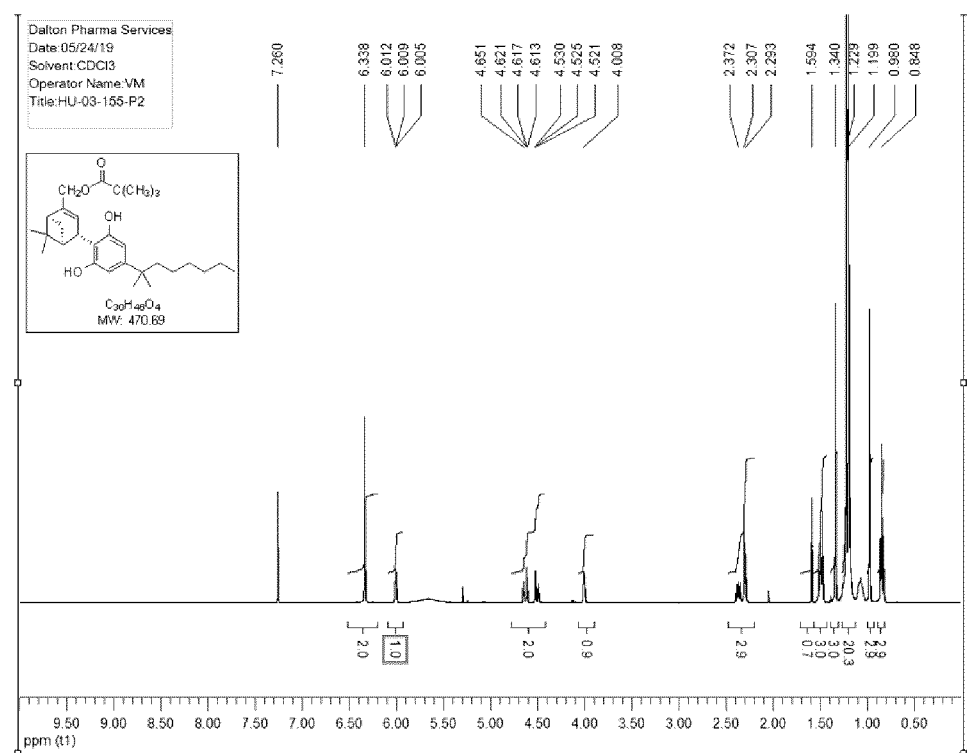
FIG. 7 is an $^1$H-NMR spectrum of Int. 6.

In a 500 mL round bottom flask, p-Toluenesulfonic acid monohydrate (0.62 g, 0.0033 mol, 0.1 eq) was suspended in anhydrous toluene (150 mL) and sonicated for 2 minutes. Toluene was removed under vacuum (0.85 Torr) at 35-40° C. The same process was repeated one more time. To the 500 mL flask containing dried p-TSA was charged a solution of resorcinol derivative (7.7 g, 0.0327 mol, 1.0 eq) in anhydrous DCM (193 mL) under argon. The reaction mixture was stirred under argon for 5 minutes. And then a solution of intermediate 1 (8.4 g, 0.0334 mol, 1.02 eq) in anhydrous DCM (77 mL) was added slowly. After addition, the reaction mixture was stirred at ambient temperature for 45 minute. TLC (EtOAc/hexanes, visualized by UV and $KMnO_4$) indicated the completion of reaction. The reaction mixture was diluted with DCM (300 mL) and transferred into a 2 L round bottom flask. The reaction was quenched with 800 mL of half saturated $NaHCO_3$ (400 mL of sat. $NaHCO_3$ and 400 mL USP purified $H_2O$). The layers were separated. The aqueous layer was extracted with DCM (2×500 mL). The combined organic layer was washed with brine (1×500 mL). After drying over $Na_2SO_4$, the filtrate was concentrated under vacuum to dryness to obtain a crude product 15.73 g. The crude product was purified on silica gel column (silica gel: 378 g; 5.7×37 cm), eluted with hexanes (1.1 L); 0.5% EtOAc/hexanes (0.6 L); 0.7% EtOAc/hexanes (0.5 L); 3% EtOAc/hexanes (4 L) to obtain intermediate 6 11.46 g with 74.4% yield. $^1$H-NMR of intermediate 6 is shown in FIG. 7.

Step 6: Synthesis of Intermediate 7

Figure 8:
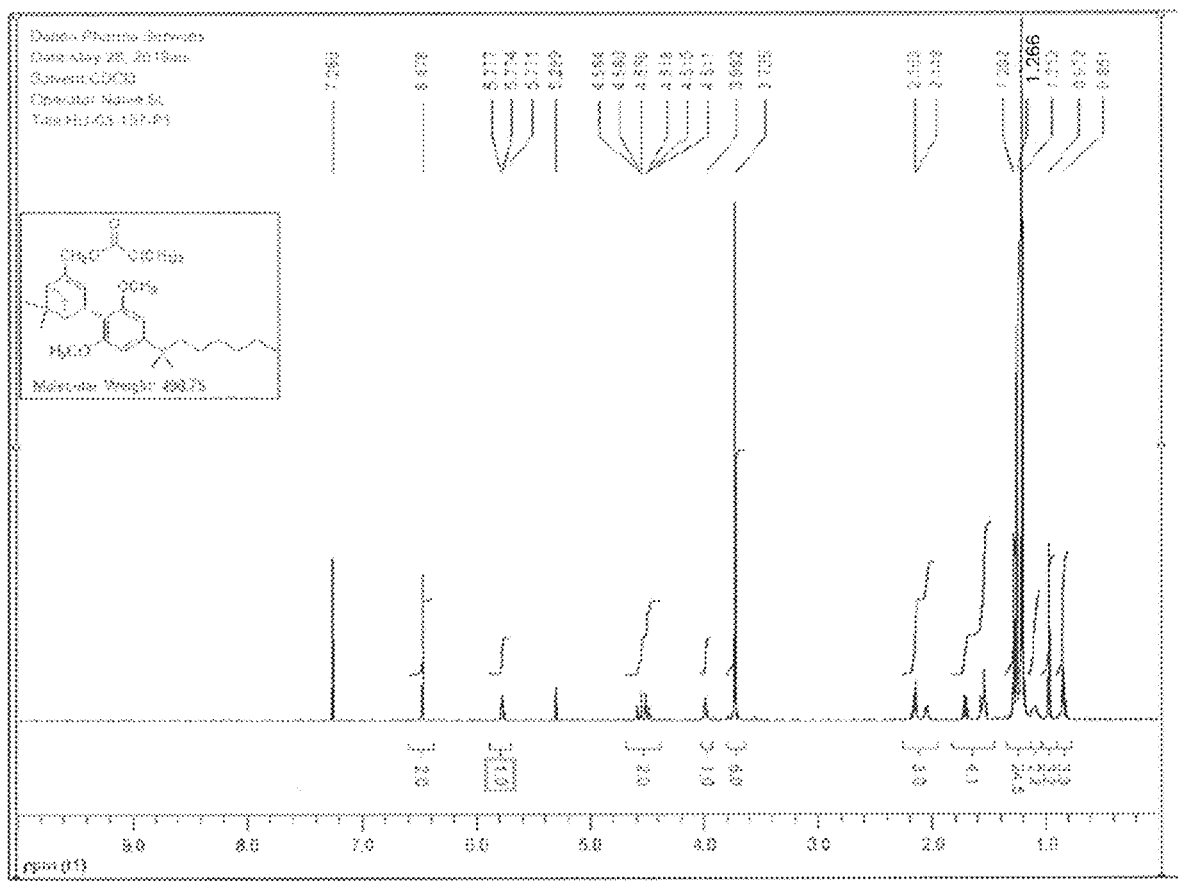
FIG. 8 is a $^1$H-NMR spectrum of Int. 7.

In a 500 mL round bottom flask, the intermediate 6 (11.62 g, 0.0247 mol, 1.0 eq) was dissolved in HPLC grade acetone (232 mL) under argon. To this solution was added $K_2CO_3$ (18.08 g, 0.131 mol, 5.3 eq). After stirring for 5-10 minutes, $Me_2SO_4$ (9.4 mL, 0.0987 mol, 4.0 eq) was added. The reaction mixture was stirred at ambient temperature for 2 days. TLC (10% EtOAc/hexanes, visualized by UV and $KMnO_4$). Solvent was removed under vacuum. The residue was suspended in MTBE (500 mL), and washed with USP purified $H_2O$ (2×500 mL), brine (1×500 mL). After drying over $Na_2SO_4$, the filtrate was concentrated under vacuum to dryness to give the crude product 19.5 g. The crude product was purified on silica gel column (silica gel: 328 g; 5.7×32 cm), eluted with hexanes (1.0 L); 0.5% EtOAc/hexanes (0.5 L); 0.75% EtOAc/hexanes (0.5 L); 1% EtOAc/hexanes (1 L); 1.5% EtOAc/hexanes (0.5 L); 2% EtOAc/hexanes (1 L); 3% EtOAc/hexanes (2 L) to obtain intermediate 7 11.76 g with 95.5% yield. $^1$H-NMR of intermediate 7 is shown in FIG. 8.

Step 7: Synthesis of HU308 (Compound 8)

Figure 9A:
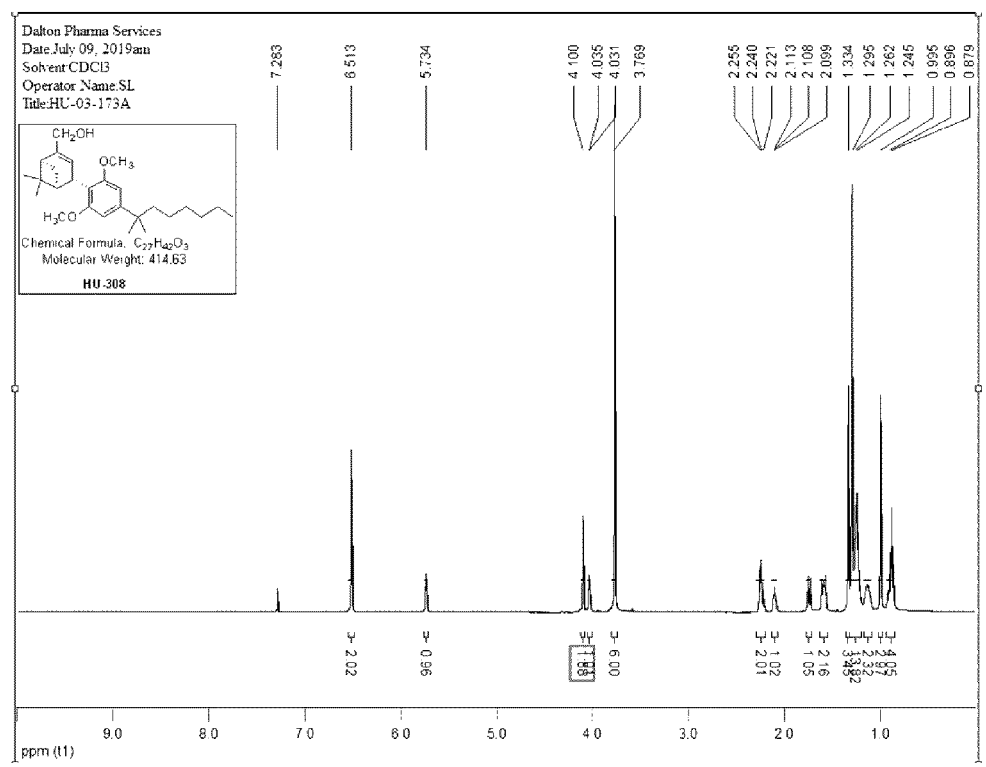
FIGS. 9A and 9B are a $^1$H-NMR spectrum of HU308 (compound 8); and a $^{13}$C-NMR spectrum of HU308 (compound 8), respectively.
Figure 9B:
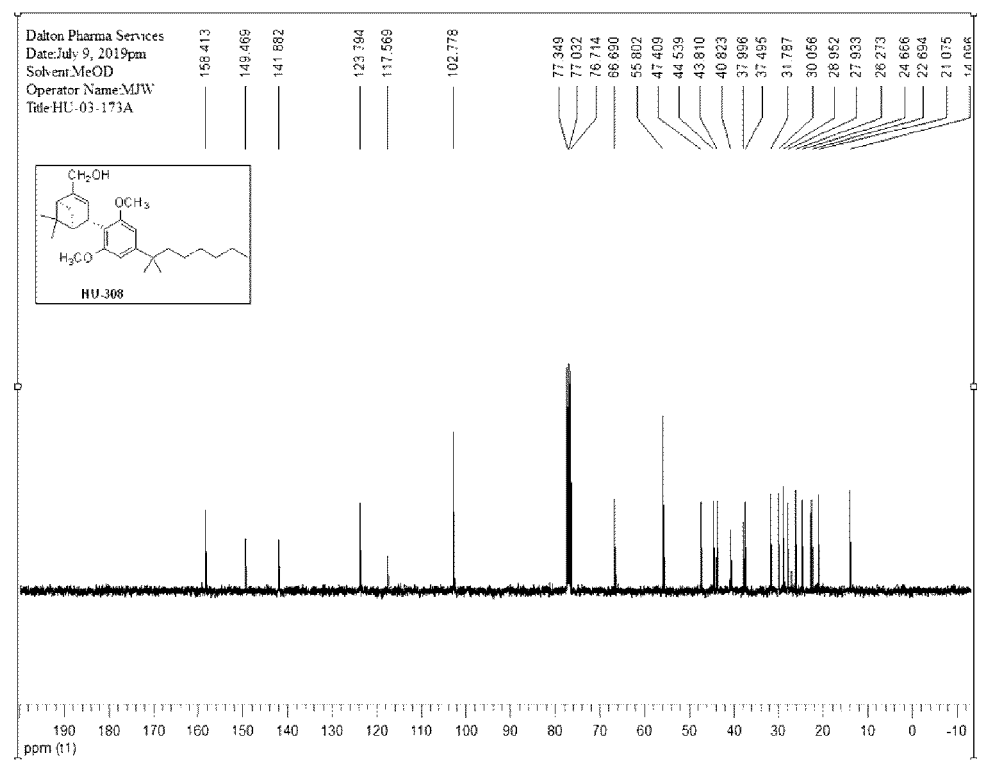

In a 1 L round bottom flask, the intermediate 7 (11.62 g, 0.0233 mol, 1.0 eq) was dissolved in MeOH (230 mL) under argon. To this solution was added USP purified $H_2O$ (9.3 mL, 0.513 mol, 22 eq), followed by the addition of a solution NaOMe in MeOH (5 mol/L) (41.9 mL, 0.210 mol, 9.0 eq). The reaction mixture was stirred at 37° C. The reaction was monitored by TLC (EtOAc/hexanes, visualized by UV and $KMnO_4$). After 2 days, the reaction mixture was allowed to cool to ambient temperature. The pH was adjusted to pH=5-6 with $CH_3COOH$. Solvent was removed under vacuum. The residue was suspended in EtOAc (300 mL) and washed with $H_2O$ (1×230 mL). The aqueous layer was extracted with EtOAc (2×230 mL). The combined organic layer was washed with sat. $NaHCO_3$ (1×230 mL), brine (1×230 mL). After drying over $Na_2SO_4$, the filtrate was concentrated under vacuum to dryness to give the crude product HU308 (compound 8) 10.5 g in quantitative yield. After combination with the product from process development batches, 11.5 g of crude HU308 was obtained. The crude product was purified via a silica gel bed (silica gel: 125 g) using a 350 mL sintered glass funnel. After equilibrium with 3% EtOAc/hexanes (300 mL), and loading sample with DCM (10 mL), the bed was eluted with: 3% EtOAc/hexanes (0.4 L); 8% EtOAc/hexanes (0.3 L); 10% EtOAc/hexanes (1.5 L) to obtain HU308 10.20 g as sticky oil. The purified product was co-evaporated with pentane (10 mL), and stored at −78 to −20° C. to obtain 9.95 g of HU308 as a white semi solid. $^1$H-NMR and $^{13}$C-NMR of compound 8 is shown in FIGS. 8 and 9. The Certificate of Analysis is shown in FIG. 10.

Examples of Changes Between Development Batches and Non-GMP Engineering Batches

Examples of differences for all steps between non-GMP engineering batch and development batches are summarized below:

Step 1: Overhead stirrer was used for non-GMP engineering batch instead of magnetic stirrer.

Step 2: Overhead stirrer was used for non-GMP engineering batch instead of magnetic stirrer.

Step 3: Differences shown below in Table 12

TABLE 9

| Differences between batches in step 3 | | | | |
|---|---|---|---|---|
| Scale | Equivalence of $CrO_3$ | Equivalence of TBHP | Vol | Reaction time | Stirrer |
| Intermediary scale-up Batch | 0.05 | 7 | 33 | 2.5 hours | magnetic stirrer |
| Scale-up for non-GMP engineering batch | 0.05 | 5 | 16 | 2-4 hours | overhead stirrer |

Step 4: Overhead stirrer was used for non-GMP engineering batch instead of magnetic stirrer.

Step 5: Overhead stirrer was used for non-GMP engineering batch instead of magnetic stirrer.

Step 6: Overhead stirrer was used for non-GMP engineering batch and GMP batch instead of magnetic stirrer.

Step 7: Overhead stirrer was used for non-GMP engineering batch and GMP batch instead of magnetic stirrer. For non-engineering batch and GMP batch, purified HU308 obtained from silica gel chromatographic purification was further triturated in water to obtain the final product HU308 in white solid form.

Example 2: Chiral Resolution of Intermediate 6

Initial Testing of Chiral Resolving Agents

During multiple rounds of synthesizing HU308 (compound 8), the final product in one of the rounds was determined to have a diastereomeric contaminant. Different commercial batches of starting material were tested for optical purity (Table 10). Table 10 shows the optical rotation of α-(+)-pinene in three commercial batches. Cat No. 268070 showed a suitable optical rotation, while Cat Nos. 43566 and W290238 exhibited undesirable optical rotations. The optical data suggested that the optical purity of starting materials was variable. Chiral resolution strategies were then explored to separate the chiral impurities. In cases where the optical rotation of starting materials is desirable, the chiral resolution step may be omitted from the synthesis.

TABLE 10

Optical rotation of commercially available batches of α-(+)-pinene

| Cat No. | Optical Rotation |
| --- | --- |
| 268070 | +37.890 DEGREES |
| 43566 | +38.089 DEGREES |
| W290238 | +31.138 DEGREES |

Chiral resolution was first attempted by complexation/crystallization with a chiral resolving agent such as brucine. Complexation experiments with Int. 6 (60-500 mg) (1 eq) and brucine (1 eq) were tried in different solvent systems such as DCM, acetone (30 vol, with 2 eq of $H_2O$), MeOH/hexanes (9:1, 2 vol), 1-PrOH (2 vol). No precipitation was observed in any of the testing conditions. Two equivalents of brucine was also tested as a chiral auxiliary for the chiral resolution of Int.6 in the following solvent systems: 1) acetone (30 vol, with 2 eq of $H_2O$)—there was no precipitation observed at ambient temperature and at 0~4° C.; 2) MeOH/hexanes (9:1, 2 vol)—the excess of Brucine did not go into solution at room temperature or after heating; and 3) 1-PrOH (2 vol): no precipitation observed at ambient temperature and at 0~4° C.

Figure 11:
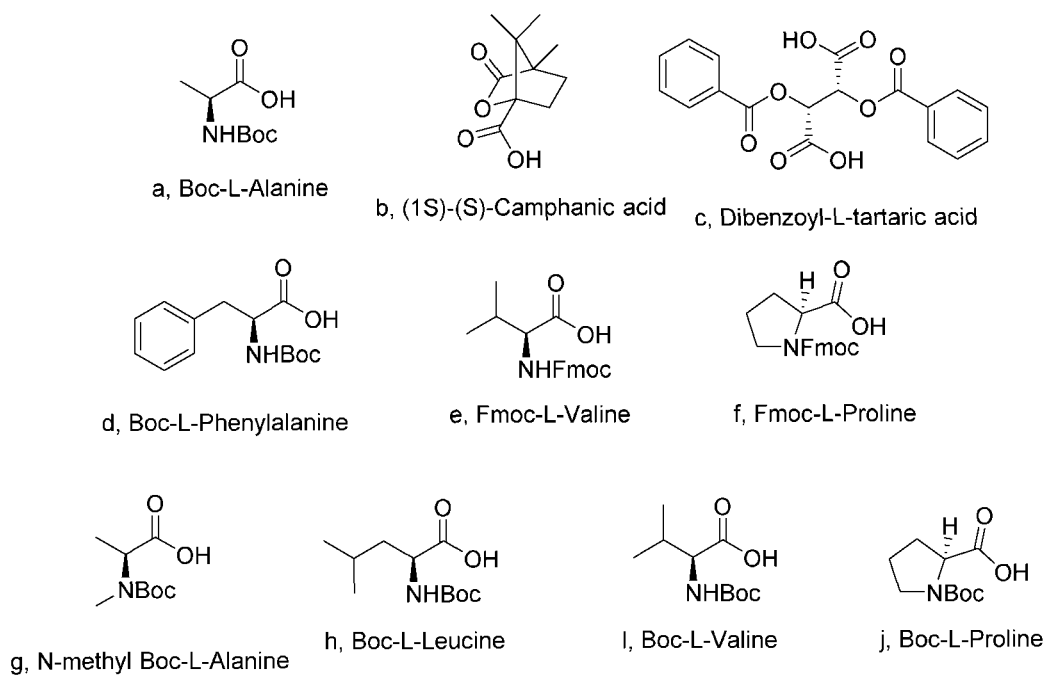
FIG. 11 is a list of chiral resolving agents used during trial experiments to find diastereomers of compound 6 for chiral resolution.
Figure 12:
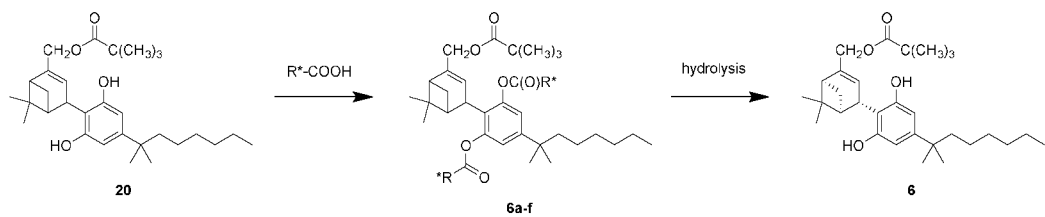
FIG. 12 is a schematic depicting coupling of chiral resolving agents (R—COOH) and compound 20 (optically impure Int. 6) to diastereomers 6(a-f) and subsequent hydrolysis to enantiomerically purified Int. 6.

Coupling of several chiral auxiliaries were then tested. Examples of tested chiral auxiliaries can be found in FIG. 11. A general scheme for the synthesis of diasteromers of intermediate 6 (6a-6j) can be found in FIG. 12. The diasteromers 6a-6j were synthesized using DCC/DMAP coupling conditions. The diasteromers were then subjected to silica gel column/HPLC purification to determine if separation of the diasteromers was possible. After separation, the purified diasteromers were then subjected to hydrolysis under basic conditions to yield enantiomerically purified intermediate 6. Test reactions and purification of diastereomeric esters 6a-f revealed that Boc-alanine (compound a in FIG. 11) was the preferred ester for separation.

Figure 13:
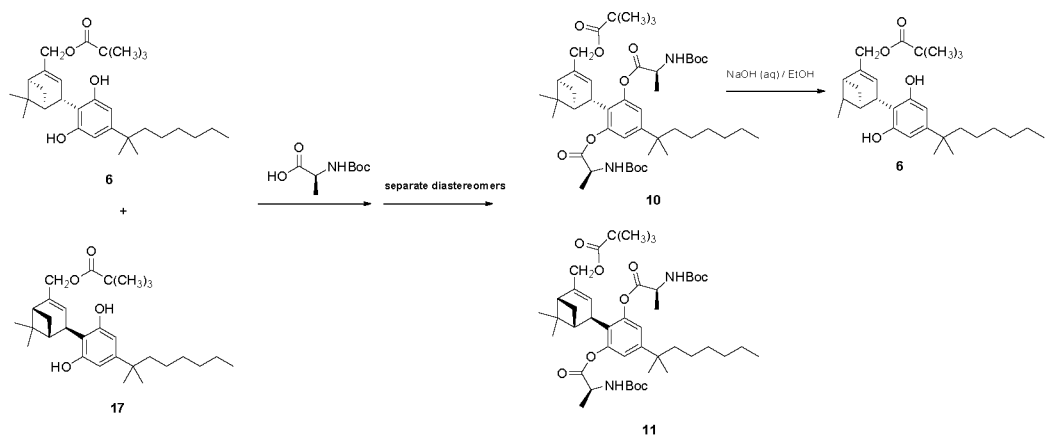
FIG. 13 is a synthetic scheme showing the coupling of Int. 6 and 17 with Boc-alanine to diastereomers 10 and 11 and subsequent hydrolysis to enantiomerically purified Int. 6.

Chiral Resolution of Intermediate 6 Using Boc-Alanine as a Chiral Resolving Agent Referring to FIG. 13, a mixture of compounds 6 and 17, was first converted to their diastereomers by coupling with Boc-L-alanine using DCC/DMAP. The two diastereomers were separated through chromatographic purification on silica gel column. The isolated diastereomer 10 was hydrolyzed under basic condition to obtain the enantiomeric pure Int. 6 (FIGS. 13 and 20).

The Int. 6 (containing the other enantiomer) was coupled with Boc-L-alanine under DCC/DMAP in DCM (20 Vol) at ambient temperature under argon for 1 hour. LC/MS and TLC indicated that the starting material was completely consumed and the major spot is the product with one faint spot for by-product. Since the Rfs for the diastereomer 10 and diastereomer 11 are close, the process development and optimization will focus on column purification of the crude product and re-purification of the impure fractions obtained from the first column.

Different Solvent Systems and Different Ratios of Crude Product Silica Gel (g/g) for Column Purification From 11.5 g of crude product, EtOAc/hexanes (0-11%) with silica gel ratio (1:37.3), and the recovery for the desired diastereomer 10 is 50%. From 1 g of the crude product, EtOAc/hexanes (5-10%) with silica gel ratio (1:40) and silica gel was packed with 5% EtOAc/hexanes, and the recovery for the desired diastereomer 10 is 42%. From 1 g of the crude product, EtOAc/hexanes (isocratic 7%) with silica gel ratio (1:40) and silica gel was packed with hexanes, and the recovery for the desired diastereomer 10 is 42.8%. From 25 g of the crude product, EtOAc/hexanes (5-10%) with silica gel ratio (1:34.6) and silica gel was packed with 5% EtOAc/hexanes, and the recovery for the desired diastereomer 10 is 44%. In a scale up batch, the purification method will be from the combination of trial #1 and trial #4 with some modifications.

Exploration of Stains for Developed TLC Plates:

Since the spots for the diastereomer 10 and diastereomer 11 are very close, a good visualization method for the developed TLC plate is desirable. After screening several stains for developed TLC plates, Ninhydrin was the more effective stain for the two diastereomers.

Figure 14:
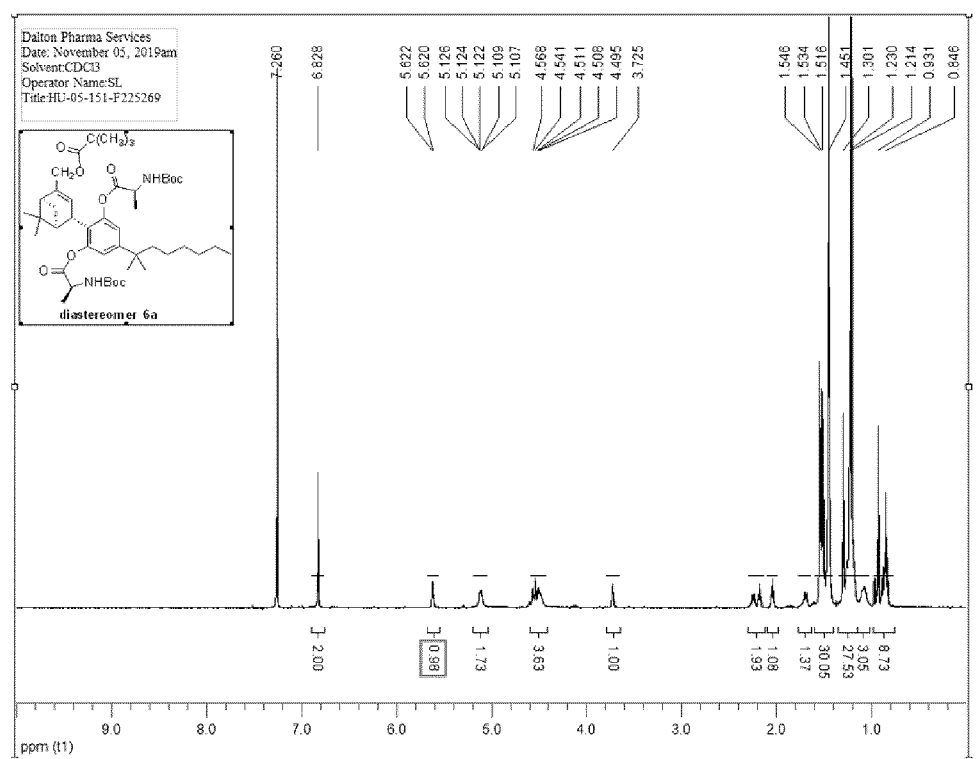
FIG. 14 is a $^1$H NMR of diastereomer 10.

Scale Up the Synthesis of Compound 10 (Step 8):

In a 5 L three neck round bottom flask, equipped with thermometer, overhead stirrer, and argon inlet, Boc-L-alanine (120.85 g, 0.64 mol, 2.2 eq) was dissolved in anhydrous DCM (1 L) under argon. To this solution was added DCC (131.78 g, 0.64 mol, 2.2 eq) in portions. The container was rinsed with anhydrous DCM (350 mL). After stirring for 10 minutes at ambient temperature, a solution of Int. 6 (136.65 g, 0.29 mol, 1.0 eq) in anhydrous DCM (1.3 L) was added while maintaining the temperature at 28-32° C. using a water bath, followed by the addition of DMAP (3.55 g, 0.029 mol, 0.1 eq). The reaction mixture was stirred at ambient temperature for 1 hour. TLC and LC/MS indicated the absence of Int. 6. The solid was removed by filtration, and washed with DCM (2×200 mL). The filtrate was concentrated under vacuum to dryness. The residue was triturated with hexanes (540 mL). After removing the solid by filtration, the filtrate was concentrated under vacuum to dryness to give the crude product 299 g. The crude product was purified on silica get (10 kg) column, and the column was eluted with EtOAc/hexanes (5-14%) under argon pressure (5-10 psi). The fractions which contained the pure diastereomer 10 were combined and concentrated under vacuum to obtain the desired product 149.30 g in 63% yield. ($^1$H NMR in FIG. 14).

Trial reactions for process development and optimization for the hydrolysis of diastereomer 10 to Int. 6 (step 9):

Different bases, solvent combinations, reagent stoichiometry and reaction time were explored for this reaction, and all the reactions were monitored by TLC. The parameters to be optimized and the results are summarized in the Table 11.

TABLE 11

Summary of optimization trials and results

| Reaction No. | Lot No. | Scale | Solvent | Base | Reaction time | Results/comments |
|---|---|---|---|---|---|---|
| 1 | HU-05-25_Na$_2$CO$_3$ | 50 mg | THF-MeOH (4:1 20 Vol) | Na$_2$CO$_3$ (20 eq) | 4 h | No reaction |
| 6 | HU-06-049C | 100 mg | THF-H$_2$O (10:1, 11 Vol) | Na$_2$CO$_3$ (3 eq) | 18-24 hours | No reaction |
| 9 | HU-05-95-6 | 100 mg | NMP-H$_2$O (10:1, 11 Vol) | Na$_2$CO$_3$ (3 eq) | 18-24 hours | No reaction |
| 2 | HU-05-25_LiOH | 50 mg | THF-MeOH (4:1 20 Vol) | LiOH (11 eq) | 4 h | No SM, more by-product |
| 3 | HU-06-049A | 100 mg | THF-H$_2$O (10:1, 11 Vol) | LiOH (3 eq) | 18-24 hours | Product + minor by-product |
| 4 | HU-05-53 | 350 mg | THF-H$_2$O (10:1, 11 Vol) | LiOH (3 eq) | 18-24 hours | 67% yield |
| 7 | HU-05-95-4 | 100 mg | NMP-H$_2$O (10:1, 11 Vol) | LiOH (3 eq) | 18-24 hours | Conversion is good, but NMP is hard to remove |
| 5 | HU-06-049B | 100 mg | THF-H$_2$O (10:1, 11 Vol) | NaOH (3 eq) | 18-24 hours | More effective compared with LiOH and Na$_2$CO$_3$ |
| 8 | HU-05-95-5 | 100 mg | NMP-H$_2$O (10:1, 11 Vol) | NaOH (3 eq) | 18-24 hours | Conversion is good, but NMP is hard to remove |
| 10 | HU-05-109-Rx10 | 100 mg | THF-MeOH (4:1 10 vol) | NaOH (3 eq) | 2 hours | Product + minor by-product |
| 11 | HU-05-109-Rx11 | 100 mg | EtOH (10 vol) | NaOH (3 eq) | 2 hours | Product + less by-product |

The basicity of sodium carbonate may be too weak to hydrolyze the diastereomer 6a in three solvent combinations (THF-MeOH—H$_2$O, THF-H$_2$O, and NMP-H$_2$O). The desired product was obtained under the hydrolysis using LiOH. With more access of LiOH, the hydrolysis proceeded fast, but there was more by-products formed, and a low yield resulted. With 3 eq of LiOH, the hydrolysis proceeded slowly with minor by-product, and the longer reaction time is needed. With 3 eq of LiOH using NMP as solvent, the hydrolysis proceeded smoothly and the conversion is good with less by-product, but NMP is hard to remove even after brine washing for a couple of times.

The desired product was obtained under the hydrolysis using NaOH and the starting material was consumed in 2 hours with less amount of by-product in the two solvent combinations (THF-MeOH—H$_2$O and EtOH—H$_2$O). The scale-up process will follow the parameters: NaOH (3.0 eq) in EtOH—H$_2$O (10:1, 11 vol) and the reaction time is 2 hours.

Intermediary Scale Up Following Preferred Reaction Conditions

Figure 15:
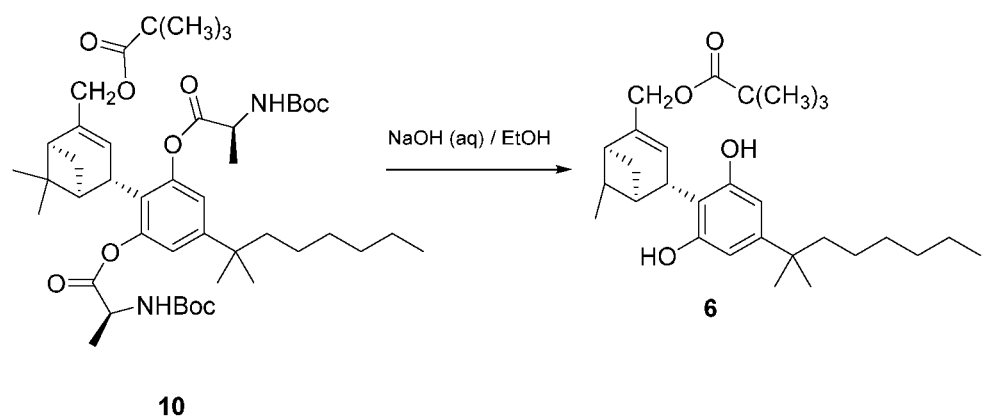
FIG. 15 is a synthetic scheme showing the hydrolysis of diastereomer 10 to intermediate 6.

The hydrolysis step (step 9) was scaled up following the optimized parameters identified from the above trial reactions (FIG. 15). The results are summarized in the Table 12. According to the results from Table 12, it was determined that this process is suitable for scale up with some minor modifications.

TABLE 12

Hydrolysis results from intermediary scale up batches

| Lot No. | Scale | Solvent | Base | Reaction Time | Isolated Yield |
|---|---|---|---|---|---|
| HU-05-111 | 4 g | EtOH—H$_2$O (10:1 11 Vol) | NaOH (3.0 eq) | 1 h | 90% |
| HU-05-149 | 24.25 g | EtOH—H$_2$O (10:1 11 Vol) | NaOH (3.0 eq) | 2 h | 92% |

Scale Up of the Hydrolysis of Diastereomer 10 to Int. 6

Figure 17:
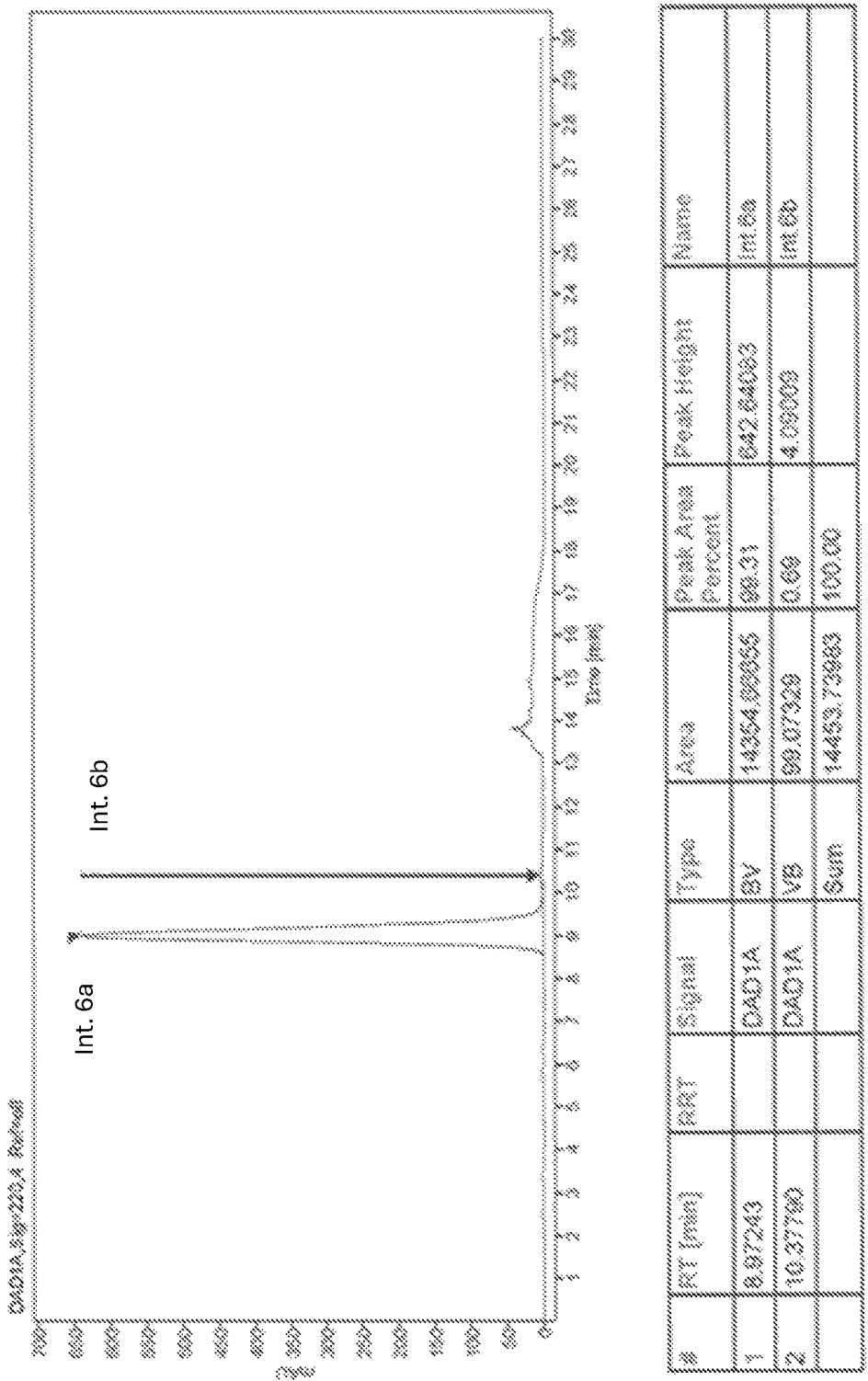
FIG. 17 is a Chiral HPLC chromatogram of Int. 6 after chiral resolution.
Figure 18:
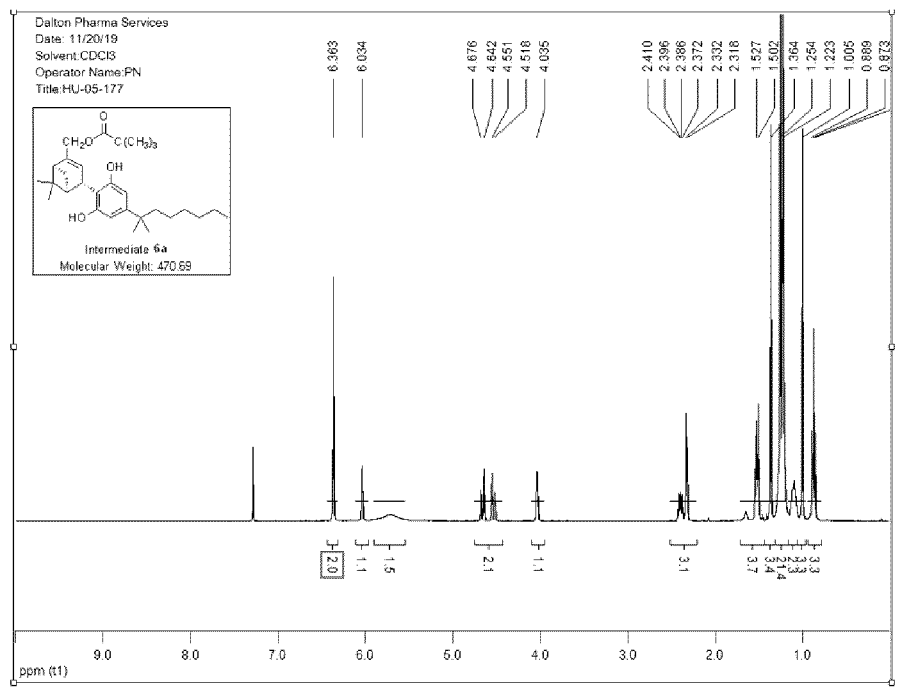
FIG. 18 is a $^1$H NMR of Intermediate 6 after chiral resolution.
Figure 19:
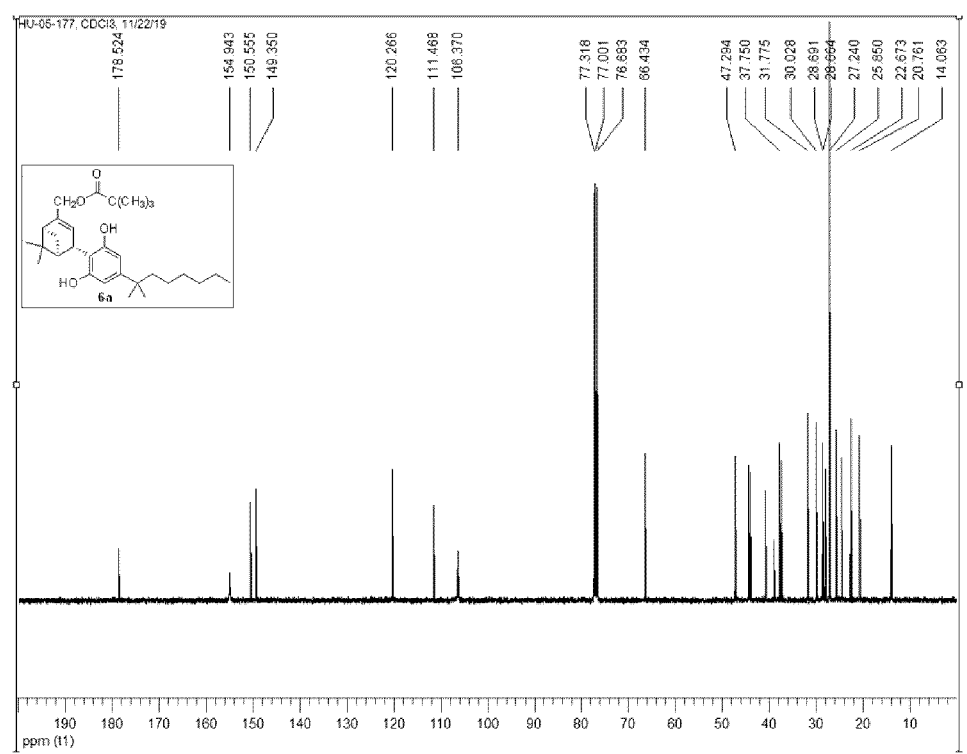
FIG. 19 is a $^{13}$C NMR of Intermediate 6 after chiral resolution.

In a 5 L three neck round bottom flask, equipped with thermometer, overhead stirrer, and addition funnel, diastereomer 10 (151 g, 0.19 mol, 1.0 eq) was dissolved in EtOH (1.5 L). Argon was purged for 25 minutes. The solution was cooled to 11° C. with ice-H$_2$O bath. A NaOH solution (prepared from NaOH (22.29 g) in USP purified H$_2$O (150 mL)) was added drop-wise through the addition funnel while maintaining the temperature at 11±3° C. After the completion of the addition, the cooling bath was remove and allowed the reaction mixture warm up to ambient temperature. The reaction was monitored by TLC (10% EtOAc/hexanes, visualized by UV and I$_2$) and LC/MS. After 2 hours, the reaction mixture was cooled with ice-H$_2$O bath and quenched with 1 M HCl by addition in portions while maintaining the temperature below 15° C. to pH=6. EtOH was removed under reduced pressure with the water bath temperature at 35-40° C. The residue was treated with DCM/H$_2$O (1 L/1 L). The aqueous layer was extracted with DCM (2×500 mL). The combined DCM layer was washed with brine (1×1 L). The DCM layer was dried over Na$_2$SO$_4$ and filtered. The filtrate was concentrated under vacuum to dryness to obtain the crude Int. 6 101.4 g. The crude product was combined with the other two scale-up batches and purified on silica gel column, eluted with EtOAc/hexanes (0-50%) to obtain Int. 6 in 89.8% yield with purity 98.7% by HPLC and 98.63% ee by chiral HPLC. (HPLC chromatogram in FIG. 17, chiral HPLC chromatogram in FIG. 18, $^1$H NMR in FIG. 19 and $^{13}$C NMR in FIG. 20).

Certificates of analysis, characterization data, chiral purity data and spectra of compound 6, HU308 (8) and HU433 (18) can be found in FIGS. 23-25.

Example 3: Synthesis of HU433 (Compound 18)

Figure 26C:
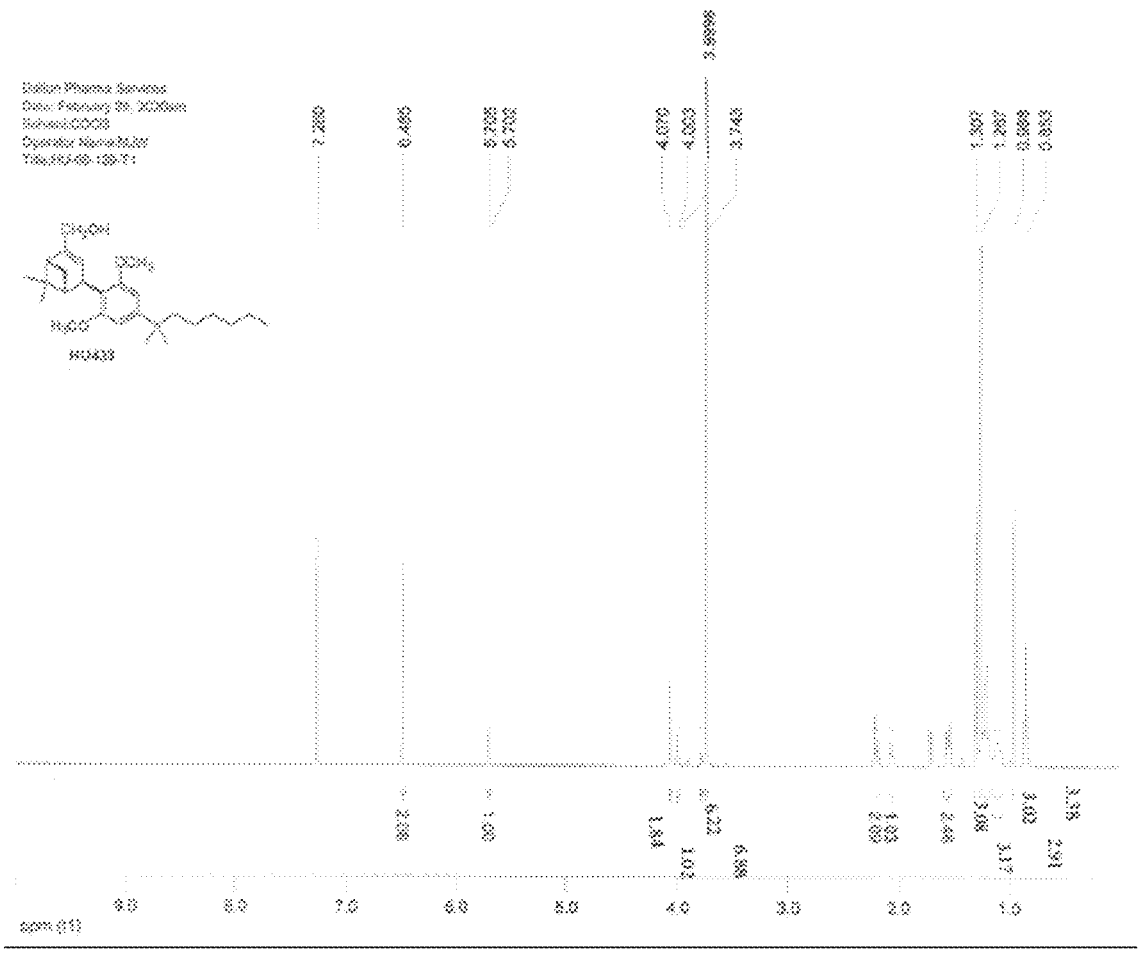
Figure 26D:
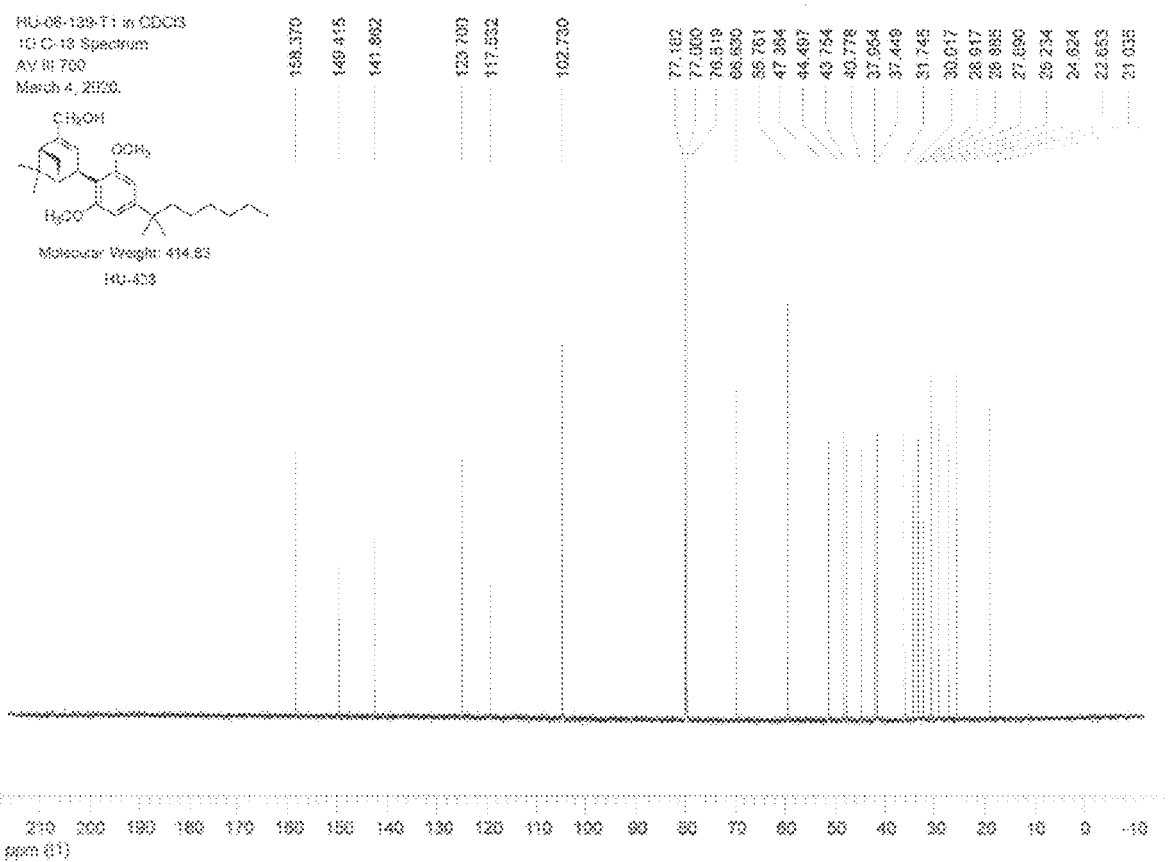
Figure 26E:
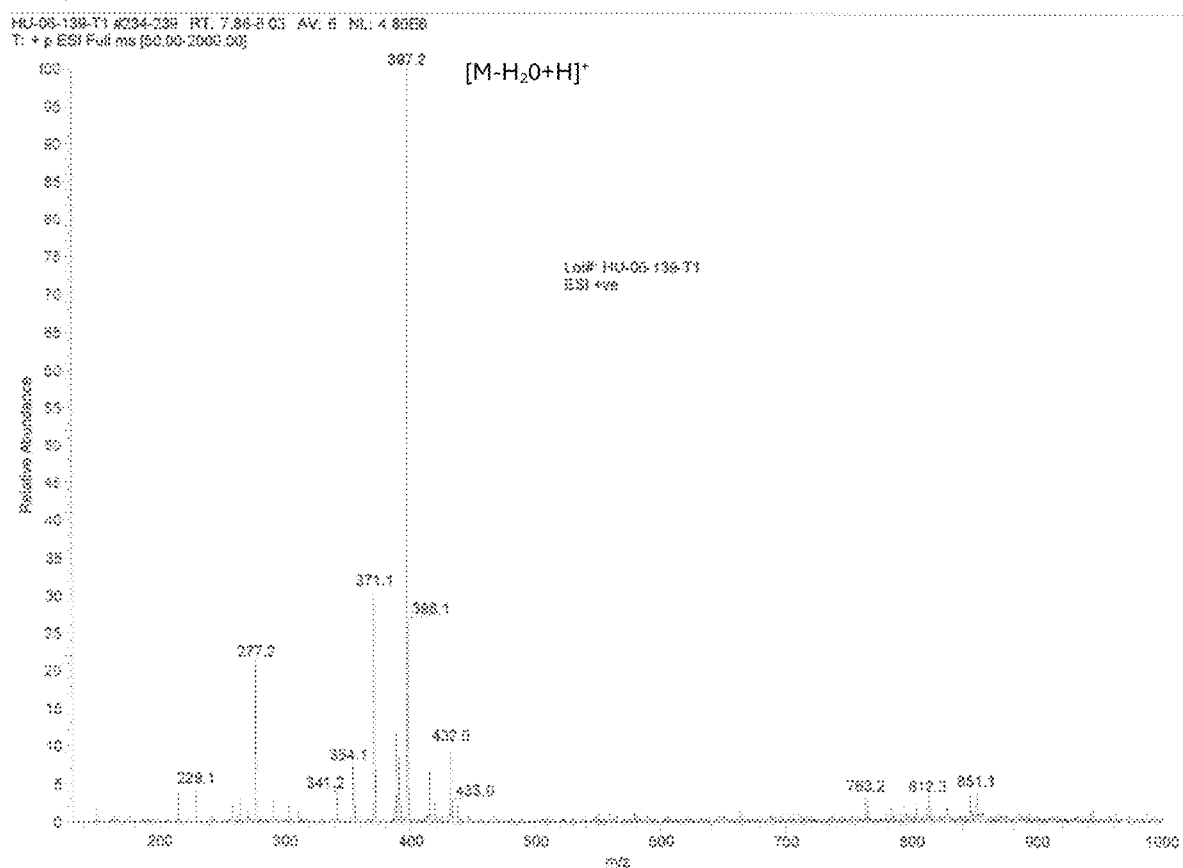
Figure 26F:
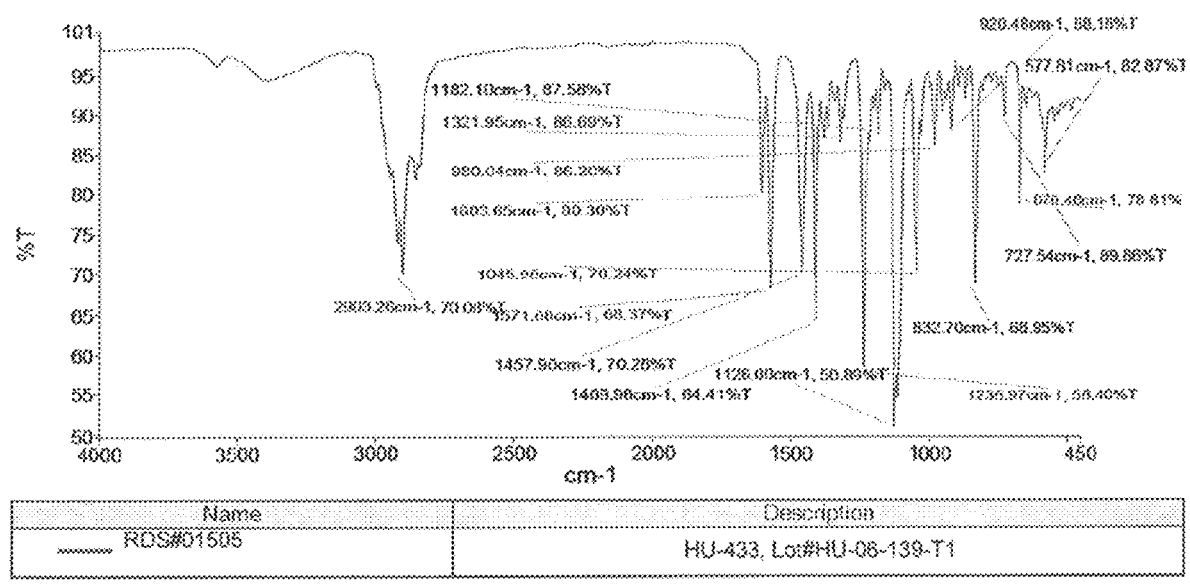
Figure 26G:
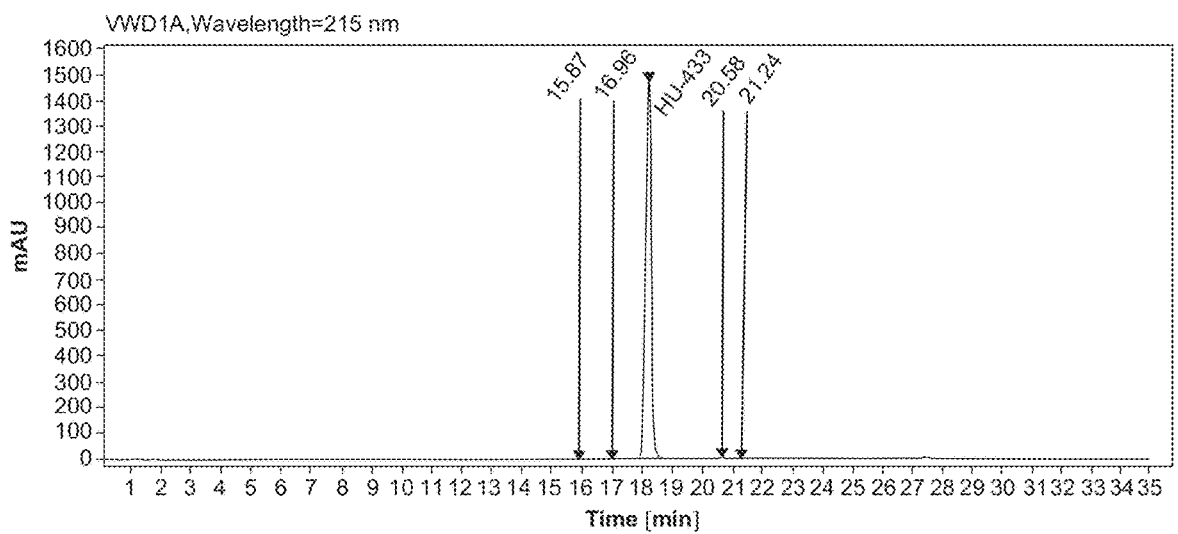
Figure 26G:
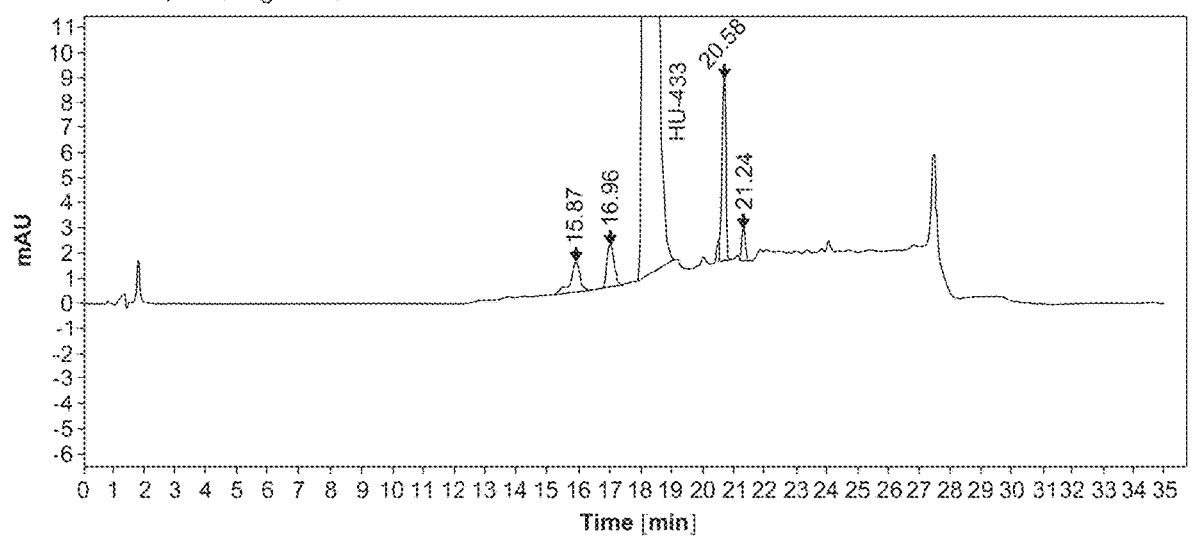

Compound 18 may be synthesized by various methods as described herein. As shown in FIG. 21, compound 18 may be synthesized via methodology that includes a chiral resolution step. Such methodology may be used when optically impure starting materials are used. In such cases, the mixture of diastereomers 6 and 17 may be coupled with optically pure Boc-Alanine, purified by methodology described herein and the enantiomerically purified diastereomer 11 may be hydrolyzed to compound 17 and methylated to yield compound 19. Conditions for the hydrolysis and methylation reactions for HU433 may be the same as the conditions listed for the synthesis of HU308 (compound 8). In some cases, the synthesis of HU433 may resemble FIG. 22 with the addition of a chiral resolution step prior to methylation. In other cases, compound 18 may be synthesized without a chiral resolution step. Such embodiments may be used when starting materials, such as (1R)-(−)-myrtenal, have a satisfactory optical purity. Spectral and optical data for compound 18 is provided in FIGS. 25 and 26. In FIG. 25, compounds 8 and 18 were synthesized using the chiral resolution methodology described herein. FIG. 26B includes chiral data of compound 18 that was obtained using the synthetic route depicted in FIG. 22.

Materials and Methods

Step 8: Reduction of aldehyde 20 to allylic alcohol 21 (FIG. 22)

Figure 27:
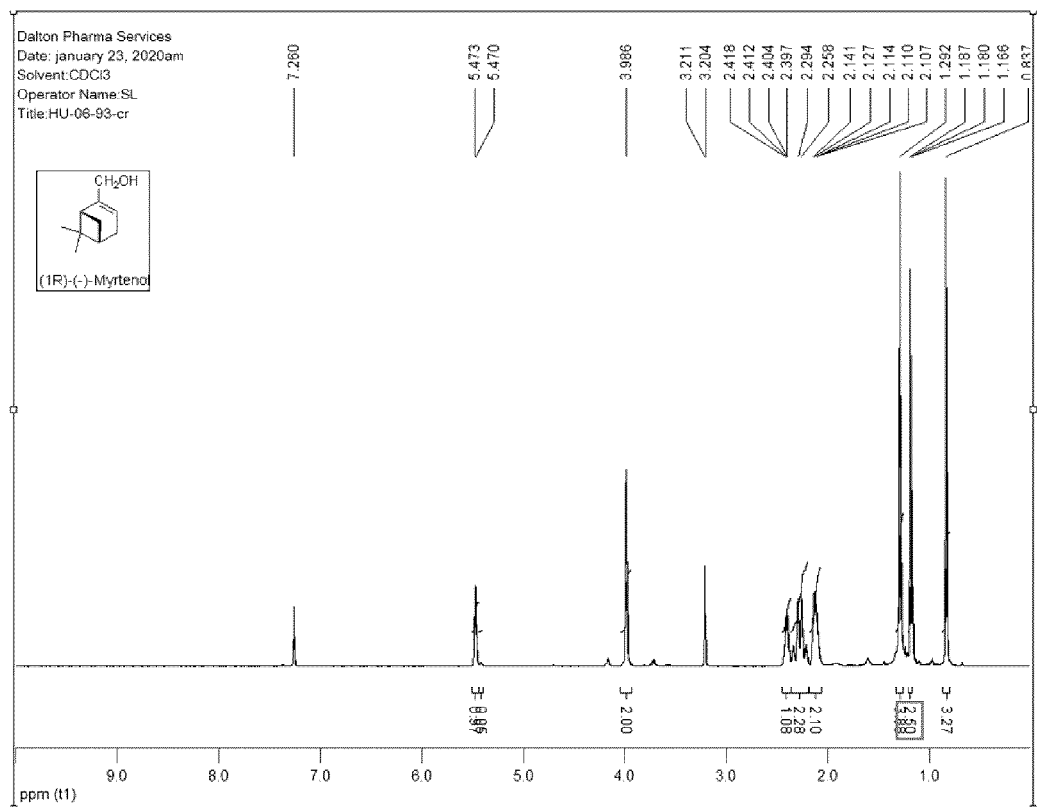
FIG. 27 is a $^1$H-NMR spectrum of Int. 21.

(1R)-(−)-Myrtenal (compound 20) was reduced to (1R)-(−)-Myrtenol (21) with $NaBH_4$. The reaction was carried out starting from 47.6 g of (1R)-(−)-Myrtenal with $NaBH_4$ (1.1 eq) in EtOH (20 vol) following a trial reaction. The desired product was isolated in 49.7 g yield. The $^1H$ NMR spectrum for compound 21 is shown in FIG. 27.

Steps 2-7 in FIG. 22 may be carried out according to the synthetic procedures described herein for the synthesis of HU308.

Example 4: Process Development and Refinement

Figure 28:
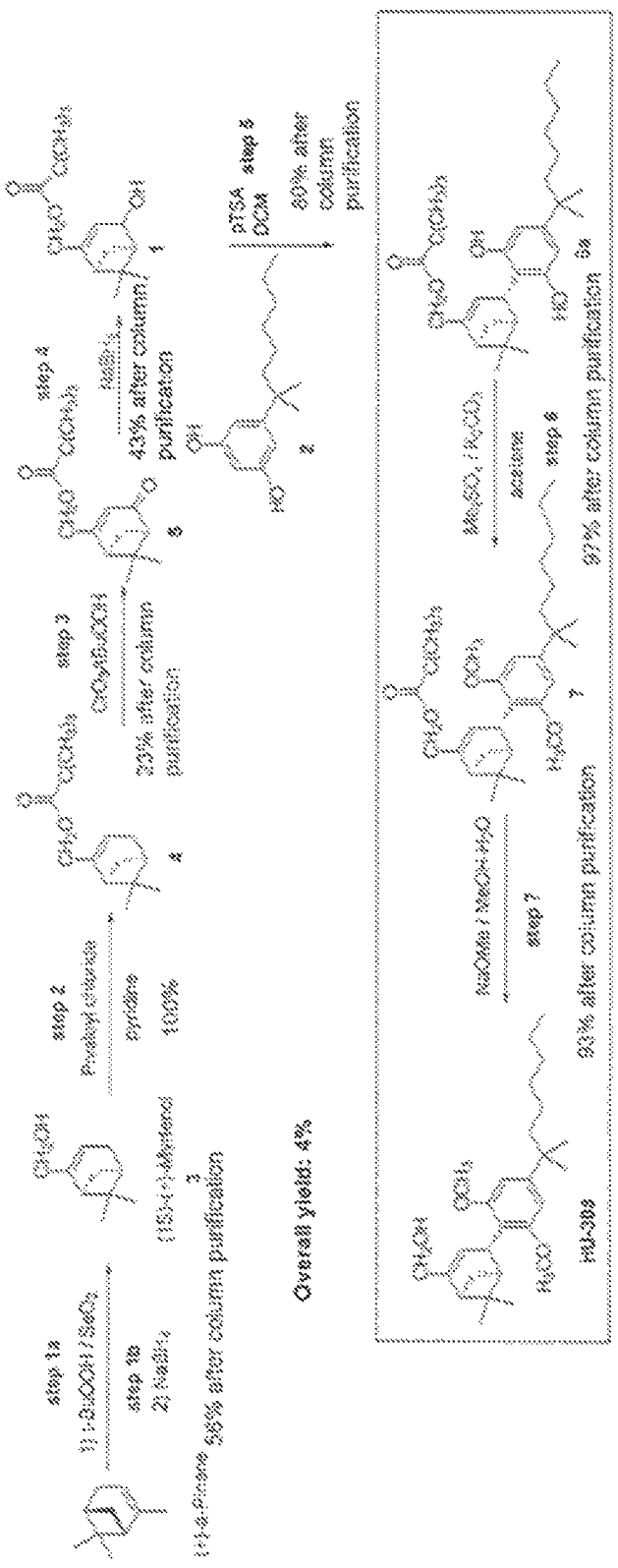
FIG. 28 is a synthetic scheme showing the synthesis of HU308 (compound 8) according to an improved synthetic protocol.

The synthetic scheme with the isolated yields for various steps based on previous batches of HU308 is presented in FIG. 28.

The summary of the synthetic scheme shows that the overall yield for the synthesis of HU308 is relatively low. The process employs silica gel column chromatographic purification for 6 steps out of 7 steps. Step 1a and Step 3 have limitations for scale-up due to safety concerns associated with the large quantity of t-butyl hydroperoxide required for the reaction. To make the process amenable for scale-up, Step 1, 3 and 4 are identified as some problematic steps in the synthesis. Accordingly, process development and enhancement was initiated.

Step 1a and Step 3 are oxidation steps. Both reactions do not go to completion. These oxidation reactions use a large volume of tert-butyl hydroperoxide, which is explosive in nature and requires further safety measures. Although the initial reaction volume was small, both reactions were quenched with large volume of 10% $Na_2SO_3$ to inactivate the excess of tert-butyl peroxide; this also restricts the batch size. After quenching the reaction for both these steps, it was difficult to separate the layers during work-up.

For Step 6, a large amount of $K_2CO_3$ (5.3 eq) was used and the reaction required stirring for approximately 72 hrs. It was noticed that $K_2CO_3$ seizes the stir bar from time to time. If magnetic stirring is replaced with overhead stirring, the reaction does not progress.

Since all the intermediates (products from Step 1 to 4 in FIG. 28) were carried forward to the next step with a number of process impurities and tert-butanol, the reagent stoichiometry and mole equivalents were not adjusted. All reagents were used in excess which made the purification of desired product challenging. Moreover, excess reagents restricted the batch scale up.

Further process development and process refinement was initiated by following a series of steps as indicated below.

Step 1:

A number of trials were carried out for Step 1 to improve reagent stoichiometry, work-up and purification procedures. The Step 1 was developed as follows: The equivalences of tert-Butyl hydroperoxide were reduced to 2.5 from 3.5. The work-up procedure involving emulsion formation was eliminated. The silica gel column purification procedure was further improved. The eluent required for column chromatography was changed to use EtOAc/hexanes plus (EtOAc+ MeOH)/hexanes instead of just EtOAc/hexanes. By introducing the polar solvent MeOH in eluent, the volume of solvents required for purification was significantly reduced.

Since 50 L carboy reactors were used in the Step 1a, approximately 4 kg α-pinene (high optical purity) was split into 6 portions (2×600 g and 4×700 g, SPS-04-19, SPS-04-23 and SPS-04-31) and oxidized in six sub-batches. The 700 g sub batches were scaled-up by about 1.75 times as compared to previous batch size. In terms of total pinene, the scale was doubled in this project.

In this sub-batch work, the tBuOOH was reduced to 2.5 mole equivalents instead of 3.5 mole equivalents. For the extraction of peroxide, the ratio of DCM:70% tBuOOH was increased by 1.49:1 instead of 1.24:1. The other reagents and solvents required for the reaction and quenching were not changed from the previous small-scale batch.

The addition of oxidant or quenching of the reaction was done at low temperature (<25° C.) to prevent possible decomposition of the intermediate. To reduce bi-layer separation, the reaction mixture after quenching (with KOH solution) was diluted with DCM twice and filter through a filter paper using a 24 cm diameter Buchner funnel under vacuum. The filtrate was left undisturbed for few minutes; it did not form the emulsion. Then the bottom layer was siphoned out as the organic layer. The organic layers of the parallel batches were combined as one batch and work up was continued. The crude product from all six sub-batches were combined to make one 4.688 Kg batch. This crude product was taken to next step without any further purification.

The Step 1b was done as single batch starting from 4.688 kg of the crude product from step 1a (reaction→SPS-04-35, purification→PN-03-89) using 0.45 mole equivalent of NaBH4 in 5 volumes of absolute EtOH. It was scaled up 3.3 times as compared to the previous scale batch. Although reaction was done with cooling bath, the internal temperature was maintained below 27° C. and then left to react overnight. The reaction was quenched at temperature below 10° C., with 6% HCl until pH 6. After usual extraction and concentration, 4.06 kg of crude product was obtained. In the previous scale up, about 2.5 kg crude was split into 9 portions and each portion was purified by 2.5 Kg silica gel column under gravity. The crude product from current process was purified in two portions. For this large-scale purification, the 12 kg and 9.5 kg silica gel columns were used and peristaltic pump pressure was used to elute the column. The 10% EtOAc in hexanes was used to elute the starting material, and then a mixture of (10% EtOAc+10% MeOH) in hexanes was used to elute the product. For purification, a total of 271 L eluent were used and about 81.6 wt. % was recovered as product but the purity was not estimated. About 16 wt. % was recovered as mixed product (PN-03-89mix).

Step 2

Step 2 was further scaled to 2.63 times as compared to the previous large-scale batch. About 3.32 kg of Intermediate 3

(reaction→PN-03-93) was reacted with 1.2 mole eq. of pivaloyl chloride in the presence of 1.5 mole eq. of pyridine to form the ester using the previous conditions. It gave 4.67 kg crude product which was purified using 2.14 times silica gel and 151 L of eluent (0-5% ethyl acetate in hexanes). About 78.3% (PN-03-93-P) of the crude weight was recovered as product.

Step 3

Step 3 was enhanced for work-up, stoichiometry and assay quantitation as follows: The organic layer was filtered through a layer of sand to eliminate the emulsion formation during work-up. Also, the assay of isolated Intermediate 5 was determined by q-NMR using 4'-Methoxy acetophenone as internal standard before using for next step.

The Step 3 is (reaction→PN-03-113) an allylic oxidation reaction. Due to scale restriction and safety concerns, the 3.656 kg of Intermediate 4 was split into 5 portions. Each portion was handled in separate 50 L reactor. To reduce the work time, multiple batches were done in parallel: 3 and 2. Each sub-batch was scaled-up 1.66 times as compared to previous batch size. The scale of total crude to be processed in this batch was 1.42 times as compared to the previous batch. The Intermediate 4 was reacted with 5 mole eq. of tBuOOH in the presence of 0.05 mole eq. of $CrO_3$ in 16 volumes DCM.

After overnight reaction, it was quenched with 16 volumes of 10% $Na_2SO_3$ solution at −12° C. (addition over 10 min and stirred for 30 min). After given 30 minutes of separation time, the bottom organic layer was carefully siphoned in portion and filtered through the sand layer. Then the aqueous layer was extracted 3 times with DCM and the extracted organic layers were also filtered through the sand layer. Filtering only the organic layer through sand layer helped to speed up the work and prevented filter clogging. The combined organic layer was washed with brine, dried with $Na_2SO_4$, filtered and the filtrate was concentrated to give 4.0 kg crude product. The crude product was purified by column chromatography using 12 kg silica gel and 95.5 L eluent (0-50% ethyl acetate in hexanes) to give 48% of product and 36% of starting material was recovered.

At this point it was realized that each intermediate carried over up to intermediate 6a was somewhat impure. Although the crude product from each step was purified by silica gel column chromatography, it carried tBuOH and side products of α-pinene. This suggests that excess reagent was used in each step, since the purity of each step was taken as 100%. It was experimentally demonstrated that the impurities in the intermediates did not interfere with next step in the chemistry. In order to check the assay of each intermediate, we used known weight of 4'-Methoxy acetophenone as internal standard with a known weight of the sample in $CDCl_3$ for q-NMR analysis; then we calculated the assay of each intermediate using the q-NMR data and weight information. The ketone (Intermediate 5) and the recovered starting material (Intermediate 4) were analyzed for assay; the assay of intermediate 5 was 47.49% and the assay of the recovered intermediate 4 was 25.35%.

Step 4

Step 4 was improved for silica gel column purification and assay quantitation as follows: 1. The eluent required for column chromatography was changed to use (EtOAc+MeOH)/hexanes instead of EtOAc/hexanes. It significantly reduced the volume of solvents required. 2. The assay of isolated Intermediate 1 was determined by q-NMR using 4'-Methoxy acetophenone as internal standard before using for next step.

The Step 4 (reaction→PN-03-125) is a ketone reduction. The reagents and solvent were calculated based on the assay of Intermediate 5. That is, about 522.4 g of the ketone contained in 1.10 kg bulk was reduced using 1.1 mole equivalent (86.84 g) of $NaBH_4$ in 10 volumes (5.25 L) of absolute ethanol at −13.5 to 2° C. After stirring for 2 hours, the reaction mixture was quenched at −6 to 0° C. using saturated $NH_4Cl$ solution at pH 7. Instead of evaporating the entire reaction mixture, first it was stored in the refrigerator at 2 to 8° C. for overnight and then the white precipitate was filtered out. The filtrate was evaporated at 35° C. to remove EtOH. The residue was extracted as usual using MTBE and water, the MTBE layer was concentrated to offer 0.83 kg of crude product. The crude product was purified by column chromatography using 12 kg silica gel, 176 L eluent (1% EtOAc, 1% MeOH in hexanes to 11% EtOAc, 3% MeOH in hexanes) under solvent pressure created by peristaltic pump. Column fractions containing desired product were combined and concentrated to give 569 g of Intermediate 1 with 60.3% assay by q-NMR using 4'-Methoxy acetophenone as internal standard.

Step 5

The column chromatographic purification for Step 5 was further enhanced as follows: The crude reaction mixture was first purified via a silica gel pad. The impure fractions were combined based on TLC profiles, concentrated and then purified on silica gel cartridge using Biotage with different eluent.

Step 5 is a Friedel-Crafts alkylation. Using the purity information above, intermediate 1 was converted to Intermediate 6a (Reaction→SAP-41-057) using 0.98 mole equivalence of 5-(1,1-Dimethylheptyl)-resorcinol (Intermediate 2) in the presence of catalytic amount of p-TsOH (0.1 mole eq.) in 35 volumes of anhydrous DCM. In this reaction, first the p-TsOH $H_2O$ was dehydrated via co-evaporation with 2×3.2 volumes of toluene at 60° C. The dry catalyst and 5-(1,1-Dimethylheptyl)-resorcinol were dissolved in 25 volumes of anhydrous DCM. To this solution, alcohol (intermediate 1) in 10 volumes of anhydrous DCM was added dropwise over 1 hour. After 2.5 hours of stirring, the reaction mixture was quenched with 4.4 volumes of 5% $NaHCO_3$ solution. After usual workup and evaporation, 1529 g of crude intermediate 6a was obtained. In the previous batches, Int. 6a was purified using large column with pressure exerted by solvent pump (peristaltic pump). But large columns took longer time to elute the product. It was suspected that the product may decompose in silica gel if it stays on silica gel for long period. So, it was decided to use short silica gel flash columns for this batch to isolate most of Int. 6a quickly. Then the impure portions were combined based on their TLC profiles and re-purified with Biotage flash column.

The crude was split into 7 portions. Each portion was dissolved in 1 volume of DCM and loaded onto a column (5 L sintered glass funnel) packed with 2.5 kg silica gel in hexanes. The column was eluted with 8.85 volumes of hexanes, then 226 volumes of 2% ethyl acetate in hexanes. Fractions were collected as 1 L portion. According to TLC profile, the fractions were pooled in 3 different portions: top impurities+Product, Product and Product+bottom impurities. This flash column gave significant portion as pure product.

During the purification of both: top impurity+product and product+bottom impurity, many different solvent combinations were evaluated to achieve efficient purification. One method for purification of top impurity+product and another method for product+bottom impurity were found. To purify the top impurity+product portion, silica gel 1.6 kg silica cartridge packed in hexanes was loaded with a solution of 172 g sample in a solvent mixture containing 1 volume DCM and 2 volume hexanes. The sample loading was under gravity. The column was eluted with isocratic eluent 0.5% EtOH/2% acetone in hexanes on Biotage with a flow rate of 300 mL/min. After top impurity was removed from the column, the product was flushed out using 100% acetone. The fraction containing product were concentrated and stored in the freezer. Then the column was recovered by washing with 2 CV acetone and equilibrated with 1 CV of hexanes.

Similarly, the product+bottom impurity was purified except that the column was eluted with isocratic eluent of 0.5% acetone/2% EtOAc in hexanes on Biotage. After product was carefully eluted, the product fractions were evaporated as before and stored in the freezer. The bottom impurity from the column was flushed out with 100% acetone. Then the column was recovered by washing with 2 CV acetone and equilibrating with 1 CV hexanes.

All pure portions containing intermediate 6a were dissolved in DCM, consolidated, evaporated and dried to get 646 g of intermediate 6a with 97.0% purity. It was split into 3 different portions: First 290 g portion for Engineering batch, next two portions (101.46 g and 253.93 g) for GMP batches for the synthesis of HU308.

Step 6

Step 6 was enhanced for stirring efficiency to increase the rate of reaction as follows: Glass beads (6 mm diameter, 400 g) were introduced for the reaction to help with the grinding of $K_2CO_3$.

Step 6 involves methylation of intermediate 6a with dimethylsulfate using solid potassium carbonate as base. A 400 g of intermediate 6a was processed in R&D batch (PN-03-135). For this batch size, we decided to use overhead stirrer fitted with Teflon coated stir rod. After two days of stirring, desired product was not observed though monomethylated intermediate and the starting material intermediate 6a were present. It was thought that the reaction requires constant grinding of $K_2CO_3$. So, we introduced magnetic stirrer and Teflon coated magnetic stir bar. When the magnetic stirrer was used alone, the solid $K_2CO_3$ seized the stir bar. Therefore, a combination of both stirring methods was used: magnetic stirrer at 400 rpm and overhead stirrer at 50 rpm. On 3rd day, desired product was observed though mono-methylated intermediate was major component in reaction mixture. So, another 40% reagents ($Me_2SO_4$ and $K_2CO_3$) were added. On 4th day, intermediate 6a was not detected; the desired product was the major component though mono methylated compound was still present in significant amount. At this stage, we decided to introduce the glass beads (6 mm diameter, 400 g) to help with the grinding of $K_2CO_3$ (also introduced 80% more pre-powdered $K_2CO_3$). It was noticed the reaction was completed on the 5th day. For the next engineering batch, we introduced both stirring techniques and glass beads without adding excess reagents.

The engineering batch (SAP-41-065) was 2.9 times scale-up as compared to previous scale. About 290 g of intermediate 6a was reacted with 4.0 mole equivalents of dimethyl sulfate in the presence of 5.3 mole equivalents of $K_2CO_3$ in 20 volumes of acetone. To have better mixing and grinding of the $K_2CO_3$ during the reaction, a combination of magnetic stir bar, 6 mm diameter glass beads and overhead stirrer were used. (Glass beads to help with grinding of $K_2CO_3$, magnetic stir bar to move the glass beads and overhead stirrer to prevent the magnetic stir bar being seized by solids). This system improved the rate of reaction. The reaction was complete in 46 hours and 24 minutes rather than 72 hours. The reaction mixture was filtered and filtrate was concentrated to remove the acetone. The residue was mixed with water and extracted using MTBE. After washing the organic layer with brine and drying over $Na_2SO_4$, the organic layer was evaporated to remove MTBE. It gave 564 g of crude product. The crude was purified by silica gel column chromatography. For this purification, glass column was packed with 25 times silica gel in hexanes. The crude was dissolved in one volume hexanes and was loaded on column; and eluted with 0 to 1.2% EtOAc in hexanes using peristaltic pump at flow rate of 700 ml/min. The column chromatographic purification required about 155 L solvent. After monitoring column fractions by TLC, the product fractions were combined and evaporated to get 277 g of intermediate 7. It was taken to next step as is.

Step 7

The TLC visualization for Step 7 was enhanced as follows: The developed TLC plates were visualized using PMA instead of iodine vapor. PMA shows more intense spots as compared to iodine vapor as a visualizing agent.

The Step 7 is hydrolysis of pivalate ester to form HU308. The R&D batch had been previously scaled to 4.2-times scale. This engineering batch was scaled to 2.9 times. Both batches were done with same ratios of reagents and volumes solvents and reaction conditions; except the reaction time for R&D batch was about 24 hours and for engineering batch was 48 hours. Since both scales were successful, we discuss the engineering scale (SAP-41-165). Approximately 276 g of intermediate 7 was dissolved in 20 volumes of methanol and 0.796 volumes of water. To this mixture, 9 moles equivalents of NaOMe (25% w/w in MeOH) was added and reaction mixture was stirred for 48 hours under argon at 37° C. After completion of the reaction, it was neutralized to pH 6-7 using acetic acid at <10° C. temperature and evaporated to remove methanol.

The residue was mixed with water and extracted using ethyl acetate. The extracted organic layer was washed with saturated bicarbonate to remove excess acetic acid, then brine to remove excess water. After drying over $Na_2SO_4$ and filtration, the organic layer was evaporated to remove ethyl acetate. The crude was purified by column chromatography using 10.5 times of silica gel in 3% ethyl acetate/hexanes packed in a large glass column. The crude sample was loaded onto the column then the source bottle was rinsed with 2×0.5 volumes of 3% ethyl acetate/hexanes and loaded. The column was eluted with 3-10% ethyl acetate in hexanes using peristaltic pump with 700 ml/min flow rate. Approximately 80 L solvent was used. For this batch, the column fractions were analysed by TLC (the fraction was spotted on silica gel on glass plate and developed with 20% ethyl acetate/hexanes). The developed TLC plates were visualized using PMA instead of iodine vapor. PMA shows more intensive spots than iodine vapor. The pure product fractions were pooled and evaporated. The residue after evaporation was re-dissolved in 1.6 volumes of DCM and filtered through medium frit sintered glass funnel to remove and physical particles. The filtrate was evaporated using 10 L evaporation flask on large rotary evaporator to minimize the foaming of the product under vacuum. The product residue was co-evaporated with 4×2 volumes of hexanes to remove any residual DCM (In the R&D batch, DCM was used to co-evaporate to remove hexanes). After a brief drying under high vacuum, the product (244 g) was ready for hydration. It was thick viscous oil at warm temperature.

The hydration was done in the same rotary evaporation flask to prevent the physical loss of the product during transfer. The thick oily product was mixed with 10 volumes of USP water and stirred vigorously using magnetic stir bar and stirrer under argon. After 12 hours, the product solidified as a block and stir bar seized. The supernatant was decanted into a clean vessel and the block solid was broken into pieces. Each solid piece was grinded using pestle and mortar. The fine solid was transferred back into the flask and mixed with decantate. This mixture was stirred for an additional 24 hours and filtered through medium frit sintered glass funnel. Solid was rinsed with 1.6 volumes of fresh USP water. The solid was air dried on the filter under vacuum suction for 2 hours. The solid was further dried in the high vacuum oven at room temperature for overnight. The solid was sieved through a 1.00 mm sieve to obtain 211.05 g of HU308.

Conclusions: We have successfully performed further process development and refinement, and purification development for some problematic steps in the scale-up synthesis of HU308.

We have successfully accomplished the following synthesis following an improved procedure: R&D batch for the synthesis of 282 g of HU308 (L) PN-03-143. Engineering batch for the synthesis of 208 g of HU308 (L) SAP-41-065. GMP HU308 API raw material: Synthesis of 105 g and 355 g of HU308 Intermediate 6a (L) PN-03-149 and (L) SAP-41-063 respectively.

Protocol for the Improved Synthesis of HU308

Step 1. Synthesis of Intermediate 3

Allylic Oxidation (Oxidation Reaction SPS-04-23)

The 70% t-butyl hydroperoxide (1760 mL, 12.84 mol, 2.5 eq) was extracted with 2630 mL DCM. The organic layer (after discarding aqueous layer) was transferred into a 50 L four necked bottle reactor equipped with an overhead stirrer, Teflon stir rod with blade, condenser, thermocouple with temperature monitor and addition funnel. To this reactor, $SeO_2$ (20.5 g, 0.18 mol, 0.036 eq) was added. The reaction mixture was stirred at ambient temperature for 35 minutes. This reaction mixture was cooled using ice/water bath to about 11° C.

To the above cold mixture, α-Pinene (700 g, 5.14 mol, 1.0 eq) was added dropwise via the addition funnel over 120 minutes while maintaining temperature at 22-31° C. The reaction mixture was stirred at ambient temperature for 41.75 hours. TLC (hexanes, visualized by UV and $KMnO_4$) indicated the absence of starting material. To the reaction mixture, 10% KOH (2600 mL) was added while maintaining the temperature below 27° C. The mixture was an emulsion and took longer time to separate. So, the emulsified mixture was diluted twice with DCM and filtered through a filter paper (using Buchner funnel and filter flask) under vacuum. The filter flask was kept under suction until the filtrate solution gave clear separate layers. The organic layer was carefully siphoned out using a siphoning tube, filter flask and vacuum pump. The separated organic layer was washed with 750 mL of brine. Peroxide test showed positive result. The organic layer was stirred with 600 mL of 10% $Na_2SO_3$ solution for 1 hour and peroxide test was found to be less than 3 mg/mL. The organic layer was separated and washed again with 750 mL of brine, and then dried over $Na_2SO_4$ and filtered; the filtrate was concentrated under vacuum to dryness to obtain 820.4 g of yellowish oily residue (A total 4688 g of crude oxidized product was obtained from 4 kg α-Pinene).

Reduction of Aldehyde (Reduction Set-Up SPS-04-35, Purification PN-03-89)

The oily residue was transferred to a 4 necked 50 L bottle reactor and dissolved in dehydrated 20 L of EtOH (4.27 volumes) under argon. The solution was cooled with ice/water bath. To this solution $NaBH_4$ (499.85 g, 13.21 mol, 0.45 eq) was added in portions while maintaining internal temperature below 24° C. The reaction mixture was stirred overnight while the temperature was allowed to gradually increase to ambient temperature. The completion of reaction was confirmed by TLC (10% EtOAc/hexanes, visualized by UV and $KMnO_4$). No UV active spot was seen confirming the consumption of aldehyde. The reaction mixture was cooled with ice-water bath to 7.6° C. and the reaction was quenched with 8 L of 5% HCl by dropwise addition to maintain the temperature below 12.1° C. After the reaction mixture reached pH 6, it was evaporated at 37° C. bath temperature to get 4.055 kg orange colored oil.

The crude product was purified by silica gel column chromatography. A glass column (D=18 cm; H=135 cm) was packed with 24 L hexanes+12.5 kg silica gel and equilibrated overnight. To this column, 2.355 kg crude in one volume of hexanes was loaded using peristaltic pump. Then, the column was eluted with 12.5 L of each of the following eluents in sequence: 4, 5, 6, 8, 10% EtOAc in hexanes. Then, each 12.5 L of 10% EtOAc in hexanes, eluent polarity was increased using methanol as following: 2, 4, 5% methanol. Finally, the column was eluted with 25 L of 10% MeOH/10% EtOAc in hexanes. Fractions were analyzed by TLC (The fraction was spotted on silica gel on glass; developed with 10% EtOAc in hexanes; visualized with DNP for top spots and $KMnO_4$ for product spots). Appropriate fractions were combined and evaporated. Similarly, the remaining 1.7 kg crude was purified using 9 kg silica gel column by scale down. The combined product portions from both columns were co-evaporated with 3×1 L heptane at 35° C. and vacuum dried to get 3.31 kg of Intermediate 3 ((1S)-(+)-Myrtenol) (L) PN-03-89-P as yellow oil. The structure of Intermediate 3 was confirmed by $^1$H-NMR. The top impurity plus the mix fraction were combined and evaporated to get 0.64 kg yellow oil.

Step 2. Synthesis of Intermediate 4 (Reaction Set-Up PN-03-93, Work Up SPS-04-47, Purification PN-03-99)

A 50 L bottle reactor was placed in a plastic container and equipped with Argon inlet and outlet, thermocouple with temperature monitor, air condenser and addition funnel. After flushing the reactor with argon for 30 min, (1S)-(+)-Myrtenol (intermediate 3) (3.31 kg, 21.74 moles) was taken with 16 L (4.8 volumes) of anhydrous DCM. To this solution, anhydrous pyridine (2.63 L, 32.6 moles, 1.5 eq.) was added and contents were stirred at 170 rpm while cooling below 0° C. using dry ice/IPA bath. To this cold solution, pivaloyl chloride (1.0 L, 26.09 moles, 1.2 eq.) was added dropwise over about 40 minutes while maintaining the internal temperature below 0° C. While reaction mixture was gradually warming up to ambient temperature, the reaction mixture was stirred overnight. The reaction was monitored by TLC (spotting on silica gel on glass plate; developing with 10% EtOAc in hexanes; PMA visualization). After starting Myrtenol disappeared, the reaction mixture was quenched with 10 L of USP water below room temperature. The bilayer was separated. The aqueous layer was back extracted with 2 L DCM. The combined organic layer was washed with 5.2 L of 0.5 M HCl solution. The acidic aqueous layer was back extracted with 2 L DCM and combined with main organic portion. The organic portion was washed with 5 L brine. The organic layer was separated and dried over $Na_2SO_4$ and filtered. The filtrate was evaporated at 35° C. bath temperature to obtain 4.67 kg of crude Intermediate 4 which was purified by column chromatography.

A 30 L glass column was packed with 10 kg silica gel in hexanes. The above crude intermediate 4 was dissolved in hexanes (18.5 L) and loaded using peristaltic pump. The column was eluted by pumping eluents using peristaltic pump. Eluents were 41 L of hexanes (16 L recycled hexanes) and 20 L of 0.5% EtOAc in hexanes. The next 5 eluents were 10 L each by increasing the polarity from 1 to 5%. Fractions were collected in the 4 L bottles. Fractions were pooled according to TLC profile. The combined fractions were concentrated to obtain 3.656 kg of Intermediate 4 (L) PN-03-93-C1P as yellow oil. The structure of Intermediate 4 was confirmed by $^1$H-NMR.

Step 3. Synthesis of Intermediate 5 (PN-03-113)

The purified Intermediate 4 from the Step 2 was split in 5 equal portions and carried forward for allylic oxidation. First 3 batches were done in parallel and then remaining 2 batches were done in parallel. For each reaction, a 50 L bottle reactor was assembled in the plastic tub with overhead stirrer and Teflon stir rod with blade. For each reactor, $CrO_3$ (15.47 g, 0.155 mol), 5 L DCM and 2.1 L t-BuOOH were added and stirred at room temperature at 300 rpm for 30 minutes. To this mixture, Intermediate 4 (731.2 g, 3.094 moles) dissolved in 5.85 L of DCM was added in small stream over 14 minutes. The reaction mixture continued to stir overnight.

The reaction was monitored by TLC (spotting on silica gel on glass; developing with 10% EtOAc in hexanes; PMA visualization). When most of the starting material disappeared, the reaction mixture was cooled with dry ice/IPA to −12° C. and then was quenched by pouring 11.7 L of 10% $Na_2SO_3$ solution for 10 minutes and stirring for 30 minutes. After bi-layer separation, the organic layer was carefully siphoned and filtered through a pad of sand layer. The aqueous layer was back extracted with DCM (3×2 L). The back extracts were also filtered through the sand pad. The filtrate was washed with 6 L brine. The organic layer was dried over $Na_2SO_4$, filtered, and concentrated by rotary evaporation. The crude from five sub reactions was combined to obtain 4.0 kg of crude Intermediate 5 (L) PN-03-113-Cr. It was purified by column chromatography.

A 30 L glass column was packed with 12 kg silica gel in hexanes. The crude product was dissolved in 13 L hexanes and loaded on to the column using peristaltic pump. The eluents were pumped using peristaltic pump to elute the column. The eluents were 24 L hexanes (first 6×4 L recycled hexanes), 12 L 5% EtOAc hexanes, 12 L 10% EtOAc hexanes, 12 L 20% EtOAc hexanes and 35.5 L 50% EtOAc hexanes. The 4 L column fraction was collected. Fractions 7 to 10 containing recovered starting material were combined and evaporated to get 1446 g of the recovered intermediate 4 (PN-03-113-RecSM). Fractions 11 to 25 contained product; they were combined and evaporated to get 1917 g of intermediate 5 as yellow oil (PN-03-113-Prod, assay: 47.49%). The recovered starting material was re-oxidized to give an additional 548 g of intermediate 5 (PN-03-119-Prod, assay: 19.96%) and 742 g (comprising impurities that increased substantially) of recovered starting material (PN-03-119-RecSM, this material was no longer useful for oxidation). The structure of Intermediate 5 was confirmed by 1H-NMR.

Intermediate 5 from various batches were combined: (L) PN-03-113-Prod (800 g), (L) PN-03-119-Prod (548 g), SAP-41-029-C2P (90.2 g) and SAP-41-029-C1P (126.85 g). The assay of combined intermediate 5 (L) SAP-41-045-SM was 38.50% by q-NMR.

Step 4. Synthesis of Intermediate 1 (SAP-41-045)

The starting material (Intermediate 5) for this step is not pure. According to the q-NMR using 4'-methoxy acetophenone as an internal standard, the assay for the staring material is 36.23%. The reagent stoichiometry for this step was adjusted based on q-NMR Assay value. The reaction was setup as follows: in a 50 L bottle reactor, 1478 g of intermediate 5 (L) SAP-41-045-SM (assay: 38.5%) (ketone 569 g, 2.27 moles) was dissolved with 5.7 L (10 volumes) of abs. EtOH under argon. The stirred solution was cooled to −24.4° C. using dry ice/IPA bath. To this cold solution, $NaBH_4$ (94.46 g, 2.50 moles, 1.1 eq.) was added in portions over 106 minutes by maintaining the internal temperature below −16.4° C. After stirring for 2 hours, the reaction was monitored by TLC (spotting on silica gel on glass; developing with 20% EtOAc in hexanes; UV then PMA for visualization). The reaction mixture was quenched with 4.1 L of saturated $NH_4Cl$ solution (addition of first 500 mL was slow then addition in a small stream) until pH reached to 5.5. The milky solution was stored in the fridge for overnight. The reaction mixture was filtered using 24 cm diameter filter paper and Buchner funnel. The solid was rinsed with 3×500 mL MTBE. The combined filtrate and rinse volume were evaporated at 35° C. bath temperature under reduced pressure. The evaporated crude product was mixed with 2.6 L of saturated brine and 3.3 L of MTBE. The bi-layer separated; the aqueous layer was further saturated and back extracted with 1 L MTBE. The combined extract and back extract were dried over 300 g of $Na_2SO_4$ and filtered. This mixture was filtered through silica bed (2.5 L volume of silica gel in 5 L sintered glass funnel in hexanes solvent). Fraction was collected in 1 L portions. After loading all the crude mixture onto the column, the silica bed was rinsed with MTBE to elute the entire product from the silica gel. A total of 18 fractions were obtained. Fraction 2 to 12 contained product and some impurities. The consolidated product containing fractions were rotary evaporated at 35° C. bath temperature under reduced pressure. The crude product was further dried for another 3.5 hours under high vacuum to give 1.158 kg of Intermediate 1 (L) SAP-41-045 as amber oil with 35.7% assay, determined by q-NMR using 4'-methoxy acetophenone as internal standard.

Step 5. Synthesis of Intermediate 6a (SAP-41-057)

A 4 necked 22 L round bottom flask was placed into a plastic container. This flask was equipped with overhead stirrer, Teflon stir rod with blade, thermocouple with temperature monitor, argon inlet and outlet. The assembled reactor was flushed with argon for 30 min. In a separate single necked 3 L flask, p-TsOH (31.82 g, 0.167 moles, 0.102 eq) was taken and co-evaporated with 2×1.8 L of anhydrous Toluene at 60° C. under vacuum. This p-TsOH solid was transferred into the 22 L reactor using 5×1 L anhydrous DCM. To the reactor, a solution of 5-(1,1-Dimethylheptyl)-resorcinol (379.30 g, 1.60 moles, 1.0 eq.) in 5.3 L of anhydrous DCM was added and the reaction mixture was stirred for 30 minutes at room temperature under argon. In a 10 L bottle, Intermediate 1 (413.06 g (or 1125.02 g with assay 35.67%), 1.64 moles, 1.02 eq.) was dissolved in 4.1 L of anhydrous DCM and poured into the reactor over 4 minutes. The reaction mixture was stirred for 1 hour and 38 minutes at room temperature under argon. The reaction was monitored by TLC (sample "as is" spotted on silica gel on glass plate; developing with 20% EtOAc in hexanes; PMA visualization). After disappearance of 5-(1,1-Dimethylheptyl)-resorcinol, the reaction mixture was quenched with 1.8 L of 5% $NaHCO_3$ solutions. The bilayer separated after stirring for 5 minutes. The organic layer (bottom layer) was washed with another portion of 1.8 L of 5% $NaHCO_3$ solution. The combined aqueous layers were back extracted with 2×500 mL reagent grade DCM. The combined organic layers were washed with 2 L of saturated brine. The organic layer was dried over 300 g of $Na_2SO_4$ and filtered. The filtrate was rotary evaporated at 35° C. bath temperature to obtain 1529 g of crude Intermediate 6a which was purified by column chromatography in seven portions.

Purification of Crude Intermediate 6a:

For purification of each portion, 5 L sintered glass funnel packed with 2 kg silica gel in hexanes was used to purify crude Intermediate 6a. Each column was loaded with about 218 g of crude Intermediate 6a dissolved in 0.5 volume of DCM in hexanes under gravity. Then the column was eluted with 2 L hexanes followed by isocratic elution using 2% EtOAc in hexanes. It is a flash column using vacuum suction with semi dry (loaded 1 L eluent and removed by suction 1 L fraction at time). Column fractions were pooled according to TLC profile (spotting on silica gel on glass plate; developing with 10% EtOAc in hexanes; PMA visualization) and concentrated to obtain pure Intermediate 6a. The impure fractions containing product were combined based on their TLC profile and repurified by Biotage.

Typical re-purification of impure column fractions containing Top impurity and product using Biotage system: (PN-03-185).

A 1.6 kg silica gel cartridge equilibrated with hexanes was used to repurify. The 172 g of impure sample was dissolved in a mixture of solvents –170 ml of DCM and 340 mL Hexanes. One half of the solution was loaded onto the column under gravity (2nd half was stored in the fridge 2-8° C. until use) and eluted with 0.5% EtOH; 2% acetone in hexanes. Once the top impurity was removed, the column polarity was increased to 100% acetone to flush out the product. The column was recovered by washing with 2 CV of acetone followed by 1 CV of hexanes. The column purification was repeated for the 2nd half solution.

Typical re-purification of impure column fractions containing Bottom impurity and product using Biotage system: AAT-11-83

A 1.6 kg silica gel cartridge was equilibrated with hexanes and loaded with sample solution of product like previous operation. It was eluted with 0.5 acetone; 2% EtOAc in hexanes until all products came out. Then column was recovered by flushing with 2 CV of acetone followed by 1 CV hexanes.

The fractions containing pure product were combined and rotary evaporated at 35° C., co-evaporated with 3×1 volumes DCM and dried on high vacuum (warning→foam forms during the drying process). Each column chromatography purified product was analyzed by HPLC and the product batches which passed the purity limits were dissolved in DCM and combined to make one batch. This product solution was concentrated at 35° C. and dried under high vacuum to give 646 g (83.54% yield) of Intermediate 6a (L) SAP-41-063 as a sticky amber solid (at cold temperature, it is breakable hard solid). The structure of Intermediate 6a was confirmed by $^1$H-NMR.

Step 6. Synthesis of Intermediate 7 (SAP-41-065) (Engineering Batch)

In a 12 L 4 necked round bottom flask, 250 g of 6 mm diameter soda lime glass beads were added. The intermediate 6a (290 g, 0.62 mol, 1.0 eq) was dissolved in HPLC grade acetone (5850 mL, 20 volumes) under argon using large magnetic stir (400 rpm) and overhead stirrer (50 rpm). To this solution $K_2CO_3$ (454.20 g, 3.29 mol, 5.3 eq.) was added portion wise over 3 minutes. After stirring for 5 minutes, $Me_2SO_4$ (242 mL, 2.56 mol, 4.1 eq) was added dropwise over 39 minutes. The reaction mixture was stirred at ambient temperature for about 63 hours. The progress of reaction was periodically monitored by TLC (spotting on silica gel on glass; developing with 10% EtOAc hexanes; visualized by UV 254 nm and then PMA staining). After completion of the reaction, the reaction mixture was filtered using sintered glass funnel and the solid was rinsed using 3×290 mL acetone. The filtrate and rinses were combined and were rotary evaporated at 35° C. bath temperature under reduced pressure to give 536 g of residue which was suspended in MTBE (4350 mL) and washed with USP purified $H_2O$ (2×2600 mL), followed by brine (1×2900 mL). After drying over 766 g of $Na_2SO_4$, the content was filtered using sintered glass funnel and solid was rinsed with 3×100 mL MTBE. The mixture of filtrate and rinses was rotary evaporated at 35° C. bath temperature under reduced pressure to get 564 g of crude Intermediate 7.

To purify crude Intermediate 7, a glass column (D=8", L=52") was packed with silica gel (7252 g) in hexanes. The crude Intermediate 7 was dissolved in 564 mL of hexanes and loaded onto the column using a peristaltic pump. The flask containing crude Intermediate 7 was rinsed multiple times with hexanes (total of 1750 mL) and loaded onto the column. The column was eluted with following eluents: hexanes (20.0 L); 0.6% EtOAc/hexanes (33.6 L); 1.2% EtOAc/hexanes (101.27 L). The fraction size was 2.9 L. The fractions were analyzed by TLC (spotting on silica gel on glass; developing with 10% EtOAc in hexanes; visualized under UV 254 nm then PMA staining). Fractions containing pure intermediate 7 were combined and concentrated to obtain 277 g of Intermediate 7 (L) SAP-41-065-step-1-35. This material was taken to next step without further analysis.

Step 7. Synthesis of HU308 (SAP-41-065 (Engineering Batch))

In a 12 L 4 necked round bottom flask, the intermediate 7 (276 g, 0.553 mol, 1.0 eq) was dissolved in MeOH (5520 mL) under argon. To this solution USP purified $H_2O$ (220 mL, 12.222 mol, 22 eq) was added, followed by a solution NaOMe in MeOH (5 mol/L, 999 mL, 4.995 mol, 9.0 eq). While stirring with overhead stirrer, the reaction mixture was heated to 37° C. using heating mantle and temperature controller. The reaction progress was monitored by TLC (spotting on silica gel on glass; developing with 10% EtOAc/hexanes; visualized under UV 254 nm and then PMA staining). After 43 hr and 42 minutes, the reaction mixture was cooled using ice bath to 4.8° C. The pH of the reaction mixture was adjusted to 6 using acetic acid with dropwise addition using dropping funnel to maintain internal temperature below 10° C. The reaction mixture was rotary evaporated at 35° C. under vacuum. The residue was suspended in EtOAc (4.9 L) and washed with $H_2O$ (1×2.9 L). The aqueous layer was extracted with EtOAc (2×1.45 L). The combined organic layer was washed with sat. $NaHCO_3$ (1×2.9 L), followed by brine (1×2.9 L). After drying over $Na_2SO_4$ (653 g) and filtration, the filtrate was concentrated at 35° C. under vacuum to dryness to give 283 g of the crude product HU308.

The crude product was purified via column chromatography. A glass column (D=8"×L=52") was packed with 2.9 kg silica gel in hexanes. The crude product was dissolved in 142 mL of DCM and loaded on the column. It was eluted in sequence with 3% EtOAc/hexanes (17.40 L); 8% EtOAc/hexanes (13.04 L) and 10% EtOAc/hexanes (46.44 L). Each 2.9 L fraction was analyzed by TLC as before. All fractions containing pure HU308 were pooled and rotary evaporated at 35° C. bath temperature. The isolated product was dissolved in 2.9 L DCM and filtered through a clean sintered glass funnel. The flask and funnel were rinsed multiple times with DCM (total 870 mL) and filtered. The combined filtrate and rinses were rotary evaporated in a 20 L wide mouth flask under reduced pressure. The evaporated residue was co-evaporated with 3×100 mL and 200 mL hexanes. Then the product was dried under high vacuum at 35° C. to until the constant weight was reached and an oily product was obtained. It was hydrated (crystalized) by mixing with 2440 mL USP water for 15 hours. Then the supernatant was carefully decanted into a clean vessel. The solid was grinded using pestle and mortar. Powdered solid and the decanted supernatant were combined and stirred vigorously for another 24 hours at room temperature. The hydrated solid was filtered through the sintered glass funnel and the solid was rinsed multiple times with USP water (total 500 mL). The solid was air dried for 2 hours on the funnel under air suction through the solid. Then the solid was transferred to glass tray and dried in the vacuum oven at room temperature until the weight stabilizes. It gave 251.33 g (yield 83% for last two chemistry steps) of final product HU308 (L) SAP-41-065. The structure of HU308 was confirmed by $^1$H-NMR and $^{13}$C-NMR.

Example 5—Re-Purification of Didesmethyl HU308 Pivalate (HU308 Intermediate 6a)

The impure HU308 Intermediate 6a during synthesis had two impurities which had very close Rf values with the product; one was less polar than the product and the other one was more polar than product. Therefore, the desired product was difficult to purify. It required large amount of silica gel and solvent and time to purify. It was also noticed that between pure product fractions, few fractions had product with polar impurity (lacking linearity). It is suspected that this product is unstable to hold in silica gel for long time. So, it was decided to purify in small portions and fast elution.

For trial purification, two silica gel (2×110 g) cartridges were mounted by stacking one over the other on to the Biotage and equilibrated with eluent (2% acetone/0.5% EtOH/hexanes). Sample (10 g) was dissolved in 1.5 volumes of eluent and loaded onto the column under gravity. Then, the column was eluted with eluent at 80 mL/min flow rate. The following setup was used in Biotage: 40 mAu start threshold; 254 nm and 280 nm wavelengths for fraction collection; collect all with 50 mL fraction size. After checking by TLC, appropriate fractions were combined and concentrated at 30-35° C. It gave 7.34 g of HU308 Intermediate 6a (L) SPS-04-197-P. The impure portion (SPS-04-197-P1, 3.4 g) was re-purified as before and combined with main portion to get 8.56 g of Didesmethyl HU308 Pivalate (HU308 Intermediate 6a) (L) SPS-04-199-P (85.6% recovery). The purity was 99.31 by HPLC.

Based on the trial purification information, the rest of HU308 Intermediate 6a (L) SAP-41-063-101421 (about 239 g) was purified. It was split in three portions and each individually purified (SPS-05-19 to 23) using Biotage XL system with two stacked 800 g silica gel cartridges. The same eluent system as trial purification was used to equilibrate the column, prepare the sample solution, and elute the column. The flow rate of the column was 300 mL/min. The fraction size was 220 mL. During purification, a top spot was completely removed from the main portion. After combining the multiple column products and drying, it gave 201 g of Didesmethyl HU308 Pivalate (HU308 Intermediate 6a)-(L)-(SAP-41-143) with purity 96.34% by HPLC and chiral purity 96.03% enantiomeric excess by chiral HPLC.

This material was re-purified with anew system of eluent 0.5% acetone/2% EtOAc/hexanes. It was decided to purify 2× about 67 g portions. Sample solution was prepared by dissolving in half volumes of 50% DCM/hexanes. Another 0.3 volumes of 50% DCM/hexanes was used to rinse the source flask and load onto the column. The column was eluted at 300 mL/min flow rate. Approximately 60 L eluent was used for purification of each portion. For each portion, about 141×220 mL fractions were collected and analyzed by TLC as before. The fractions were pooled in three categories: Top impurity plus product (L) SAP-41-159-TP, product (L) (SAP-41-159-C1P1, SAP-41-159-C1P2 and SAP-41-159-C2P) and product plus bottom impurities (L) SAP-41-159-PB. The 12.14 g of top impurity plus product (L) SAP-41-159-TP was discarded. The purities for the rest combined fractions were not less than 98.5% by HPLC. All the quality control passed portions were combined using DCM, concentrated under vacuum at 35° C. and dried under high vacuum to obtain about 110 g of Didesmethyl HU308 Pivalate (HU308 Intermediate 6a) (L) SAP-41-159.

Procedure—Flush Chromatography Using Biotage XL with Prepacked Silica Gel Column (SAP-41-159)

The Biotage XL system was assembled with two stacked (2×800 g) silica gel cartridges and equilibrated with 5 L of hexanes. The crude (about 66.8 g) was dissolved in 30 mL (half volumes) of 50% DCM in hexanes and loaded onto the column under gravity. Another 20 mL (0.3 volumes) of 50% DCM in hexanes was used to rinse the flask and loaded onto the column. The column was eluted with 0.5% acetone/2% EtOAc in hexanes at 300 mL/minutes flowrate with following settings: Cartridge SNAP Ultra 1500 g; Start Threshold 40 mAu; UV 1 (monitor) 254 nm and UV 2 (monitor) 280 nm; Detection Mode Lambda-all and Lambda-all (collect). About 141×220 mL fractions were collected. About 3 μL samples were spotted on TLC plates (silica gel on glass; 60 Å; Fluorescent indicator). In the beginning and later fractions were spotted up 9 μL to have concentrated sample spots. It was developed in the 10% EtOAc in hexane. Each developed TLC plates were visualized by staining in PMA. The fractions were pooled together according to TLC profile. In this first column purification, the fractions 28 to 37 contained top impurity plus product and the pooled fraction was labeled as SAP-41-159-C1TP. The fractions 38 to 72 except fractions 54 and 62 contained pure product spots and the pooled fraction was labeled as SAP-41-159-C1P1. The fractions 54, 62 and 73-109 contained product plus bottom impurity and the pooled fraction was labeled as SAP-41-159-PB. The fractions 110 to 141 were tailing fraction with trace of product and the pooled fraction was labeled as SAP-41-159-C1P2. Each pooled portion was separately rotary evaporated at 35° C. bath temperature and sample from each concentrate were analyzed by HPLC except SAP-41-159-TP. Since the purity is NLT 98.5% by HPLC for all four analyzed samples (HPLC results are summarized in Table 1), they were combined by dissolving in DCM and transferred into a new 3 L one necked round bottom flask. This solution was rotary evaporated at <35° C. bath temperature. The residue was dried by rotary evaporator under high vacuum for 3 hours at <35° C. bath temperature to obtain about 110 g of Didesmethyl HU308 Pivalate (HU308 Intermediate 6a) (L) SAP-41-159. About 10 mg sample was dissolved in 0.5 mL of DCM and analyzed by 1H-NMR. It confirmed the structure, but had a traces of DCM and Acetone contamination.

| Sample Name | Sample lot# | % Purity of HU308 Int. 6a* |
|---|---|---|
| HU308 Intermediate 6a | SAP-41-159-PB | 98.94 |
| | SAP-41-159-C2P | 98.57 |
| | SAP-41-159-C1P1 | 98.91 |
| | SAP-41-159-C2P2 | 98.97 |

Note:
*Solvent peaks are not included

The final purities of Didesmethyl HU308 Pivalate (HU308 Intermediate 6a) exhibited about 46% recovery for the large scale purification. Due to the nature of Didesmethyl HU308 Pivalate (HU308 Intermediate 6a), chromatographic purification appears to be a logical choice based on our analysis and testing of the synthesis and purification protocols. Different mobile phases were developed: EtOAc/hexanes (0-6.5%); 0.5% Acetone/2% EtOAc/hexanes to remove bottom impurities and 0.5% EtOH/2% EtOAc/hexanes to remove top impurities.

Didesmethyl HU308 Pivalate (HU308 Intermediate 6a) Re-Purification Via Chiral Resolution Re-purification of Didesmethyl HU308 pivalate (HU308 intermediate 6a) was performed via chiral resolution. For this, about 300 g of HU308 chirally impure intermediate 6a (L) PN-03-165-p (purity 99.45% by HPLC and chiral purity 88.45% ee by chiral HPLC) is used to synthesize diastereomer 6a (The reaction scheme is presented in FIG. 29). Then, the pure diastereomer 6a is hydrolyzed and purified by silica gel column chromatography to obtain Didesmethyl HU308 Pivalate (HU308 Intermediate 6a) with purity not less than 98.5% by HPLC and chiral purity not less than 95% ee by chiral HPLC.

The chiral synthesis involves diester formation. When scaled up in this type of reaction there is a possibility for increased amount of mono ester intermediate as an impurity due to stirring rate and time limit for the reaction. Both diastereomers have very close Rf, therefor the purification needs large amount of silica gel and solvent and time to separate the isomers. It is also noticed that the peak tailing and later fraction come with very dilute amount of product. During staining the TLC plate with PMA to visualize the spots, spots dissolve and the spots smear. It creates confusion about the purity of the fraction.

The purified diastereomer 6a is hydrolyzed using NaOH aqueous solution in EtOH to regenerate HU308 Intermediate 6a. The crude hydrolyzed product is purified by silica gel column. Here it is also noticed that there are two impurities having very close Rf as product; one is less polar than product and the other one is high polar than product. Therefore it requires large amount of silica gel and eluent and time to purify HU308 Intermediate 6a. It is suspected that HU308 Intermediate 6a is an unstable compound. Therefore it is better to avoid large columns and long processing times.

The chiral synthesis was done in two batches starting from 250 g and 63 g of chirally impure HU308 Intermediate 6a (L) PN-03-165-p respectively. The HU308 Intermediate 6a was reacted with 2.2 mole equivalents of Boc-L-alanine in the presence of DMAP and DCC in anhydrous DCM under argon for 2 hours at ambient temperature. After filtering off the DCU by-product, the filtrate was rotary evaporated at 35° C. The crude yields of 151% and 126% were obtained respectively in both batches. To purify the crude product, it was split into two portions and each portion was first purified by large glass column packed silica gel.

Then the impure portions were purified by Biotage system. For each portion of the crude, a large 30 L column was packed with 27 times of silica gel in eluent (5% EtOAc in hexanes). The sample was loaded as solution in 0.8 times eluent. The column was head space filled with eluent and set a loop system, where a peristaltic pump pumps the eluent in and out for 19 hours. This helped to move the diastereomer spot close to bottom of the column without using extra solvent. It helped to save approximately 450 L of solvents. After breaking the loop, fraction collection was started in 4 L portions. The polarity of the eluent was also increased for each 20 L by half percentage. Each fraction was first spot check by TLC (10p L spotted on a silica gel plate and visualized by PMA). If there was no spot, the fraction was recycled as eluent. Otherwise, the fraction was labelled as fraction 1 and continue to collect fraction in 4 L portions.

Each fraction was analyzed by TLC. The collected fractions were pooled according to TLC profile. The impurity spots are very faint so approximately 9 μL was spotted for each fraction on TLC to concentrate the faint spots. Since the nonpolar spot, product and unwanted diastereomer spots have very close Rf values, the TLC plate was developed 2 to 3 times in order to obtain a clear separation of spots. During the staining of the TLC plate in PMA to visualize the spots, the spots dissolved in PMA solution and smeared with other spots. So, the TLC plates were stained upright for the earlier fractions. After top spots disappear, the TLC plates were stained upside down. It helped to avoid the confusions of the purity of the fractions. Mainly there were three pooled portions of interest: 50.83 g of top impurity plus product (L) SAP-41-127-TP, 288.23 g of product (L) SAP-41-127-P and 31 g of product plus bottom impurity (L) SAP-41-127-PB. Similarly, the second portion of the crude was purified and three pooled fractions were obtained: 12 g of top impurity plus product (L) PN-04-143-C2P2, 149 g of product (L) PN-04-143-C2P3, and 35 g of product plus bottom impurity (L) PN-04-143-C2P4. The 149 g of product (L) PN-04-143-C2P3 was re-purified via Biotage XL system due to the low purity (94.3% by HPLC).

The top impurity plus product fractions were combined and purified via Biotage XL system using a stack of 2×800 g silica gel cartridges. The column was equilibrated with 5.5% EtOAc in hexanes. The crude was loaded as solution with one volume of hexanes. It was eluted with 5.5 to 8% EtOAc in hexanes to remove the top spot. Then, the column was flushed with 15% EtOAc in hexanes to obtain the product. The product solution was evaporated to get 9.1 g product.

After repeated purification of impure portions via the Biotage system and combination of the all the pure fractions, 325 g of diastereomer 6a (L) PN-04-187 was obtained.

From this diastereomer 6a, one gram scale trial hydrolysis was performed and the product was analyzed for chiral purity. To a solution of diastereomer 6a in 10 volumes of EtOH, was added 3 mole equivalents of NaOH in 1 volume of water at below 10° C. for 5 to 6 minutes. The reaction mixture was stirred for 1 hour and 40 minutes while it was allowed to warm up ambient temperature. Then the reaction mixture was cooled with ice bath and quenched with 1 M HCl to pH 6. The reaction mixture was rotary evaporated, and the residue was extracted using EtOAc and water. After usual work-up and rotary evaporation, the crude product was purified using Biotage system with 2 stacked 12 g silica gel (24× silica gel). It was eluted with 0-4% EtOAc in hexanes. The product fractions were concentrated to have 514 mg (about 89% yield) of HU308.

According to the above hydrolysis procedure, the remainder of the 325 g of diastereomer 6a was hydrolyzed and 230.2 g of crude product (L) PN-04-195-cr was obtained. It was dissolved in 0.37 volumes of DCM at 35° C. This solution was diluted with mixing with 0.37 volumes of hexanes. This final solution was split into 3 portions and purified each portion using Biotage XL system with 1.6 kg silica gel cartridge. The column was first equilibrated with hexanes, then the first sample portion was loaded under gravity. The column was eluted at 250 mL/min. The elution was gradient using EtOAc/hexanes. First gradient was applied from 0 to 2.5%. Then, it was continued to elute with 2.5% until all yellow color impurity flowed out of the column. Then, the eluent polarity was increased gradually from 2.5 to 4%. The fractions containing top impurity plus product were pooled together and rotary evaporated. This impure portion was re-purified. After the combination of all the fractions which contained pure product, and concentrated under vacuum and drying under high vacuum, 146.6 g of HU308 Intermediate 6a (L) PN-04-195 was obtained in 78% yield with purity 99.40% by HPLC. The above product was combined with other batches of HU308 Intermediate 6a with purity greater than 98.5% by HPLC. Those batches were: SAP-41-159 (10.8 g), SAP-41-159-C2P (10 g) and SAP-41-167-C1P (56.8 g). These batches were dissolved in DCM, combined together in a 3 L flask and rotary evaporated to remove DCM at 30-35° C. bath temperature. It was noticed that the drying product started to foam. So, the product was co-evaporated with 3×500 mL hexanes. It helped to minimize the foaming. The product was dried under high vacuum on rotary evaporator at 30° C. bath temperature for 2 hours. It gave 217.03 g HU308 Intermediate 6a (L) PN-04-203.

Step 1: Boc-L-Alanine Coupling to Intermediate 6 (SAP-41-127)

A 4 necked 12 L RBF was equipped with Teflon coated stirred, overhead stirrer, thermocouple, temperature monitor, dropping funnel, argon inlet and outlet. In the argon protected reactor, anhydrous DCM (500 ml) and Boc-L-Ala (221.10 g) were added using a powder funnel. The funnel, scope and container were rinsed with 500 ml anhydrous DCM and added to the reactor. Another 500 ml portion of anhydrous DCM was added and stirred the mixture under argon. In a 2 L Erlenmeyer flask, DCC (241.10 g) with 500 ml anhydrous DCM was sonicated to make a colloidal solution. It was slowly added to the reactor for 10 minutes. The flask was rinsed with 500 ml of anhydrous DCM and added to the reactor. The internal temperature reached 28.7° C. To this reaction mixture, a solution of enantiomeric mixture (250 g) in 340 ml anhydrous DCM was added for 10 minutes. Internal temperature was 23.6° C. Finally, a solution of DMAP (6.49 g) in 100 mL anhydrous DCM was added for 5 minutes. The flask rinsed with 50 ml anhydrous DCM and added to the reactor. Internal temperature reached 34.8° C. It was stirred for 2 hours at ambient temperature under argon. The reaction was monitored by TLC. Three TLC plates were developed (silica gel on glass plate, mobile phase 10% EtOAc in hexane) and each visualized by different methods: PMA, $I_2$ vapour and ninhydrin. The reaction mixture was filtered through sintered glass funnel to remove the DCU. The solid was rinsed with 3 portions of hexanes (total volume 500 ml).

The filtrate plus rinse was rotary evaporated at 35° C. bath temperature. The residue was co-evaporated with 500 ml hexanes. It gave 630.64 g of crude distereomer 6a. The final crude was dissolved in solution of 5% 500 ml EtOAc in hexanes. About 70% of this solution was taken to purify by silica gel column chromatography. The rest of 30% solution is combined with the crude from the 2nd batch reaction, and purified using large glass column.

Purification Using Large Glass Column

A glass column (8" ID×62" L) was packed with 12 kg silica gel in 5% EtOAc/hexanes. The above sample was loaded onto the column under gravity. The flask was rinsed with 500 ml eluent (5% EtOAc/hexanes) and loaded to the column. It was continued to elute with 5×500 ml of eluent under gravity. Then about 5 L eluent was loaded to column and set a close loop system with a peristaltic pump. The column was eluted at 400 ml/min for 19 hours. Then the loop was broken and started to elute with fresh eluents of increased polarities EtOAc/hexanes: 5.5% 20 L, 6% 20 L, 6.5% 20 L, 7% 80 L, 7.5% 163 L and 8% 40 L. Product spot started to appear after eluting of 41 L of 7.5% eluent. About 4 L portions of fraction collection started at this point. Fractions were analyzed by TLC (silica gel on glass, 10% EtOAc in hexanes, PMA). Fractions were pooled into 3 portions according to the TLC profile: 1) Top impurity with product (about 500 L), 2) Product (about 100 L) and 3) product plus minor (about 30 L). Each portion was rotary evaporated separately to get 50.83 g of top impurity plus product, 288.23 g product and 31 g product with minor product.

Purification Using Biotage XL System. (PN-04-163)

The Biotage XL system was assembled with two stacked (2×800 g) silica gel cartridges and equilibrated with 5 L of hexanes. The impure fractions from the above large glass column (149 g) was dissolved in 1 volume of hexanes and ⅓ of the crude solution was loaded onto the column under gravity. The column was eluted with 3.75 L of hexanes. Then, each collected 3.75 L of fraction was spot checked on TLC and ninhydrin staining technique. Fractions that did not contain spots were mixed with 20 ml of EtOAc and injected to the column. That is, every 7.5 L of recycled eluent polarity increased by about 0.5%. After the polarity reached 5%, the column was eluted with 26.25 L of 5.5% and 60 L of 6% of fresh eluents. The column flow rate was set at 250 ml/min for 0% to 5.5% eluents and 300 ml/min for 6% eluent. Once the TLC spot check showed spot, 240 ml fractions were collected and analyzed by TLC (silica gel on glass plates; 10% EtOAc in hexanes; Ninhydrin staining). Fractions were pooled according to TLC profile. The column was cleaned by flushing with 4 L EtOAc then it was equilibrated with 7 L of hexanes to regenerate the column. The column was recycled for next ⅓ portion of the crude similar way then the column was regenerated again to use for final ⅓ portion. The combined all pure fractions from three column chromatography were rotary evaporated at 35° C. bath temperature.

Step 2 Ester Hydrolysis of Diastereomer 6a (L) PN-04-195

A 4 necked 10 L round bottom flask was equipped with Teflon coated stir rod, overhead stirrer, thermo couple, temperature control, addition funnel, argon inlet and outlet. The diastereomer 6a (324 g, 0.399 mole) was dissolved using 3.24 L abs. ethanol under argon in the 10 L reactor. It was stirred at 250 rpm and cooled with ice/water bath to 9.7° C. To this, a solution of NaOH (47.8 g, 1.195 mole) in 324 mL USP water was added dropwise using dropping funnel for 6 minutes. The final temperature of the reaction mixture reached 8.4° C. The cooling bath was removed and the reaction mixture was left to warm up to ambient temperature for 2 hours and 45 minutes. The reaction progress was monitored by TLC (Silica gel on glass; mobile phase 10% EtOAc/hexanes; $I_2$ vapour). After all the starting material was consumed, the reaction mixture was cooled with ice/ water bath to below 15° C. It was quenched with 1 M HCl solution by adding dropwise below 15° C. After the pH of the reaction mixture was adjusted to 6, the reaction mixture was rotary evaporated at 35° C. bath temperature under reduced pressure to remove EtOH. After almost no distillate condensing, the residue was mixed with 1.7 L DCM plus 1.7 L USP water. The bilayers were separated. The aqueous layer was back extracted with 2×0.7 L DCM. The combined organic layer was washed with 1 L brine. The brine layer was back extracted with 2×0.25 L DCM. The combined organic layer was dried over Na2SO4 and filtered. The filtrate was rotary evaporated and dried under high vacuum to obtain 230.2 g crude product (L) PN-04-197-cr as an amber oil.

Purification of the Crude by Biotage XL System

The crude was dissolved in 85 mL (0.37 volumes) of DCM at 35° C. bath temperature. The solution was mixed with 85 mL (0.37 volumes) of hexanes. The crude was split into 3 portions. A 1.6 kg silica gel cartridge was mounted on Biotage XL and the column was equilibrated using 3 column volumes (CV) of hexanes. The first portion of the crude solution was loaded onto the column under gravity. The column was first eluted with gradient eluent of EtOAc In hexanes: 0% 6 L; 0.5% 4 L; 1% 4 L; 1.5% 4 L and 2% 4 L. Then, it was kept eluting with 2.5% eluent to get rid of yellow color material out of the column. Then, the polarity of the eluent was increased gradually: 3% 2 L; 4% 2 L; 5% 4 L. The rate of elution was 250 mL/minute. The fraction volume was 225 mL. Each fraction was analyzed by TLC (silica gel on glass plate; mobile phase 10% EtOAc in hexanes; visualized by PM staining). The fractions were pooled together according to TLC profile and each portion was separately rotary evaporated at 35° C. bath temperature. Mainly there were 2 categories of pooled portions: Top spot plus product and Product. Similarly, the other 2 portions were purified. Then, the top impurity plus product portion of each column was combined and dried to have 67.27 g of impure HU308 Int. 6a (L) PN-04-195-TP, which was re-purified following the similar method as the previous column purification. After combining product portions of each column, it was dried under vacuum to have 146 g of Didesmethyl HU308 pivalate (HU308 Int. 6a) (L) PN-04-195.

The final purities of Didesmethyl HU308 Pivalate (HU308 Intermediate 6a) after re-purification via chiral resolution met internal desired specifications with 46.6% recovery for the large scale purification. Due to the very close Rf values among distereomers and impurities, and smeared TLC plates, the purity determination based only on TLC analysis is not considered good enough. The following measurements and procedures were introduced during the purification: In order to have clear TLC picture, TLC plates were stained upright for the earlier fractions. After top spots disappear, the TLC plates were stained upside down. Also, the purity of the diastereomer was checked by HPLC before hydrolysis. Further, a trial hydrolysis was performed and the chiral purity profile was established before scaling up the hydrolysis.

REFERENCES

1. Mechoulam, R., Lander, N., Breuer, A., and Zahalka, J. (1990). Synthesis of the individual, pharmacologically distinct enantiomers of a tetrahydrocannabinol derivative. *Tetrahedron Asymmetry* 1, 315-318.

2. Mechoulam, R., Peters, M., Murillo-Rodriguez, E., and Hanus, L. O. (2007). Cannabidiol-recent advances. *Chem. Biodivers.* 4, 1678-1692.

3. Hanus, L., Breuer, A., Tchilibon, S., Shiloah, S., Goldenberg, D., Horowitz, M., et al. (1999). HU308: a specific agonist for CB(2), a peripheral cannabinoid receptor. *Proc. Natl. Acad. Sci. U.S.A.* 96, 14228-14233.

4. Ofek, O., Karsak, M., Leclerc, N., Fogel, M., Frenkel, B., Wright, K., et al. (2006). Peripheral cannabinoid receptor, CB2, regulates bone mass. *Proc. Natl. Acad. Sci. U.S.A.* 103, 696-701.

5. Rajesh, M., Mukhopadhyay, P., Batkai, S., Hasko, G., Liaudet, L., Huffman, J. W., et al. (2007). CB2-receptor stimulation attenuates TNF-alpha-induced human endothelial cell activation, transendothelial migration of monocytes, and monocyte-endothelial adhesion. *Am. J. Physiol. Heart Circ. Physiol.* 293, H2210-H2218.

6. Rajesh, M., Pan, H., Mukhopadhyay, P., Bátkai, S., Osei-Hyiaman, D., Haskó, G., et al. (2007). Cannabinoid-2 receptor agonist HU308 protects against hepatic ischemia/reperfusion injury by attenuating oxidative stress, inflammatory response, and apoptosis. *J. Leukoc. Biol.* 82, 1382-1389.

7. Smoum, R., Baraghithy, S., Chourasia, M., Breuer, A., Mussai, N., Attar-Namdar, M., et al. (2015). CB2 cannabinoid receptor agonist enantiomers HU433 and HU308: an inverse relationship between binding affinity and biological potency. *Proc. Natl. Acad. Sci. U.S.A.* 112, 8774-8779.

8. Gonçalves, E. C. D., Baldasso, G. M., Bicca, M. A., Paes, R. S., Capasso, R., Dutra, R. C. (2020). Terpenoids, Cannbimimetic Ligands, beyond the *Cannabis* Plant. *Molecules,* 25, 1567.

9. Morales, P., Reggio, P. H., Jagerovic, N. (2017). An Overview on Medicial Chemistry of Synthetic and Natural Derivatives of Cannabidiol. *Frontiers in Pharmacology,* 8, 422.

10. U.S. Pat. No. 6,903,137

11. U.S. Pat. No. 9,428,431

All references cited herein are incorporated herein by reference in their entireties. The present invention has been described with regard to one or more embodiments. However, it will be apparent to persons skilled in the art that a number of variations and modifications can be made without departing from the scope of the invention as defined in the claims.

What is claimed is:

1. A method of enantioselectively preparing a compound of formula 8:

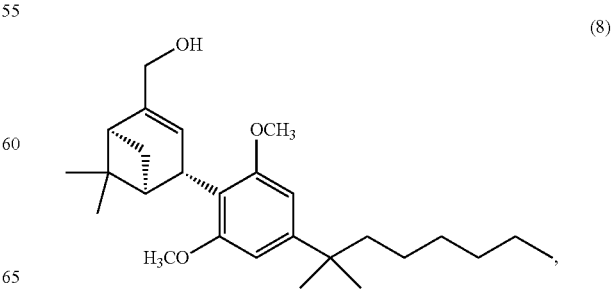

(8)

the method comprising:

providing a first reactant of formula 12,

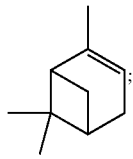

(12)

performing a first allylic oxidation comprising compound 12, SeO$_2$, and peroxide, to yield a compound of formula 13:

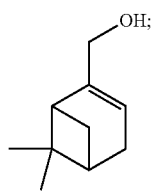

(13)

performing a protection reaction comprising compound 13, acid chloride, dichloromethane (DCM), and a first base, to yield a compound of formula 14:

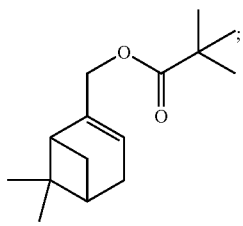

(14)

performing a second allylic oxidation comprising compound 14, CrO$_3$, tert-butyl hydroperoxide (TBHP), and a first solvent, to yield a compound of formula 15:

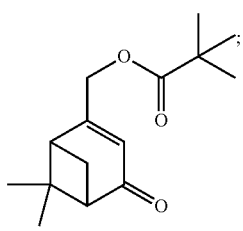

(15)

performing a reduction reaction comprising compound 15, sodium borohydride (NaBH$_4$), and ethanol, to yield a compound of formula 16:

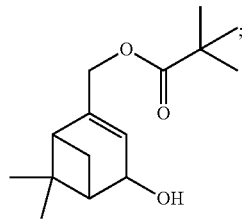

(16)

performing an acid-catalyzed coupling reaction comprising compound 16, an acid, DCM, and a compound of formula 2:

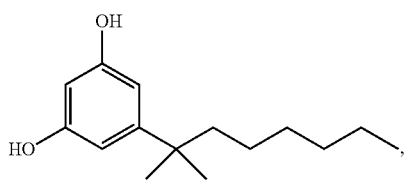

(2)

to yield a first mixture comprising a compound of formula 6:

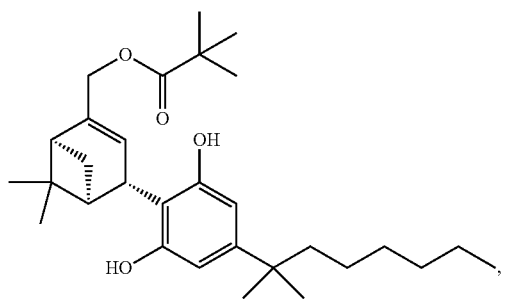

(6)

and a compound of formula 17:

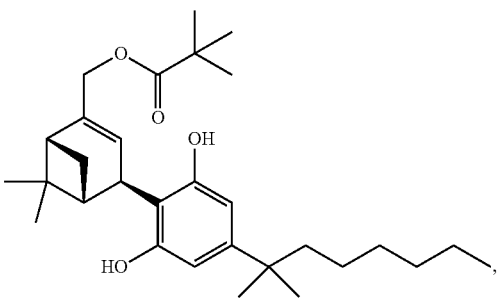

(17)

performing a coupling reaction comprising the first mixture, Boc-alanine, N,N'-dicyclohexylcarbodiimide (DCC), and 4-dimethylaminopyridine (DMAP), to yield a second mixture comprising a compound of formula 10:

(10)

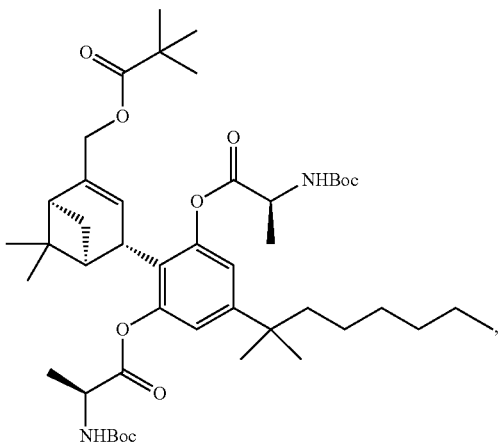

and a compound of formula 11:

(11)

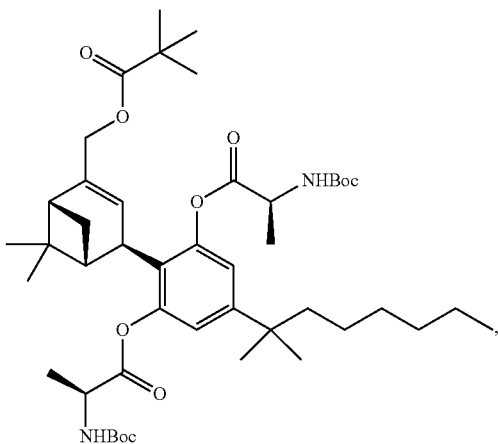

purifying the second mixture to yield enantiomerically purified compound 10;
performing a hydrolysis reaction comprising enantiomerically purified compound 10, a third base, and a third solvent, to yield enantiomerically purified compound 6;
performing a methylation reaction comprising enantiomerically purified compound 6, dimethyl sulfate ($Me_2SO_4$), potassium carbonate ($K_2CO_3$), and acetone, to yield an enantiomerically purified compound of formula 7:

(7)

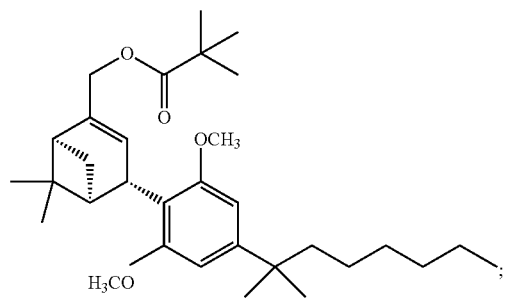

performing a deprotection reaction comprising enantiomerically purified compound 7, a second base, and a second solvent, to yield the enantiomerically purified compound 8; and
isolating the enantiomerically purified compound 8.

2. The method of claim 1, wherein the peroxide is tert-butyl hydroperoxide (TBHP).

3. The method of claim 1, wherein the first allylic oxidation comprises 1 eq. compound 12, 0.036-1.19 eq. $SeO_2$, and 0-3.5 eq. peroxide.

4. The method of claim 3, wherein the first allylic oxidation comprises 0.036 eq. $SeO_2$, 2.0 eq. TBHP, 0.45 eq. $NaBH_4$, and is conducted at room temperature.

5. The method of claim 4, wherein the acid chloride is pivaloyl chloride.

6. The method of claim 1, wherein the first base is trimethylamine (TEA), 4-dimethylaminopyridine (DMAP) or pyridine.

7. The method of claim 1, wherein the protection reaction comprises 1 eq. compound 13, 1.2-2.0 eq. acid chloride, 6 vol. of dichloromethane (DCM), and 1.5-6 eq. of the first base.

8. The method of claim 7, wherein the acid chloride is pivaloyl chloride, the first base is pyridine, and the protection reaction comprises 1.2 eq. pivaloyl chloride, 1.5 eq. base and 6 vol. of DCM.

9. The method of claim 1, wherein the second allylic oxidation comprises 1 eq. compound 14, 0.05-0.5 eq. $CrO_3$, 3.15-7 eq. tert-butyl hydroperoxide (TBHP), and 14.6-16 vol. of the first solvent.

10. The method of claim 1, wherein the first solvent is acetonitrile (ACN) or DCM.

11. The method of claim 9, wherein the second allylic oxidation comprises 0.5 eq. $CrO_3$, 3.15 eq. TBHP, 14.6 vol. of the first solvent and the second allylic oxidation occurs at an initial temperature of 0° C. and a final temperature of room temperature; and wherein the first solvent is ACN.

12. The method of claim 9, wherein the second allylic oxidation comprises 0.05 eq. $CrO_3$, 7 eq. TBHP, 16 vol. of the first solvent and the second allylic oxidation occurs at room temperature; and wherein the first solvent is DCM.

13. The method of claim 1, wherein the reduction reaction comprises 1 eq. of compound 15, 1.05-1.32 eq. of sodium borohydride ($NaBH_4$) and 10-18 vol. of ethanol (EtOH) and is conducted at room temperature.

14. The method of claim 13, wherein the reduction reaction comprises 1.1 eq. of $NaBH_4$, 10 vol. of EtOH and is conducted at room temperature over a period of 30 minutes.

15. The method of claim 1, wherein the acid in the acid-catalyzed coupling reaction is para-toluenesulfonic acid (pTSA) or $MeSO_3H$.

16. The method of claim 1, wherein the acid-catalyzed coupling reaction comprises 1.02-1.1 eq. of compound 16, 0.05-0.28 eq. of pTSA, 35-112 vol. of DCM, and 1 eq. of the compound of formula 2.

17. The method of claim 1, wherein the acid-catalyzed coupling reaction comprises 1.02 eq. of compound 16, 0.1 eq. of pTSA, 35 vol. of DCM, and 1 eq. of the compound of formula 2.

18. The method of claim 1, wherein the acid-catalyzed coupling reaction comprises 0.05-0.2 eq. of $MeSO_3H$, 1.02 eq. of compound 16, 112 vol. of DCM and 1 eq. of the compound of formula 2.

19. The method of claim 1, wherein the acid-catalyzed coupling reaction comprises 0.2 eq. of $MeSO_3H$, 1.02 eq. of compound 16, 112 vol. of DCM and 1 eq. of the compound of formula 2.

20. The method of claim 1, wherein the methylation reaction comprises 1 eq. of enantiomerically purified compound 6, 2.5-5 eq. dimethyl sulfate ($Me_2SO_4$), 5.3-6.7 eq. of potassium carbonate ($K_2CO_3$), and 5-20 vol. of acetone and is conducted at room temperature.

* * * * *